United States Patent
Ludewig et al.

(10) Patent No.: US 12,139,719 B2
(45) Date of Patent: Nov. 12, 2024

(54) METHOD FOR INCREASING COLD OR FROST TOLERANCE IN A PLANT

(71) Applicants: KWS SAAT SE & Co. KGaA, Einbeck (DE); SUDZUCKER AG, Mannheim (DE)

(72) Inventors: Frank Ludewig, Einbeck (DE); Karsten Harms, Worms (DE); Wolfgang Koch, Einbeck (DE); Uwe Sonnewald, Erlangen (DE); Christina Mudsam, Veitsbronn (DE); Wolfgang Zierer, Haiming (DE); Cristina Martins Rodrigues, Kaiserslautern (DE); Isabel Keller, Kaiserslautern (DE); Benjamin Pommerrenig, Kaiserslautern (DE); Ekkehard Neuhaus, Kaiserslautern (DE)

(73) Assignees: KWS SAAT SE & Co. KGaA, Einbeck (DE); SUDZUCKER AG, Mannheim (DE)

( * ) Notice: Subject to any disclaimer, the term of this patent is extended or adjusted under 35 U.S.C. 154(b) by 0 days.

(21) Appl. No.: 17/783,711

(22) PCT Filed: Dec. 11, 2020

(86) PCT No.: PCT/EP2020/085835
§ 371 (c)(1),
(2) Date: Jun. 9, 2022

(87) PCT Pub. No.: WO2021/116448
PCT Pub. Date: Jun. 17, 2021

(65) Prior Publication Data
US 2023/0332170 A1    Oct. 19, 2023

(30) Foreign Application Priority Data
Dec. 13, 2019 (EP) .................... 19215963

(51) Int. Cl.
C12N 15/82 (2006.01)
C07K 14/415 (2006.01)

(52) U.S. Cl.
CPC ........ *C12N 15/8273* (2013.01); *C07K 14/415* (2013.01); *C12N 15/8245* (2013.01); *C12N 15/827* (2013.01)

(58) Field of Classification Search
CPC ............ C12N 15/8273; C12N 15/8245; C12N 15/827; C07K 14/415; Y02A 40/146
See application file for complete search history.

(56) References Cited

U.S. PATENT DOCUMENTS

| | | |
|---|---|---|
| 7,767,801 B2 | 8/2010 | Hehl et al. |
| 9,222,102 B2 | 12/2015 | Kraus et al. |
| 10,961,543 B2 | 3/2021 | Koch et al. |

FOREIGN PATENT DOCUMENTS

| | | | |
|---|---|---|---|
| CN | 107 723 295 A | 2/2018 | |
| EP | 0120516 A2 | 10/1984 | |
| EP | 0449375 A2 | 10/1991 | |
| EP | 3 546 582 A1 | 3/2018 | |
| WO | 97/20056 A2 | 6/1997 | |
| WO | 99/29881 A1 | 6/1999 | |
| WO | 01/85963 A2 | 11/2001 | |
| WO | 02/40687 A2 | 5/2002 | |
| WO | 2007/047859 A2 | 4/2007 | |
| WO | 2009/059195 A2 | 5/2009 | |
| WO | 2010/079430 A1 | 7/2010 | |
| WO | 2011/032537 A1 | 3/2011 | |
| WO | 2011/072246 A2 | 6/2011 | |
| WO | WO-2012068445 A2 * | 5/2012 | ........... C07K 14/415 |
| WO | 2014/071006 A1 | 5/2014 | |
| WO | 2014/093622 A2 | 6/2014 | |
| WO | 2014/159845 A1 | 10/2014 | |
| WO | WO-2015154741 A1 * | 10/2015 | ........... C07K 14/415 |
| WO | 2017/190128 A1 | 11/2017 | |

OTHER PUBLICATIONS

*Arabidopsis thaliana* chromosome I BAC F9H16 genomic sequence, complete sequence GenBank Accession AC007369; Version AC007369.2 (Year: 2002).*
Hedrich, Rainer, Norbert Sauer, and H. Ekkehard Neuhaus. "Sugar transport across the plant vacuolar membrane: nature and regulation of carrier proteins." Current Opinion in Plant Biology 25 (2015): 63-70. (Year: 2015).*
Schneider, S., et al. "Vacuoles release sucrose via tonoplast-localised SUC4-type transporters." Plant Biology 14.2 (2012): 325-336 . (Year: 2012).*
Aoki, Naohiro et al. "The sucrose transporter gene family in rice." Plant & cell physiology vol. 44,3 (2003): 223-32. doi: 10.1093/pcp/pcg030 (Year: 2003).*

(Continued)

*Primary Examiner* — Cathy Kingdon Worley
*Assistant Examiner* — Kelsey L McWilliams
(74) *Attorney, Agent, or Firm* — Troutman Pepper Hamilton Sanders LLP

(57) ABSTRACT

The present invention relates to methods of increasing the cold tolerance of a plant or part thereof and/or preventing or inhibiting bolting of a plant, comprising deregulating phloem flux and plants or parts thereof having deregulated phloem flux. The invention also extends to the use of genes for deregulating phloem flux in a plant or part thereof; and/or increasing cold tolerance of a plant or part thereof; and/or preventing or inhibiting bolting in a plant. The invention also provides methods of selecting and/or producing a plant with deregulated phloem flux and/or increased cold tolerance and/or delayed or inhibited bolting. The invention also extends to constructs, isolated polynucleotides and polypeptides which can be used to deregulate phloem flux, plant cells transformed with such constructs, and to plants or parts thereof having deregulated phloem flux.

15 Claims, 16 Drawing Sheets

Specification includes a Sequence Listing.

(56) References Cited

OTHER PUBLICATIONS

Reinders, Anke, et al. "Protein-protein interactions between sucrose transporters of different affinities colocalized in the same enucleate sieve element." The Plant Cell 14.7 (2002): 1567-1577. (Year: 2002).*
Keskin, Ozlem, et al. "A new, structurally nonredundant, diverse data set of protein-protein interfaces and its implications." Protein Science 13.4 (2004): 1043-1055. (Year: 2004).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*
Thornton, Janet M., et al. "From structure to function: approaches and limitations." nature structural biology 7.11 (2000): 991-994. (Year: 2000).*
Wang, L., Yao, L., Hao, X et al. Tea plant SWEET transporters: expression profiling, sugar transport, and the involvement of CsSWEET16 in modifying cold tolerance in Arabidopsis. Plant Mol Biol 96, 577-592 (2018). https://doi.org/10.1007/s11103-018-0716-y (Year: 2018).*
Hackel, A., Schauer, N., Carrari, F., Fernie, A.R., Grimm, B. and Kuhn, C. (2006), Sucrose transporter LeSUT1 and LeSUT2 inhibition affects tomato fruit development in different ways. The Plant Journal, 45: 180-192. https://doi.org/10.1111/j.1365-313X.2005.02572.x (Year: 2006).*
Chincinska, Izabela A., et al. "Sucrose transporter StSUT4 from potato affects flowering, tuberization, and shade avoidance response." Plant Physiology 146.2 (2008): 515. (Year: 2008).*
Payyavula, Raja S., et al. "The sucrose transporter family in Populus: the importance of a tonoplast PtaSUT4 to biomass and carbon partitioning." The Plant Journal 65.5 (2011): 757-770. (Year: 2011).*
Eom, Joon-Seob, et al. "Impaired function of the tonoplast-localized sucrose transporter in rice, OsSUT2, limits the transport of vacuolar reserve sucrose and affects plant growth." Plant Physiology 157.1 (2011): 109-119. (Year: 2011).*
Lemoine, Remi, et al. "Identification of a pollen-specific sucrose transporter-like protein NtSUT3 from tobacco." FEBS letters 454.3 (1999): 325-330. (Year: 1999).*
Pin et al., "The Role of a Pseudo-Response Regulator Gene in Life Cycle Adaptation and Domestication of Beet," Current Biology (2012), vol. 22: pp. 1095-1101. DOI: 10.1016/j.cub.2012.04.007.
Dally et al., "The B2 flowering time locus of beet encodes a zinc finger transcription factor," Proc Natl Acad Sci (Jul. 15, 2014), vol. 111(28): 10365-10370.
Pfeiffer et al., "Genetic analysis of bolting after winter in sugar beet (Beta vulgaris L.)," Theoretical and Applied Genetics (Sep. 12, 2014), vol. 127: pp. 2479-2489. DOI: 10.1007/s00122-014-2392-x.
Pin et al., "An Antagonistic Pair of FT Homologs Mediates the Control of Flowering Time in Sugar Beet," Science (Dec. 3, 2010), vol. 330: pp. 1397-1398.
Liu et al., "Transport of sucrose, not hexose, in the phloem," Journal of Experimental Botany (Jun. 28, 2012), vol. 63, Issue 11, pp. 4315-4320.
Murray, M.B. et al., "Quantification of frost damage in plant tissues by rates of electrolyte leakage," New Phytol (1989), vol. 113, pp. 307-311.
Klemens, P.A.W et al., "Overexpression of the Vacuolar Sugar Carrier AtSWEET16 Modifies Germination, Growth, and Stress Tolerance in Arabidopsis," Plant Physiol. (Nov. 2013), vol. 163(3): pp. 1338-1352. DOI: 10.1104/ pp. 113.224972.
Klemens, P.A.W et al., "Overexpression of a proton-coupled vacuolar glucose exporter impairs freezing tolerance and seed germination," New Phytologist (2014), vol. 202(1): pp. 188-197. DOI: 10.1111/nph.12642.
McCallum et al., "Targeted screening for induced mutations," Nat Biotechnol. (Apr. 2000), vol. 18(4): pp. 455-457.

McCallum et al., "Targeting Induced Local Lesions IN Genomes (TILLING) for Plant Functional Genomics," Plant Physiology (Jun. 2000); vol. 123(2): pp. 439-442.
Ohshima et al., "Isolation of a Mutant of Arabidopsis thaliana Carrying Two Simultaneous Mutations Affecting Tobacco Mosaic Virus Multiplication within a Single Cell," Virology (1998), vol. 213, Article VY989078: pp. 472-481.
Okubara et al.. "Mutants of Downy Mildew Resistance in *Lactuca sativa*(Lettuce)," Genetics (Jul. 1994), vol. 137: pp. 867-874.
Quesada et al., "Genetic Analysis of Salt-Tolerant Mutants in *Arabidopsis thaliana*," Genetics (Jan. 2000), vol. 154: pp. 421-436.
Kusaba et al., "Low glutelin content1: A Dominant Mutation That Suppresses the Gluelin Multigene Family via RNA Silencing in Rice[W]," The Plant Cell (2003), vol. 15: pp. 1455-1467.
Potrykus, "Gene Transfer to Plants: Assessment of Published Approaches and Results," Annu. Rev. Plant Physiology Plant Mol. Biol. (1991), vol. 42: pp. 205-225.
Lindsey, K. et al., "Regeneration and transformation of sugar beet by Agrobacterium tumefaciens," (1991) Plant Tissue Culture Manual B7: pp. 1-13, Kluwer Academic Publishers.
Clough et al., "Floral dip: a simplified method for Agrobacterium-mediated transformation of *Arabidopsis thaliana*," Plant J. Dec. 1998., vol. 16(6): pp. 735-743.
Frame, B. R., Drayton, p. R., Bagnaall, S. V., Lewnau, C. J., Bullock, W. P., Wilson, H. M., Dunwell, J. M., Thompson, J. A. & Wang, K., "Production of fertile transgenic maize plants by silicon carbide whisker-mediated transformation," The Plant Journal (1994), vol. 6(6): pp. 941-948.
Meyer et al., "Endogenous and environmental factors influence 35S promoter methylation of a maize A1 gene construct in transgenic petunia and its colour phenotype", Mol. Gen. Genet. (1992), vol. 231, pp. 345-352.
Meyer et al., "The use of African cassava mosaic virus as a vector system for plants," Gene (1992), vol. 110: pp. 213-217.
An et al., Transformation of Tobacco, Tomato, Potato, and *Arabidopsis thaliana* Using a Binary Ti Vector System1, Plant Physiol. (1986), vol. 81, pp. 301-305.
Fraley, et al., "Genetic transformation in higher plants," Critical Reviews in Plant Sciences (1986), vol. 4(1): pp. 1-46. DOI: 10.1080/07352688609382217.
An et al., "New cloning vehicles for transformation of higher plants," EMBO Journal (1985), vol. 4(2): pp. 277-284.
Odell JT, Nagy F, Chua NH, "Identification of DNA sequences required for activity of the cauliflower mosaic virus 35S promoter." Nature (Feb. 28, 1985), vol. 313, pp. 810-812.
Zhang, W., McElroy, D., Wu, R., "Analysis of Rice Act1 5' Region Activity in Transgenic Rice Plants," The Plant Cell (1991), vol. 3, pp. 1155-1165.
Cornejo, M.J., Luth, D., Blankenship, K.M., Anderson, O.D., Blechl, A.E., "Activity of a maize ubiquitin promoter in transgenic rice," Plant Molecular Biology (1993), vol. 23, pp. 567-581.
Hull, R.; Sadler, J. and Longstaff, M., "The sequence of carnation etched ring virus DNA: comparison with cauliflower mosaic virus and retroviruses," The EMBO Journal (1986), vol. 5(12): pp. 3083-3090.
Oltmanns, H. et al., "Taproot promoters cause tissue specific gene expression within the storage root of sugar beet," Planta (2006), vol. 224: pp. 485-495. DOI: 10.1007/s00425-006-0230-3.
Noh, Seal Ah, et al., "A sweetpotato SRD1 promoter confers strong root-, taproot-, and tuber-specific expression in Arabidopsis, carrot, and potato," Transgenic Research (2012), vol. 21: pp. 265-278.
Goshu Abraha, Tsion, "Isolation and characterization of a culm-specific promoter element from sugarcane", diss Stellenbosch: University of Stellen—bosch (2005), 105 pages.
Govender, C., "Stem specific promoters from sorghum and maize for use in sugarcane", diss Stellenbosch: Stellenbosch University, 2008, 152 pages.
Mudge, S. R. et al., "Mature-stem expression of a silencing-resistant sucrose isomerase gene drives isomaltulose accumulation to high levels in sugarcane," Plant Biotechnology Journal (2013), vol. 11: pp. 502-509. DOI: 10.1111/pbi.12038.
Warner, S.A., Scott, R., Draper, J., "Isolation of an asparagus intracellular PR gene (AoPR1) wound-responsive promoter by the

(56) References Cited

OTHER PUBLICATIONS inverse polymerase chain reaction and its characterization in transgenic tobacco," The Plant Journal (1993), vol. 3(2): pp. 191-201.
Benfey & Chua, "Regulated Genes in Transgenic Plants," Science (Apr. 14, 1989), vol. 244: pp. 174-181.
Gatz, C., "Novel Inducible/Repressible Gene Expression Systems," Methods in Cell Biol. (1995), vol. 50, pp. 411-424.
Beucage, S.L. et al., "Deoxynucleoside Phosphoramidites—A New Class of Key Intermediates for Deoxypolynucleotide Synthesis," Tetrahedron Letters (1981, vol. 22(20), pp. 1859-1869.
Matthes et al., "Simultaneous rapid chemical synthesis of over one hundred oligonucleotides on a microscale," The EMBO Journal (1984), vol. 3(4): pp. 801-805.
Tatusova et al., "BLAST 2 Sequences, a new tool for comparing protein and nucleotide sequences," FEMS Microbiology Letters (1999), vol. 174(2): pp. 247-250.
Tatusova et al., Erratum to "BLAST 2 Sequences, a new tool for comparing protein and nucleotide sequences," FEMS Microbiology Letters (1999), vol. 177(1): pp. 187-188.
Altschul et al., "Basic Local Alignment Search Tool," J. Mol. Biol. (1990), vol. 215, pp. 403-410.
Higgins, D.G. & Sharp, P.M., "Clustal: a package for performing multiple sequence alignment on a microcomputer," Gene (1988), vol. 73(1), pp. 237-244.
Simon, R.J. et al., "Peptoids: A modular approach to drug discovery," PNAS (Oct. 1992), vol. 89(20): pp. 9367-9371.
Horwell, D.C., "The 'peptoid' approach to the design of non-peptide, small molecule agonists and antagonists of neuropeptides," Trends Biotechnol. (1995), vol. 13(4), pp. 132-134.
Gentleman et al., "Bioconductor: open software development for computational biology and bioinformatics," Genome Biology (2004), vol. 5, issue 10: Article R80, pp. 1-16.
Anders and Huber, "Differential expression analysis for sequence count data," Genome biology (2010), 11: R106, pp. 1-12.
Love et al., "Moderated estimation of fold change and dispersion for RNA-seq data with DESeq2," Genome Biology (2014), vol. 15: 550, pp. 1-21. DOI 10.1186/s13059-014-0550-8.
Sievers et al., "Fast, scalable generation of high-quality protein multiple sequence alignments using Clustal Omega," Molecular Systems Biology (2011), vol. 7: article 539, pp. 1-6. DOI: 10.1038/msb.2011.75.
Ronquist et al., "MrBayes 3.2: Efficient Bayesian Phylogenetic Inference and Model Choice Across a Large Model Spance," Systematic Biology (2012), vol. 61(3): pp. 539-542.
Jones et al., "The rapid generation of mutation data matrices from protein sequences," Bioinformatics (1992), vol. 8(3): pp. 275-282.
Whelan and Goldman, "A General Empirical Model of Protein Evolution Derived from Multiple Protein Families Using a Maximum-Likelihood Approach," Molecular Biology and Evolution (2001), vol. 18(5): pp. 691-699.
Metsalu and Vilo, "ClustVis: a web tool for visualizing clustering of multivariate data using Principal Component Analysis and heatmap," Nucleic Acids Research (May 12, 2015) vol. 43: pp. W566-W570.
Horst et al., "Ustilago maydis Infection Strongly Alters Organic Nitrogen Allocation in Maize and Stimulates Productivity of Systemic Source Leaves1[W][OA]," Plant Physiology (Jan. 2010), vol. 152: pp. 293-308.
Jung et al., "Identification of the transporter responsible for sucrose accumulation in sugar beet taproots," Nature Plants (Jan. 8, 2015), vol. 1: article 14001, pp. 1-6. DOI: 10.1038/nplants.2014.1.
Abel and Theologis, "Transient transformation of Arabidopsis leaf protoplasts: a versatile experimental system to study gene expression," The Plant Journal (1994), vol. 5(3): pp. 421-427.
Nieberl et al., "Functional characterisation and cell specificity of BvSUT1, the transporter that loads sucrose into the phloem of sugar beet (Beta vulgaris L.) source leaves," Plant Biology (2017), vol. 19(3): pp. 315-326. DOI: 10.1111/plb.12546.
Dohm et al., "The genome of the recently domesticated crop plant sugar beet (Beta vulgaris)," Nature (Jan. 23, 2014), vol. 505: p. 546 (1-16). DOI:10.1038/nature12817.
Volkert et al., "Loss of the two major leaf isoforms of sucrose-phosphate synthase in Arabidopsis thaliana limits sucrose synthesis and nocturnal starch degradation but does not alter carbon partitioning during photosynthesis", Journal of Experimental Botany (2014), vol. 65, No. 18, pp. 5217-5229.
Sturm, Molecular characterization and functional analysis of sucrose-cleaving enzymes in carrot (Daucus carota L.), Journal of Experimental Botany (1996), vol. 47, pp. 1187-1192.
Martin et al., "Expression of an Arabidopsis sucrose synthase gene indicates a role in metabolization of sucrose both during phloem loading and in sink organs", The Plant Journal (1993), vol. 4, No. 2, pp. 367-377.
Kovtun et al., "End-Product Control of Carbon Metabolism in Culture-Grown Sugar Beet Plants", Plant Physiology (1995), vol. 108, pp. 1647-1656.
Hesse et al., "Cloning and expression analysis of sucrose-phosphate synthase from sugar beet (Beta vulgaris L.)", Mol. Gen. Genet. (1995), vol. 247, pp. 515-520.
International Search Report and Written Opinion issued in PCT/EP2020/085835 dated Feb. 12, 2021.
Schulz et al., "Proton-driven sucrose symport and antiport are provided by the vacuolar transporters SUC4 and TMTI/2," The Plant Journal (2011), vol. 68, No. 1, pp. 129-136. DOI: 10.1111/j.1365-313X.2011.04672.x.
Ludewig et al., "Role of metabolite transporters in source-sink carbon allocation," Frontiers in Plant Science (Jul. 2, 2013), vol. 4, article 231, pp. 116. DOI: 10.3389/fpls.2013.00231.
Schneider et al., "Vacuoles release sucrose via tonoplast-localised SUC4-type transporters," Plant Biology (2011), vol. 14, No. 2, pp. 325-336.

\* cited by examiner

Figure 8
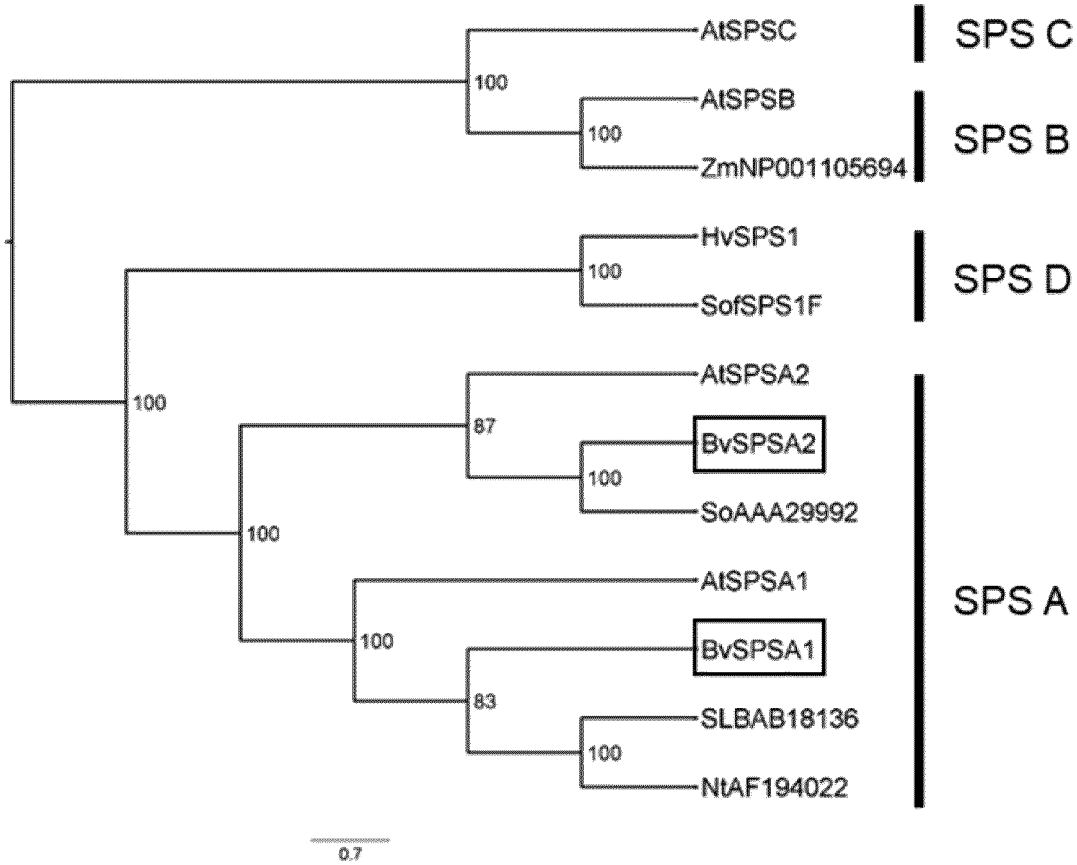
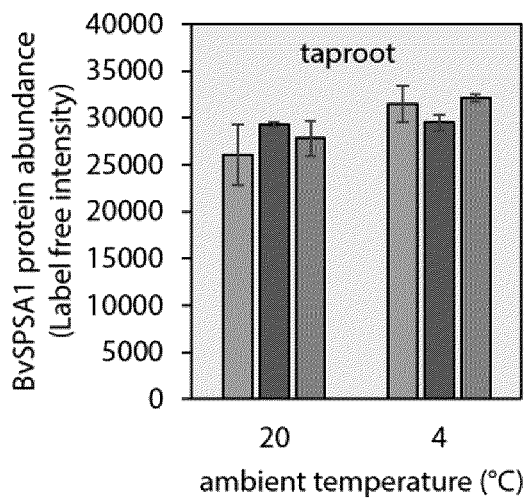
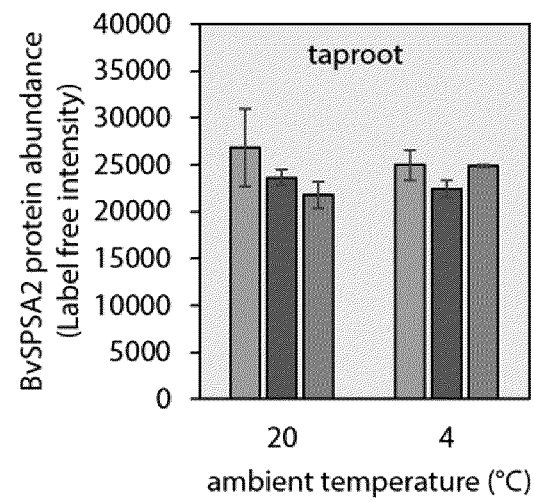

Figure 9
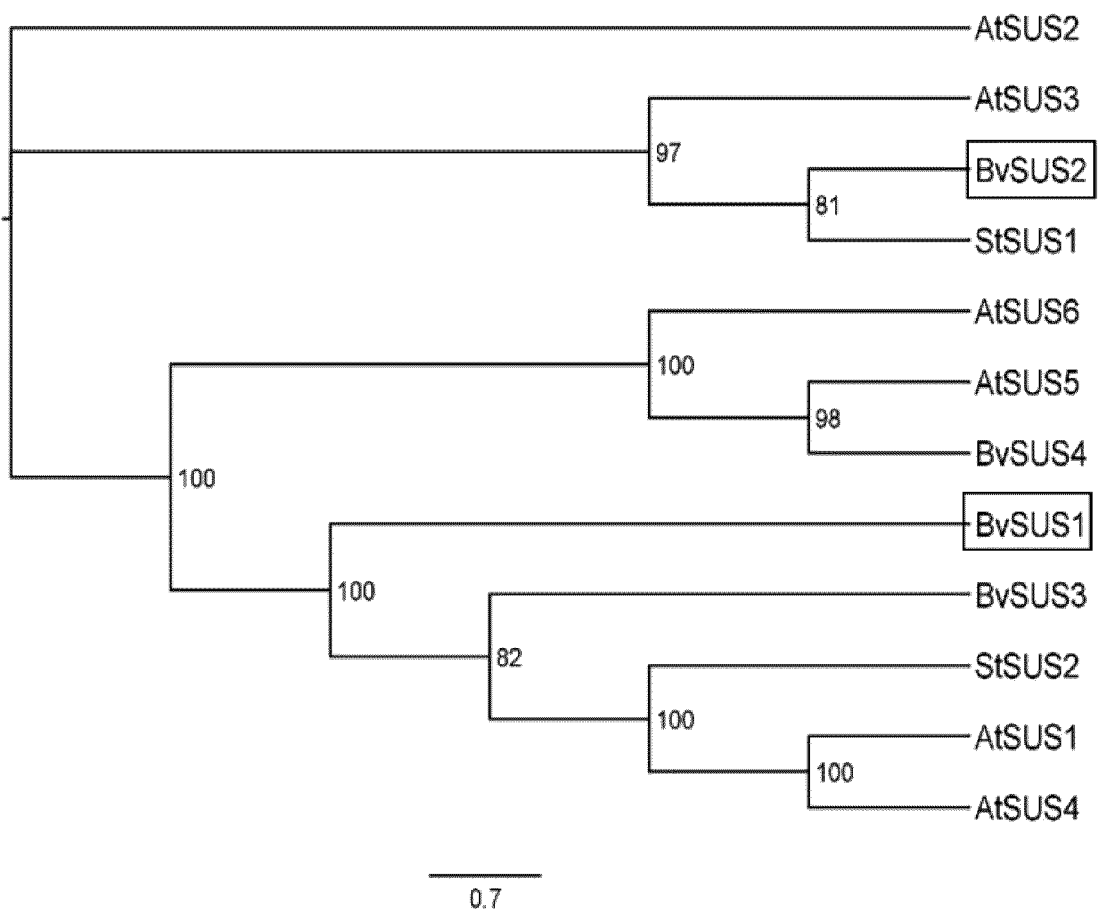
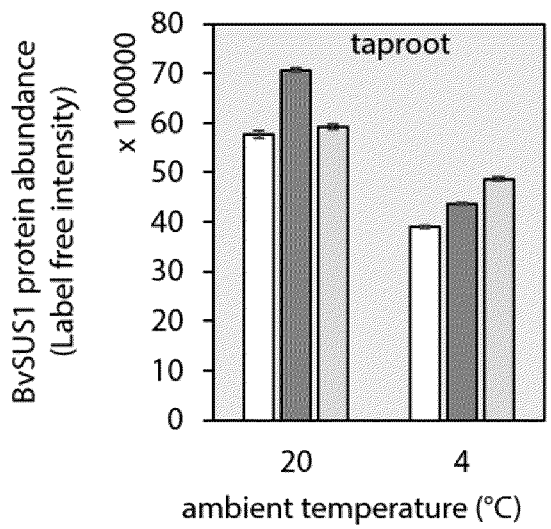
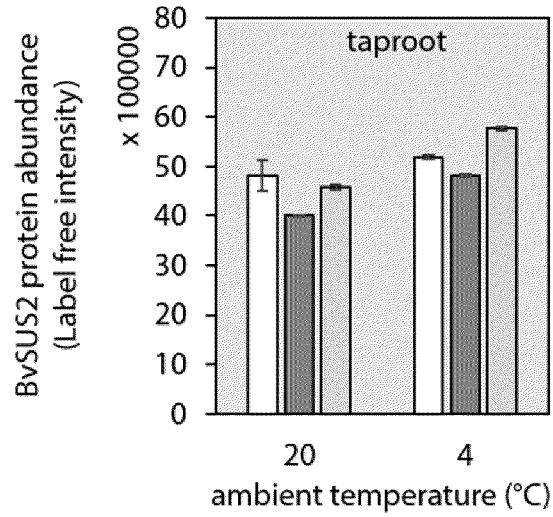

Figure 13

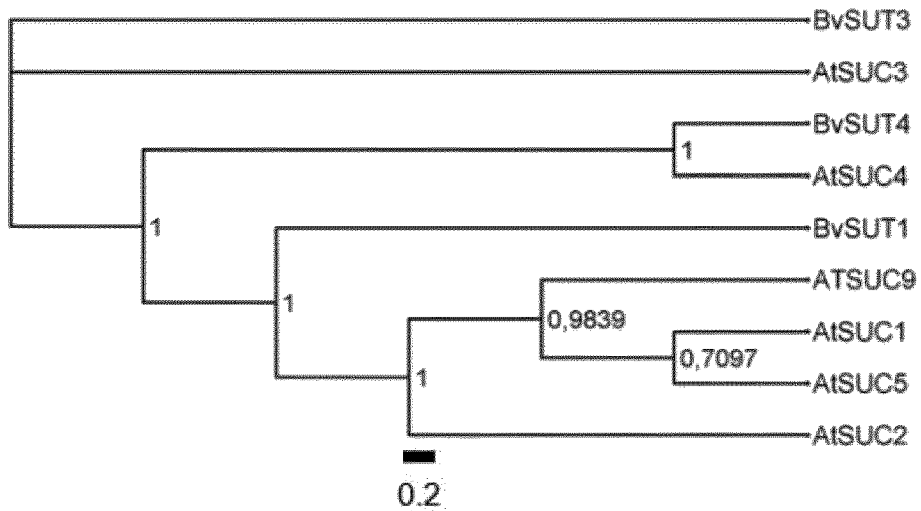

B

```
  1 MTGQDQNKTEITRETITKPRRQTHSSRQPRPTTRPPPPRPPQPPPTRPAR
 51 VPLKKLLKVTSVAGGIQFGWALQLSLLTPYVQELGIPHAFASIIWLCGPV
101 SGFIVQPLVGHISDRSTSRYGRRRPFILAGAAMIIAAVSIVGFSADIGFL
151 MGDKVDGGERKRPMAIVVFVIGFWLLDVANNTTQGPCRALLADLTGKDHR
201 RNRVANAYYSLYMAIGNILGFATGSYTSWYTILPFTRTHACSESCANLKS
251 AFLIDIIFIVITTYISITAAHEVPLNTEDGGTGISEGSQPSGHAEEAFFW
301 ELFGTFRYLPGPVWIILSVTALTWIGWFPFLLFDTDWMGREVYGGDPDEG
351 QIYHRGVSTGALGLMSQSVVLGITSLLMEKLCKKLGSGILWGISNIIMSL
401 CFVAMLVIAFVLSKADSFGSGSPPNGAVIAAVIVFTILGMPLAVTYSIPY
451 ALISSRIESLGLGQGLSMGVLHLAIVLPQVIVSLGSGPWDQLFGGGNSPS
501 IAVAGVASFASGLMAILALPRSRTDKSRVHVMHV*
```

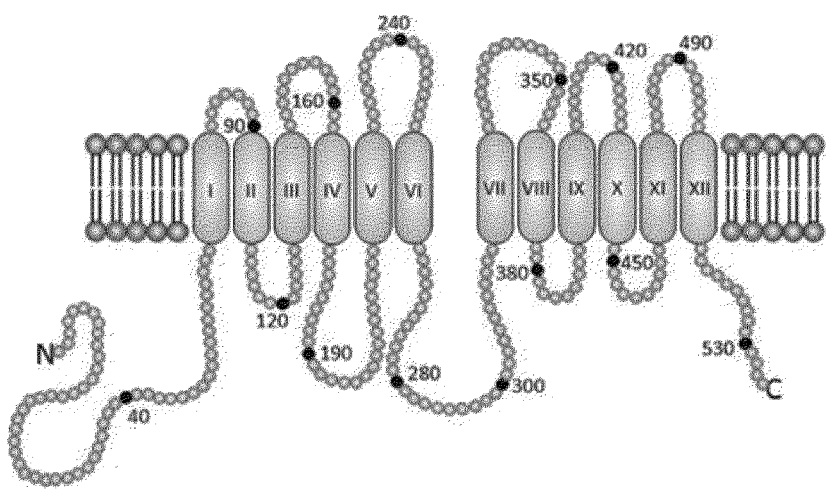

SEQUENCE LISTING

```
<160> NUMBER OF SEQ ID NOS: 21

<210> SEQ ID NO 1
<211> LENGTH: 4735
<212> TYPE: DNA
<213> ORGANISM: Beta vulgaris

<400> SEQUENCE: 1
cctattttct cagaggtgat gaagtaactg ataacacata attcatgaaa agttggctta      60
tttctcatct gggtttgttt attttccctt tttcttgcat gggttttttt gcttcagttt     120
tatgagttca gaaaagagca atactctctt gggttctctg attttttcttt ttgtttgttt    180 ttttggtgaa tttgattttg gtttgctttg attgcatgtg tttcatagct gaagtgaatt     240
tggattttga ttataatgtt tatgacagtt gattgaagaa gtttgattaa ctacttgagg     300
tgaaatatga gtgcagcagt attagttgca attgctgcaa cagttggaga tttgctgtat     360
ggatgggata atgctactat tgctggtaat ttgctcatta atttctacta tattgctcat     420
tactcatgct atgttttttct agtaaatctg ctcaatttcg aacccgattt gcttgattat    480
atttctgaag tttcttacac tcttagatat cacatatgaa aacccgagtt cactcatggt     540
```

```
acacccgggt gtaccatgag catggtacac ccaggggtat ttttgtaata aattagaatt    600
tcaagtgctc atttgacacc aaatttgctc atatgggcat tttgctcatt tactcatttg    660
ctcattttgt aataaaaatg tttgctcatt ttcttaaatg agtagaaatg tttgctcttt    720
gctcatttgt tcattttgtt catttgctca ttcgctcatt ttgagcattt agataaaatg    780
gtcttaggtg taccatgagc atggtacacc caggtgtatt ttaaatattc tcatgaaaac    840
ccctgcatag agatgagatg ccaaaagtaa agaaagacaa aggcacaaat taaatgatta    900
tcttcaggcc tcttgtttta tgagaaattc tattcattga ttataaagtt acataattat    960
ctgcttatgt gacgttgatt tatatgagaa attcatcttc agagacttat aaatcctact   1020
tagaatccta tgttggtttc agaaacatgg tttactgaga accattttt tggttgggtt    1080
tctttcctgt gttttgctct aggggctgta ttatatatta agaaagagtt caacttggag   1140
agttctccaa ccttggaagg gttaattgtg gccacatcaa taattggagc cactcttatt   1200
acaacatgtt ctggaccgat tgcagatcgt cttggtcgtc gccctatgat gataatttcc   1260
tcagtttgtt tctttgttag tgccttaata atgttgtggt ctcccaatgt ttatgtttta   1320
ctcttcggtc ggctattaga tggatttgga agtggtttgg cagtcactct tggtcctctt   1380
tatatatcag agaccgctcc aactgatata agaggctcac tgaacacact tcctcagttt   1440
actggttctg gtggaatgtt cctcgcatac tgcatggttt tcgggatgtc attgatggaa   1500
acacctagct ggagattaat gcttgggatt cttttgttc catctactgt ttatttttcta   1560
ttaactgtat tcttcttacc tgagtctcct cgctggcttg ttagcaaagg acggatgaat   1620
gaggctaaaa aggttcttca atggttgcga ggcaggaag atgtctttgg ttagtcttct    1680
gctactttcc atcattctat gtggtaaatt ttcttgtcca agtcgttttg ttagattcat   1740
gcatttgtat cgaaaaaaac gtatgctcct tttcaatttc atgccgacta tccttgcaga   1800
agaaattaag catgtttggg aagaataatc ggcgtaacaa aggagagttc agtaagatga   1860
attagttgca tattgataat gttaaatctt atagagacca aaattgatag taggaggatc   1920
atttcggaat acaggttgtt taattttgtt tatttgaaac taaagcaata atgcaattac   1980
caatttttt gaatgaacag ctgagatggc tctccttgtt gagggtctta gagttggagg    2040
tgatacatca atagaggaat acttgattga gccagatgct ggactcgctg aggatcaaga   2100
tccgatgact gtcaaagatc aggttaggct gtatgggtcc gaagcaggct gctcctgggt   2160
tgccagacca gtcactggtc agagtatgct gggtattgca tctcggcagg gaagcatgca   2220
gagtcctagt gttcctttaa tggatcccct tgtaactctt tttggtagtg tacatgaaaa   2280
gcttccagaa caaggaagta tgcttagtgt catattccca acttttggta gtatgtttag   2340
tatgggaggg aaaagagccca aaaatgaaga gtgggatgat gaaaatacta ttggggatga   2400
tgatgattat ggtcatgacg atgaagatta tgcaggtgat gctgatgaag atgacaattt   2460
acgtagttca cttatatctc gtcaggatac aggtccagac aaagccatgg ttgctcctac   2520
ttcaggtagc atgttcagca tgaagcatag tagttggtta caaggaagcg aagctagtgg   2580
tattggtggt ggttggcagt tagcttggaa atggagcgag agagaaggct tggatggtac   2640
gaaggaagga ggattcaaaa gactttatct acatcaggaa ggtgatgctg atctaaacg    2700
aggctctgtt atttctcttg ctggtggtga ggttattggc gacaatgagt atgtgaaggc   2760
tgctgcacta gtaagtcaac ctgccctta ttcgagggat ttcatggatc gggatagtat    2820
tggtccagct atggttcacc cttccgaggc ttctgcaaaa aggcctagtt ggagggattt   2880
tttagagcct ggtgtcaggc gtgcattagt tgttggtgtc ggacttcaac ttcttcaaca   2940
```

-continued

```
ggtaaaaggg tcaaaacctt ttcgaaagta tgttgattac taaacactac cttaccgtct    3000
gaatgtacta agtgacgttt tgtcatgaga ctcatgacta attcattaat ctaagttatc    3060
tacactatat agcatgtgaa ggatgacaac ttgttttttga aacttttccc ttcgctttct    3120
gcttcatgtc tgcttttcacc atcttagtct catacctct tttccctgct aactactgat    3180
atgtgtcatt gtatgacttg atctataatg tagttgggga atcataaact atattgctat    3240
cttgaattag agctgtctaa ttaagttatt gtgatgggtt agctaactaa gaatctactt    3300
gcaaattagc tatcacagaa tgttgttta agtttgtgg tgtttcaaat tgacaccatc    3360
acataatcta agcagtttcc ttggaataag aggatgtgcc ttggctctgt tctaaagcta    3420
ccataaacat attatttttt tcttttttttt atttgtaatt tttgtacagc ttttgtgcga    3480
acatattcac aattgacgtg cacatcctca gtggatgtgc cttcgctctg ttctaaagct    3540
accacaaaca tattttttttt ctttttttttt gtaattctta tatagctttt gttcggacat    3600
attcacaatt gacgcgcaca tcctcagctg ctatactgta taaatctgcc atcatttcct    3660
agtttcaaaa tttaaagctt tgcatggaca atcagctatc aatgtaccat attcatctgt    3720
ctcccattcc ccatacaatg tttgtttcaa aactggtttg tttttctgtg ctgtgcactt    3780
tttgtatttt atatgctgat atataaatgg gaaaaggggg atttgaagat gtgtacggga    3840
acacaagccc tcaatcttat gacttggtca atgccccatg tgatgtgctg tgaactttat    3900
ggtttattgt gaattgtact tgagcagttg agcttttggt tgtctcatga aacctgtcat    3960
ttttcttggt gcagttcgct gggataaatg gcgttctgta ttatactcct caaatactag    4020
agcaagctgg ggtgggtgat cttctttcgc atatgggtat aggcgcttcc tctgcattgt    4080
tactcatcag tgcactcaca actcttttga tgcttcctgc tatagctgtt gcaatgaggc    4140
ttatggatct ttctgggaga aggtaattac tttccaatct gtattctgtt tactaattta    4200 tttattttc cttggtgtgc atcatgttaa tgttattgtt tcttggcagg actttgctac    4260
taaccacaat tccggtgttg ttcttatcgc tcgttgtctt aatactcgca aatgtcataa    4320
agatgaacac cactgtgtat gcagtggtct ccacagtcgc ggtagttctc tacttctgct    4380
tctttgtgat ggggtttggg cctatcccaa atatcctatg tgcagaaatt ttcccaacca    4440
agattcgtgg agtctgtatt gctatttgtg cacttacttt ctggatctgt gatatcatag    4500
tcacctacac actccctatg atgcttaaag ctgttggact tgctggtctc tttggcttct    4560
atgctgttgt gattttaatt gcatggatat ttatattttt gaaggttcct gaaaccaagg    4620
gcatgcccct tgaggtaatc actgagttct ttgctctcgg tgcaagacaa gcaagccact    4680
gatgacaaga actgagttta agtttttaat aggtaattat tgatcgatca tttta         4735
```

<210> SEQ ID NO 2
<211> LENGTH: 2208
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of TST2.1

<400> SEQUENCE: 2

```
atgagtgcag cagtattagt tgcaattgct gcaacagttg agatttgct gtatggatgg        60 gataatgcta ctattgctgg ggctgtatta tatattaaga aagagttcaa cttggagagt      120
tctccaacct tggaagggtt aattgtggcc acatcaataa ttggagccac tcttattaca     180
```

```
acatgttctg gaccgattgc agatcgtctt ggtcgtcgcc ctatgatgat aatttcctca    240
gtttgtttct ttgttagtgc cttaataatg ttgtggtctc ccaatgttta tgttttactc    300
ttcggtcggc tattagatgg atttggaagt ggtttggcag tcactcttgg tcctctttat    360
atatcagaga ccgctccaac tgatataaga ggctcactga acacacttcc tcagtttact    420
ggttctggtg aatgttcct cgcatactgc atggttttcg gatgtcatt gatggaaaca      480
cctagctgga gattaatgct tgggattctt tttgttccat ctactgttta ttttctatta    540
actgtattct tcttacctga gtctcctcgc tggcttgtta gcaaaggacg gatgaatgag    600
gctaaaaagg ttcttcaatg gttgcgaggc agggaagatg tctttgctga gatggctctc    660
cttgttgagg gtcttagagt tggaggtgat acatcaatag aggaatactt gattgagcca    720
gatgctggac tcgctgagga tcaagatccg atgactgtca agatcaggt taggctgtat      780
gggtccgaag caggctgctc ctgggttgcc agaccagtca ctggtcagag tatgctgggt    840
attgcatctc ggcagggaag catgcagagt cctagtgttc ctttaatgga tccccttgta    900
actcttttg gtagtgtaca tgaaaagctt ccagaacaag gaagtatgct tagtgtcata     960
ttcccaactt tggtagtat gtttagtatg ggagggaaag agcccaaaaa tgaagagtgg    1020
gatgatgaaa atactattgg ggatgatgat gattatggtc atgacgatga agattatgca    1080
ggtgatgctg atgaagatga caatttacgt agttcactta tatctcgtca ggatacaggt    1140
ccagacaaag ccatggttgc tcctacttca ggtagcatgt tcagcatgaa gcatagtagt    1200
tggttacaag gaagcgaagc tagtggtatt ggtggtggtt ggcagttagc ttggaaatgg    1260
agcgagagag aaggcttgga tggtacgaag gaaggaggat tcaaaagact ttatctacat    1320
caggaaggtg atgctggatc taaacgaggc tctgttattt ctcttgctgg tggtgaggtt    1380
attggcgaca atgagtatgt gaaggctgct gcactagtaa gtcaacctgc cctttattcg    1440
agggatttca tggatcggga tagtattggt ccagctatgg ttcacccttc cgaggcttct    1500
gcaaaaaggc ctagttggag ggatttttta gagcctggtg tcaggcgtgc attagttgtt    1560
ggtgtcggac ttcaacttct tcaacagttc gctgggataa atggcgttct gtattatact    1620
cctcaaatac tagagcaagc tggggtgggt gatcttcttt cgcatatggg tataggcgct    1680
tcctctgcat tgttactcat cagtgcactc acaactcttt tgatgcttcc tgctatagct    1740
gttgcaatga ggcttatgga tctttctggg agaaggactt tgctactaac cacaattccg    1800
gtgttgttct tatcgctcgt tgtcttaata ctcgcaaatg tcataaagat gaacaccact    1860
gtgtatgcag tggtctccac agtcgcggta gttctctact tctgcttctt tgtgatgggg    1920
tttgggccta tcccaaatat cctatgtgca gaaattttcc caaccaagat tcgtggagtc    1980
tgtattgcta tttgtgcact tactttctgg atctgtgata tcatagtcac ctacacactc    2040
cctatgatgc ttaaagctgt tggacttgct ggtctctttg gcttctatgc tgttgtgatt    2100
ttaattgcat ggatatttat attttttgaag gttcctgaaa ccaagggcat gccccttgag    2160
gtaatcactg agttctttgc tctcggtgca agacaagcaa gccactga                2208
```

<210> SEQ ID NO 3
<211> LENGTH: 735
<212> TYPE: PRT
<213> ORGANISM: Beta vulgaris

<400> SEQUENCE: 3

Met Ser Ala Ala Val Leu Val Ala Ile Ala Ala Thr Val Gly Asp Leu
1               5                   10                  15

```
Leu Tyr Gly Trp Asp Asn Ala Thr Ile Ala Gly Ala Val Leu Tyr Ile
            20                  25                  30

Lys Lys Glu Phe Asn Leu Glu Ser Ser Pro Thr Leu Glu Gly Leu Ile
            35                  40                  45

Val Ala Thr Ser Ile Ile Gly Ala Thr Leu Ile Thr Thr Cys Ser Gly
 50                  55                  60

Pro Ile Ala Asp Arg Leu Gly Arg Arg Pro Met Met Ile Ile Ser Ser
 65                  70                  75                  80

Val Cys Phe Phe Val Ser Ala Leu Ile Met Leu Trp Ser Pro Asn Val
                 85                  90                  95

Tyr Val Leu Leu Phe Gly Arg Leu Leu Asp Gly Phe Gly Ser Gly Leu
                100                 105                 110

Ala Val Thr Leu Gly Pro Leu Tyr Ile Ser Glu Thr Ala Pro Thr Asp
            115                 120                 125

Ile Arg Gly Ser Leu Asn Thr Leu Pro Gln Phe Thr Gly Ser Gly Gly
130                 135                 140

Met Phe Leu Ala Tyr Cys Met Val Phe Gly Met Ser Leu Met Glu Thr
145                 150                 155                 160

Pro Ser Trp Arg Leu Met Leu Gly Ile Leu Phe Val Pro Ser Thr Val
                165                 170                 175

Tyr Phe Leu Leu Thr Val Phe Phe Leu Pro Glu Ser Pro Arg Trp Leu
                180                 185                 190

Val Ser Lys Gly Arg Met Asn Glu Ala Lys Lys Val Leu Gln Trp Leu
            195                 200                 205

Arg Gly Arg Glu Asp Val Phe Ala Glu Met Ala Leu Leu Val Glu Gly
            210                 215                 220

Leu Arg Val Gly Gly Asp Thr Ser Ile Glu Glu Tyr Leu Ile Glu Pro
225                 230                 235                 240

Asp Ala Gly Leu Ala Glu Asp Gln Asp Pro Met Thr Val Lys Asp Gln
                245                 250                 255

Val Arg Leu Tyr Gly Ser Glu Ala Gly Cys Ser Trp Val Ala Arg Pro
            260                 265                 270

Val Thr Gly Gln Ser Met Leu Gly Ile Ala Ser Arg Gln Gly Ser Met
            275                 280                 285

Gln Ser Pro Ser Val Pro Leu Met Asp Pro Leu Val Thr Leu Phe Gly
            290                 295                 300

Ser Val His Glu Lys Leu Pro Glu Gln Gly Ser Met Leu Ser Val Ile
305                 310                 315                 320

Phe Pro Thr Phe Gly Ser Met Phe Ser Met Gly Gly Lys Glu Pro Lys
                325                 330                 335

Asn Glu Glu Trp Asp Asp Glu Asn Thr Ile Gly Asp Asp Asp Asp Tyr
            340                 345                 350

Gly His Asp Asp Glu Asp Tyr Ala Gly Asp Ala Asp Glu Asp Asp Asn
            355                 360                 365

Leu Arg Ser Ser Leu Ile Ser Arg Gln Asp Thr Gly Pro Asp Lys Ala
            370                 375                 380

Met Val Ala Pro Thr Ser Gly Ser Met Phe Ser Met Lys His Ser Ser
385                 390                 395                 400

Trp Leu Gln Gly Ser Glu Ala Ser Gly Ile Gly Gly Trp Gln Leu
                405                 410                 415

Ala Trp Lys Trp Ser Glu Arg Glu Gly Leu Asp Gly Thr Lys Glu Gly
            420                 425                 430
```

```
Gly Phe Lys Arg Leu Tyr Leu His Gln Glu Gly Asp Ala Gly Ser Lys
                435                 440                 445

Arg Gly Ser Val Ile Ser Leu Ala Gly Gly Glu Val Ile Gly Asp Asn
        450                 455                 460

Glu Tyr Val Lys Ala Ala Ala Leu Val Ser Gln Pro Ala Leu Tyr Ser
465                 470                 475                 480

Arg Asp Phe Met Asp Arg Asp Ser Ile Gly Pro Ala Met Val His Pro
                485                 490                 495

Ser Glu Ala Ser Ala Lys Arg Pro Ser Trp Arg Asp Phe Leu Glu Pro
            500                 505                 510

Gly Val Arg Arg Ala Leu Val Val Gly Val Gly Leu Gln Leu Leu Gln
                515                 520                 525

Gln Phe Ala Gly Ile Asn Gly Val Leu Tyr Tyr Thr Pro Gln Ile Leu
        530                 535                 540

Glu Gln Ala Gly Val Gly Asp Leu Leu Ser His Met Gly Ile Gly Ala
545                 550                 555                 560

Ser Ser Ala Leu Leu Leu Ile Ser Ala Leu Thr Thr Leu Leu Met Leu
                565                 570                 575

Pro Ala Ile Ala Val Ala Met Arg Leu Met Asp Leu Ser Gly Arg Arg
            580                 585                 590

Thr Leu Leu Leu Thr Thr Ile Pro Val Leu Phe Leu Ser Leu Val Val
                595                 600                 605

Leu Ile Leu Ala Asn Val Ile Lys Met Asn Thr Thr Val Tyr Ala Val
            610                 615                 620

Val Ser Thr Val Ala Val Val Leu Tyr Phe Cys Phe Val Met Gly
625                 630                 635                 640

Phe Gly Pro Ile Pro Asn Ile Leu Cys Ala Glu Ile Phe Pro Thr Lys
                645                 650                 655

Ile Arg Gly Val Cys Ile Ala Ile Cys Ala Leu Thr Phe Trp Ile Cys
            660                 665                 670

Asp Ile Ile Val Thr Tyr Thr Leu Pro Met Met Leu Lys Ala Val Gly
                675                 680                 685

Leu Ala Gly Leu Phe Gly Phe Tyr Ala Val Val Ile Leu Ile Ala Trp
        690                 695                 700

Ile Phe Ile Phe Leu Lys Val Pro Glu Thr Lys Gly Met Pro Leu Glu
705                 710                 715                 720

Val Ile Thr Glu Phe Phe Ala Leu Gly Ala Arg Gln Ala Ser His
                725                 730                 735

<210> SEQ ID NO 4
<211> LENGTH: 35272
<212> TYPE: DNA
<213> ORGANISM: Beta vulgaris
<220> FEATURE:
<221> NAME/KEY: modified_base
<222> LOCATION: (25997)..(26718)
<223> OTHER INFORMATION: a, c, g, or t

<400> SEQUENCE: 4
cactaaaaaa aaaaaaaaaa aaaaatttag ttgaacctct acgccacctt caaaattctt      60
tgccaccttt ttctctctct tcactctccc actccacatt ccaaaaccc aaaaaaaaaa     120 atatgacagg ccaggaccaa aataaaacag agatcaccag agaaacaatt acaaaacccc    180
gacgacaaac ccactcaagc cgtcaacctc gtcccacaac ccgaccacca ccacctcgtc    240
ctccacaacc tcctccaacc cggcccgccc gagtcccact aaaaaagctc ttaaaagtaa    300
```

```
catccgttgc aggtggcata caattcggtt gggccttaca actctctctc ctaactcctt    360
acgttcaaga gttaggcatc cctcatgctt ttgctagtat catttggctt tgtggtcctg    420
tctctggttt catcgtccag cctttagtcg gccatattag tgaccgctct actagtcgct    480
atggccgtcg tcgccctttt attcttgctg gtgctgccat gatcattgct gctgtttcaa    540
ttgttggatt ctccgctgat attgggtttt tgatggggga taaagttgat ggaggagaga    600
gaaaacgacc gatggcgatt gttgtttttg ttattggctt ttggttgctt gatgttgcta    660
ataatactac tcaaggtcct tgtagagctt tgcttgctga tcttactggt atgtttgctt    720
ctcaattttg tattaattat tagtgttgga aatgcgacta agcctaatga tgtaggtagt    780
tgatgagatt cgatttcaag tctttagtac taatcttacc cgttagtgct cgttcgatat    840
gattatcggt ttttagtttt tgattttatg aatacaaaag tcatatgaaa atatattatt    900
tactatttta taatatttta aaataagtga atatatctc aaaatagaaa aaagtgataa     960
aatgataaga gtaggcataa atttgtgtaa tttgtttttc tcttctcctt ttaatcatga   1020
aaaggatatt ttgtgatttt taactttcgg gagtgatgtt tattaaattt tgcactccat   1080
catttactcc ctccgtcctt tattagttta ctttttttaa tcatcaaaag gaatagtatt   1140
gtggagcgta gaaagagaga gaaaagatta tttatacttt aaagttaaat atatgtgtga   1200
tgaaaagttt gtactctcat ctcaaaaata tcaaaaaaaa aaagaaagac aggggtaaac   1260
taataaggga catccttaaa agaaatacag gtaaactaat agagaataaa gggagtatta   1320
tggaacaaag aatgtgtgtc aattttaaaa ctgacaatag aaaaccgaaa attatcttct   1380
tttttatttt tatattttgt ttttgctttc taaaaaattg aaaattaaaa taaaaaacga   1440
taatgaatga gcttatgtta gatgattttt atttgttttg cggttgttga ttgattgctt   1500
ttctagggtt ttgttgatat tttgggatg caaaagaaa aaggaaagtg tgagtgagag    1560
aatgctgtgt tggtttatgc cggtttgggt gtcagcctat cagaggggag ggaggtggcg   1620
gggaacgtta cttttttgc attttttaat tttttaataa aatgtttaaa aaataagata   1680
aaaatgaaaa tatattgtga aagagacaaa gagccaagag gatttgcttt attagttggt   1740
aggacggttt tgcccctatc tctaattgag gctgacatct tggagtgaat ttacttgtct   1800
aatttatttt tattttcaa aattgattta ataattcttt ttaggggtaa tttgatttaa    1860
ttagtgtagt gtgtctctcg cttgttaatt ttaaattaat atttattgat taattggaaa   1920
ttatacaaca ttataataga tgtcaatgat gaaaacatat tcaacttgga ccataaataa   1980
ttcttaaaag cctctagggg aggaaaaaat caaaactttt ttaatttatt aggattagtt   2040
tatgtccgtg ctatgcgcaa gtatctaaac aaaggaaaat aggaataaaa taaaggaaag   2100
atttaccaaa cattgattta tgtgactaca taattaatct aaaaatgttt ttctattata   2160
atattatatt tagttctcaa aatagtaata cctcttttgg aaaaaagatg tgtatgatta   2220
tcataatatg aatgactgag atggtgcgag actaataatt tttgttgatc acaagtataa   2280
atcttattaa ttataccaat ttttatcaaa ttttaatttt tttaaaata gtttccaaa     2340 gcttaacaaa tgaacagata acattaccaa ttaaatttga atggttcatt cccctcaaaa   2400 taatttttt tgaatggtt cattcccctc aaaaaaaaaa tatttgaatg gttcaaactt     2460
tgaatagtta caatggctac aattttttt ttttgctaag tcattaagag ttacatttca    2520
agcccaaact ttacaaccta caccaagaga actaattata atcaagagta aactctctta   2580
gggaatgttc ggcaaaagta actgttaggt agctgttggc tgttggagta gctgtcagct   2640
gttagctgtc ggctagtagc tgttagctct tagctgtaaa agtagctgtt tacaatataa   2700
```

```
gtgttcggta aaagtagctg ttatgcttat atatgataaa aataacatat tttttaatta    2760
taatattaat tataattata tgattaatta ctatatggtt catactaaga tgacagtgtc    2820
ctcatcagtc cacttaaata cctcattcgt tccttctttg ttattagatg aagtcatcta    2880
cgtatctaac ataaccatga ataatataaa aatattaatg agaatataat gcaccaagcc    2940
atctacgtat cttgcagcca tattagtata ctaatcaacg ttaaaaaata taagccgaac    3000
gaaaacaaga gagttagttg ataaaaaaat ttatctttga taaaaatgag aaagtgggat    3060
ttttccctaa aaagaaagtg ggattttta tccttaaaga gtgggatttt tttctgttaa    3120
tctgaaattt ttatcctgaa tatatgatat tttattaatc ccaaatttta atccttaaat    3180
agtggaattt tttcctttga aaaaaaaat aaaaaaaata gaaagctact tacagaaact    3240
gaacgctata aaatacttat aacgtttggg aaaagctatc caaaagcttt gaaactccaa    3300
tagctactcc aacctctact atgccaaaca cttaattagt gttttgactt agtcaaaaca    3360
ctaaaagcta gtgcaaaagc tattgccgaa caggtcctta atcacattct atcacttcta    3420
gagactttt tttggcacaa cacatagatt ctatacatgt ttatacagca ttgctagttt    3480
actattccat agaacatcat tcctggccca ccatatctga taggcagtag cacaaatcac    3540
aacacttttc acttgtcgcc tgaatttgta acctccactg ttgttcacca tcaagatcaa    3600
tccttgaatt gatctatcct gacagctcaa attcagccat ctcacacagc tcctaattac    3660
aaccttactg aaagggcatg aaaaaaataa gtgattgtga gtctctcttt cattcccaca    3720
caacagacaa gcaggatcat caatcactcc cacattgttt aatctatcag ctgtgttcaa    3780
tctgtccaac atcatcaacc accacaagaa tctgtgcttt ggtacattaa ttctactcca    3840
tacaaatcca tgccaaggaa cagcaggatg aacttcaatc atcttttgt aaacatcgtg    3900
aatagagtac tctgtcatgt tagtgatctg ctgaaaagag aacttcatct tcatttgatc    3960
tttagctagg catactattt tccaatacca gctgcagtgt tgaggtggtt tatattccca    4020
ccactcttcc tctttaacat aaacttcatg gccccatctt atccagaggt tgtcttttt    4080
tgtagcaata gcccaaacat atcttcctag agcagcttga ttccatacca tagtgtctct    4140
cacacccaga cctccctctc ctttagtgct atggactttc ttccacttca catttccaac    4200
tttctgactg taatactcac cactccactg ataagctctg caaatttat taacgtcttc    4260
aaaatttcc ttggcacaat caagatttgt gcccagtgta catgtaaact catcaaaact    4320
gagtttagca agcaaagcct tccttgataa gacagatgcc tactgctcca gcatctgatt    4380
ctagcaatca tttttcaat caggctatca caatctttag cacttatcct cttatgacaa    4440
atgggaatcc catatctcaa aggaaattta cccaagctga atccaaacac attcaataat    4500
ctttgtactt cctgctgctc gactgactcc tactgtgtac atttcagttt tctgcttatt    4560
agctgtcttc gagaagtgtg caaacccttg caacatacat agtacagatt tgaaatcacc    4620
tttactgcac gtgataatat catcacgaaa acataggtga tttaatttga ccccagtgca    4680
tcttggatgg aatttgaaat catctctctc tccaactctc ttcatggttc tgcgataata    4740
ctccatacat atcagttatc acaaataaca aggagagag agggtctcct tgtctaagaa    4800
ccctcttccc cttgaaaaaa cccactaatg acccattaat catcaaagag aaattgagag    4860
ttttacaca ttccatcacc atctctacaa aattttcagc aaacttcaaa gcatttagta    4920
gatcttcaat gaaacaccaa tcaagtggat gatatgtttt tttcagatcc atcttcataa    4980
tgcatccagg ggaagttcct ttcttcccat aagttttgac aatatcttga catatcaaga    5040
```

```
taatatgagc aatgaatcca ccctttatga aagcaccctg atttgcagca atgatctcag    5100
ggagaacttg actcagtcta aagcataata gcttagtaat gcatttataa actatgttgc    5160
acggaaacgg gtatggggat ggaaaacggc aaaatcaaaa ttgcaaaaaa ctggtacggc    5220
atggattcgg caaaaaaaaa aaatttaact aaattaaaca tccatacata aatagttcaa    5280
agttaaaaat actttaaaac aacaattaaa tttaatgtct taaagtagat aaagcttaga    5340
taaggcaaca ccgcaacaca tcaatcttca aggagcaact cattttctga atccggttca    5400
tctagtgaaa gttccgctac atcctccaat gaatcaaatg catctccacc aatatcccac    5460
atctttgtat aaagctccta atattctttg gaattccttg ataaaaggcg aagatagttg    5520
tggatgaaaa ccaaatcttg tgcacgactt ggatttagct tgttcctcct aagtgagtga    5580
atgaaggaat atgtactcta atttctctca ctacaagatg atgaagtagg ttgcccgagc    5640
actttaaatg ccaaagattg gaggagagga gtttgagctc caaagtttgc ccaccaactc    5700
ttaggatcca tagaatgcat ccttaaaata caagttaagt cctcaaaagg tccactcttc    5760
atagagaata gtgcatattc atccattact ttaccaacat catcactaag tgcaaataat    5820
ctacgaaagc acttcatcct ctctcgagat acttcaccat ctctatgagg agcaactcta    5880
gatggagctc caagtagcca ttcatcatta tagaaccttc aatattttt aaaaaaagga    5940 ttataagttt gtgtataaat ataataagat agaaagaata tcaaagaata tatacctcgg    6000
gttcaaggag tgggataaac aatggagatg agtgttgctt tttgcccaac gagctactaa    6060
gatttcataa accacatgaa aaaagggact aaactccgga tgaggacgac attctttctt    6120
gtaaatctca agcttcactt gttcaatcat agaatcccac aacactaagt taaggcatgg    6180
tttctcggtg tcacaatgcc taatcatgtc atagataaac cttgtgaaat caacaatgta    6240
agatagtttg tcccaccaat catcattcac aatcttctcc ttcaccaagt ttgccttccc    6300
tatgtcttct tctctataag aagtccactc atcacttata accatggctt gaagacctcg    6360
tttgatgagc ttaaatctct taagcatcac aataatggag gcaaagcgag tatcggccac    6420
ggaaagcaac ttaagaggag aaaacatctg gaacatggcc aatctcatgt tgtggttcat    6480
gatgaaattt tcaatttgaa agtcatcccc atggatttca gtgatcaaac tacattcttc    6540
ataagtttca tgattactat tcacattcct tgctgcacaa atgttcttca aagcaagatt    6600
aagcgtatga ataacacatg gtgtccaata aatgtgagga aactcactct caatgagctc    6660
tctcgcccct ttgcaatttg ctgcattgtc agttatgatt tgcacaacat ttgatggcc    6720 tacttcttga atgacttctt tcataagatt agcaataaaa tacttatctt tcacttcacc    6780
aaaacaattc acagctttaa gaaagattga accattacca gaagtagcca tgaaattaat    6840
gagaggtttt cttgttagat tactccatcc atccgtcaca attgttactc cttttttctct    6900 ccaagttgat ttcactggta tcattagcct ctctacatta gcttttctt gtacaagcaa    6960 tgtagttcta agcttgttgt aaccaggggg tttgtaacat gctatattat aggtggcagt    7020
aaaagtaaaa tccctcatat agcgtggatt tctaccaaga ttaaatggca accctcctgt    7080
gtaaaacatc cttgtaattt cttggattaa ttgatcccta ctttcaatcc caaacatct    7140 agtaataggt gatttatcag acttcctttt cttgaatgta gcattggagt ccaaatgaga    7200
aagagattca ctaggcaaag gaacttccct agggcccgaa tcaagtttct tattctcaaa    7260
ttcatcatcg tttttgcatt tcaagtttat caatacgaga cactttctta caacatgcaa    7320
ttccttgacc cttaatttga agcaaaggga ctctaactct agaataacta gatgttcgat    7380
tttcattaca aaaattacat cgatatttgc atgttccacc aaccgcccct tgttttttcaa    7440
```

```
gtcttgttac aaacatccac aatggaggaa aaccctcact ttgcgttgat tcgacgctaa    7500
tggacccaga ctcagaccca ctatccgtgc tgctaccaat attagtactt tattgttgag    7560
attgggatgt catattttc ctaataaaca cattcaacac aacaatcaac aattcaacaa     7620
cacaacaatt caacagaaca caacaacaat tcaactttca acattgaagt aaactaaata   7680
atctaataac actaattcac tagacactaa cttactgcct ttcttcctaa aaaaaaaacc    7740
aaacaaaaac agaaaaaatg aaaataaaaa gcaagaaaaa cagacccaac attttacatg    7800
cgaaaagttg aaaccctaga atccgaaagt agagagaagc tcacctaggc tagtgagaga    7860
agaaatcagg caagttgagc taccaaggag aagaaaaccg atgacttacg agtcgagctt    7920
ccaagagaag aaccagcgaa gaaaaccacg aagaaaagag aataaacgag tcgagaagaa    7980
accgacggcg aggcgacgaa gcacttcgca gttcatatga gtagtagaga gaatttggga    8040
atttcgaaaa tctaaaaccc taaaaaaatg aatttgggcc tctcaaagtt cattaaacaa    8100
gtgggtacgt ggctcctttc taaaaagcgt ccccagcccg tcccaaaatc ttcagccggg    8160
gtcaaaggaa ccatgagggc attcctatga tcctcattca acacaggaac acaggacctg    8220
ctagaaccac ttcttgctgt attgtgcttc tactttctct agaagtaccc aggggactat    8280
gtaatactgt aaaaaagcct tgttcacctc ttcaacactt tcaacccatt gaccattcat    8340
atctgctatc ccatagacac tattttgcaa tcttctagct ttaatagcat tatggaacat    8400
ctttgagttc tcatctcgtg atttaaccca ggcgagttta ctcttgtgct aaagaaaaga    8460
tcatattttg aatgcacctg tttatactcc agagctaact tctactcaag atcactagct    8520
tgaatgctag taggatttag ttgcagtgca ttctgagcat ctttcatggc tatactagcc    8580
ttagtatcac atatatgaat ttgagaaaaa ccttctctat tcatctcttt ttttacatgt    8640
gtttcactag cttcagcttt tgcacaaact taaacgtggc acattcattt atattcacac    8700
tccagactct ctacccttc gctttgaatt cttccaccat actccacata tgaaagtatt     8760
tgaagggagt tttgttgctt gtgaccccct catgaactcc tggtgtatga taaaaaatcc    8820
cctcattcac aaacatggct tcagctgtag ggaacttgtc agtccatttc tcatttccca    8880
taactctatc caattttgag aaaactttgt cacttgcttg ctgtttgtta ttccatgtgt    8940
aataacagcc attggattta atgtcatcca atccacatta gtaacacat cttcgaaaag     9000 agatcatttc attatctcta atagtagaac ccacccttc ctctttattc aaaacacagt     9060
taaaatcacc tcctaccatc caaggaacat ccatattgtc tgctatttcc atcaactcaa    9120
cccacactct gagtatgtct ctatctcctg cattattaaa tgcatatata aaagaacagc    9180
agaacccatc tatagcccca gcaggcttta caaagcagtg aattagttga agcagtttat    9240
tagttgagca ctaatccatc taatatccac ctgaaaactc agtggagtcc aagataaagt    9300
tagtcttcca ccagaatgaa aggaggaatt ggaatagaaa caccaacctg caaacaagtt    9360
ttgatacatc ttaccatat ttttggcttt caccttagtc tcaatgagac taaccattcc     9420
aagggatctt atattaatca tcttctttac ttccttctgc ttcatcaagc tgtttatccc    9480
ctgaacattc cagatcaaaa tactatccat ttgcctcagg aggggggcgc cctctccttt    9540
atctgcctca catggcactg tccctaccat cacttggtct tctatgattt cattcaaaac    9600
cgtgaaggaa ttattgacac tgacgggacc agcaggctgt atacttcttc ttgctgattg    9660
agtaaccctc tgaaattctg tttcagcttc attcattact tccctttgca ccactggttg    9720
cactctaacc tcctttgcct tccaaacttg cctcttcact cctctattac acacctttgc    9780
```

```
cacatggccc attttcttac acacagaact cgtttccatt cataagacac atcaattaca    9840
acctcttcac cattctcatt aataaaactt agttgatcag atgaatttta acctcaacca    9900
tcacacgagc atactgtaac ttctccctct ttgctgttgc tgtatcaacc ttaacaaact    9960
tccctagaga gctcaccaat ttgtttaagc acctctcact ccagtattta aaatctaatc   10020
gcagctgtat ccaagtagga atgaaatcaa attggtcctt cgtaacatcc atgtcctgtt   10080
cccatgctct cacaatcacc ggtttattgt caaagaaagg aacagaacca gtcaagacat   10140
agtccttctt ttccattgac aaaaaacgca ctatataaac tccattcttc aacaatgcta   10200
ctttatccac tccattgttt ttccaaattc ttctaataaa accttccata acatatggag   10260
gaggactagc cccaacgaca tagaaaataa tagaggaatt ccaaaaatct acttcagatt   10320
gtacatcttc taaatcaatt ttaaccagat ttttcacatt acagacatta tcaccataac   10380
cagatggatc agaatctacc tcattatcag acatttgcaa aattggaatc ggattaactc   10440
tacgcatact cctatcagca actacacttc tctttacagt attcctcaga ggtgtgaaca   10500
gctcataacc actccgagaa cattctatga gattgcatag attgctgcac tgctcgaatt   10560
tcttcctcag ttttttcctc caattgaaaa tccatagcat tgacaccaag gtttcatcca   10620
tcgatcttgt cttctttgca tttgaatcag atactggatc ttttggtttt tgattgctag   10680
aattaacttg gactttagaa ttcctcgcca tggcagaggg aattctagag agagaaacac   10740
tctagttatc gtactttcgc agtgctagaa atttattgta ggcatgtaga atctttcaga   10800
aaatacataa gtgagaacat aacattactt tttatacaaa gtacaaaact agaacctaaa   10860
acttatatgg atgtttttct tttatattag actttatttg aatccattac gttaccggag   10920
aatttcattt attagcttta gtccacaatc tgtaatatat attatatatt ggcactttt    10980 taagagtgat ttaacatgtc tgttaatagt aatcgaaaag aaattattgt gtaaataatg   11040
tggtggctca ccctcaaaac tattaattat cgctctaatt ggtttaaagt acatcttgat   11100
taattaataa gcaacaattt ctttgccgaa gtctaccact cttgacaatt gttctttaaa   11160
ggccaatgga ttatttcaac tttagccatt taaaagcacc tcaacaaatt tgtgatcttg   11220
cgtagagaat gaatagaaca actattaata taatttgttc aatgttgtca catgcaacgt   11280
tatcttagta agtgttgcta tttgttgatt actcgatgga gatgcgccac aaaattgatc   11340
tcttcatgga gaaaaataaa tcatagaagg tgctgggtag agcaatcgtt gatgtcccaa   11400
aggacaagag gtccaagctt aatagaaaaa ccaaaatatg tatctttgtt ggctatccac   11460
aagatgagtg caattataag ttatcatgtt tgatggacta cagaaaactt attcgaagta   11520
gacgcgtttc cttttctga agaccaaacc gttggataat ttacaaaagg tgaataatgt   11580
ttaattaaga atcgacaaaa tccatttgct attctagatg tgattatgtt aatgagagag   11640
aagtaaacac aatttaatat attggtgatg atgataatag taagcaagag gaacacatca   11700
caaattaatg aagcattgac actagggtta agaagattca ctagagataa acgacttcca   11760
tgaagattac ttagaggtgt atcaattgat aatagaagga gaagagctat gttatagtgg   11820
atgtgaaaaa gaacaaataa tgaacacaaa aaataataaa gaacacaaag atttaatgtg   11880
gttcaccacc atagtgttgg ctatgtccac gagcagaacg agagagcgag agaacagaag   11940
atcttccttg gagaggattt gcatccctat ctcactcata tgcccaagtc ttatgttcca   12000
tagctttgtt atctcctcct tcagaattta aggtgaagca acaacaaccg agcttgaaag   12060
agtagaacct tgcaaaacgt acaaagtgcc acattgactc cctcaacaca tcctttgaac   12120
ctttgatgac ctacacaact tcaccccca ctctgaaact gaacccctta ttgtctaaca   12180
```

```
tactaagcga aatcaatttc ttggtcatct atggaacatg cctaagattc ttcaatgtgc   12240
agaatatacc atcatgtggc cgaatcttaa tagagccaat tccaactgtc ttggagaatg   12300
cactcttagc tattgaaata ttaccccccat ctaccttctc ataagtagta aaccactccc   12360
tacgaggact catatgatac gatgctccag aatctaaaat cacttatcag tgcaatgtgt   12420
ttggtcatta gcaactaaag caagaccatc cttagaattc gaattttgtg ttgcaacagc   12480
agcagaacta gaccagattt attttcctga tgcttttttct taggacattc cttcttccaa   12540
tgcctcttct ccttacaaga tataattagg tttaggaccc tctttaaaat ttccgaatat   12600
tctgaaattc ttttttgtcag aattttcatg tcatttatta ctactggcca ctaatctaga   12660
agcttgatca tatataccta tactaccaga tgccttatgg cgtaattccc tagtatgaag   12720
agatgatcta atctgttata gggacacaaa atctatacca ataataaaat attgcacaaa   12780
attctcatat gacaatggta aagaaacaag tagaattaaa gcataattct cattctccac   12840
cttaacatca atattacgca tttctaacga aaacatattt aattgattta ggtgatctct   12900
aagaggtgta ccttcattca tgcgctgacg ttgcttcaaa agcaacttgt tggctagaga   12960
ttttatcatg tacaaactct caaattttaa tcacagacca gatgtggttt cctcctctgc   13020
gacttcagtg atgatgtcgt tagcaagaca caacataatc gttaaatgtg ccttctcctc   13080
cagaacgacc atctcaacgt taactgaatc cgatgacttc tttgccaacg atgcccacaa   13140
tccttgttgc ttccatcttg atttgccaca aactgaaact ctatctccca gtgaatttat   13200
cgagtttcac attcatccta gacctgtttc ccattcagat cagaaaccaa agctctaata   13260
ccaatttgtt ataattataa cggatgtgag aaaaaaaaca ctaaacacat aaaataataa   13320
agaacacaga tttaatttgg ttcaccaaga gagtgttggc tacgtccatg ggtatagaga   13380
gagaagtttt tttctctctt taggaattga tgtgtttctc gcactaatga aaacttaaaa   13440
caatatagaa ataacatatt ataacccaac tcaaaatcgc ctactcgcgt caaaataccc   13500
accgctagat cgggcggtca atttccccaa acctaaattc ttctcgagcc cgatggggcg   13560
ctggtcgtcc ggtcgtgatt cggtgatcac gcctgatcgg acgaacccgt cgagctcatc   13620
gggcggcctg cttctaaggc ccgtgctaag actttctcct tgcccgatcg ggtggcattg   13680
cccaacttga tcgggctgcg acatctccct ttgacgagat tcaagtccta gaagctagaa   13740
tcctatgaag aggtttattt ttgagaaaga agatgaaatc catgcaacct gatatatgat   13800
tattgcatga taaccacgca tctgatttgg tagaactagg aaagaaataa agcaaggcta   13860
gctctgaagg ggtttagtta aaagaaggga attggctttg aagaagtctt ttctcttggg   13920
tgaaaatgtc ctcaacccga tttgtccttg gcatggaagc atatattgat ttagaaattg   13980
aagacatgaa aataatttac atctaagaat ttcaggtgga tggtgtgtcg gttatattag   14040
agcttttgta agaaagtttc acgacttttg tacaaaaagt acaaatataa tactatatga   14100
aggattatga ttatcaaaga caacatcata ccactttgtg gttgatttgt agtgggagat   14160
ttttattaat tttctccttt atgttgatga tatgttaatc attcttctaa tttgaagaag   14220
gtgatgaaca agttgttttc catgaaggac ttagggtata cagattcttg acatgaatat   14280
ctcccatgac acgaagaaac ggctatggtt gtcagaggaa agatatatgt ctattctcca   14340
cttgtaggcc atttttaagtt tagttctaag taatgtccga caagtgagaa tgaaagagaa   14400
gaaataaggg aagtccctta tgctagtgta cattgttgtt tagtgttact atgacctcgt   14460
atagcctatt tagtaggtga tttaagtagg tgaatagagg gaaaccatca ttgggaagat   14520
```

```
ctgaaatgga tttatatgta tctttatagg acatatgaaa tgggtctgtg ctttggttaa    14580
ggagaacctc tctaattagg atacataatt accagacatg tggacatggc aaagcatgtc    14640
agattaaagg atgatttaag tgatgaccat ttagtaggtg attctagtaa gtgatgactt    14700
ttgtagtgaa agctctatca tggcttctaa aatatgttgc tttataaaat aaaaaatacg    14760
actatattgt tgtagtacga gcttgcaaaa cagttgtttt agatgaagac tttcctacaa    14820
gagttaggta ttaagcaaaa aaaaattgca ttattgtgat aagtaaagtt ctagtcacct    14880
tgctggaaat actacttttc atcttcgttt gaacttcgat atttgaggta tcattaaaca    14940
tgagaagttt gtgaagacaa gctattgcag ttgaataata ttctcatgat cacaatggtt    15000
catatatgat tattaagaca ttgaccatgc aaaagcttga tgtgtgccga gaaatagcaa    15060
tatcatcatg gattccttaa tatgtcgtca ggggaaaatc tgttggtatc cgttctttt    15120 tacttggata caaggagaac gaagaactaa aactaaagag agtaaggatc agaatcggga    15180
gatgggaagg aaattgagag taaatgaat tgagaaatgt aaacaatgtg cacaattgtt    15240
tttttctttt cttaatttgt tctcttcttt tggtttaaag gattcttttg aaatttaaca    15300
attcattact taataataca catcatatat atgttgtaat cccctcaaaa aaaaaaatat    15360
atatgttgta atcatttagt gataggaatt tcaaattata ttacaaaact agagatatga    15420
agcatggatc aatagagtta agaagattca ctagagataa acgacttcca tgaagattac    15480
ttagaggtga gtatcaattg ctaattgaag gagaagagct atcttatagc ggatgtgaaa    15540
aagaacaaat aatgaacaca aaaaacaata aagaacacac agatttaacg tggttcacca    15600
atgtagtgtt ggctacgtcc acgggctgag agagagaaaa gaagatcttc cttggagagg    15660
atttgcatcc ctatctcact catatgccaa gtctcatgtg ccatagcttt gcctaggggg    15720
tgcccatgtg cttcctagac aacacttccc ctaaagaggc ttatttgtga gaagcctcgt    15780
atgccgattg aacacacata ttggagtaac ataataatgg gctgtttggg ccgaaaacaa    15840
gcttcaattg ggctcaaact ttggggtcca tattttgggc ctctcaagat aatggtcagg    15900
ccacattttg gatttctagg agatggtgcc tggccatttt ctgtggtgca cctgaaggat    15960
ctaaaagatg cttttatatt cttgtatgta ttttcgtgga aaactctagg ctagggagtc    16020
tctagaattt atctagatta gtcttttgta cacaagtgtc cagaatgtac taggcggtag    16080
agagcttaag ttgtttgtag gatttatgtt tttttttttt ttaacttcta ctaaacagaa    16140
aatattctat gcatcctata tgtatccatg tggcgcaatg agctaccgc taaccaatca    16200 agttattata caatcttctt tttatttaat taaagtccct aaccccccc ccccctacc    16260 tacctctccg gttttgtgag agcttggcgt tgacatgtgg tgtaagtgta actgctacat    16320
ggaaaaactt ctgctcatat attaaaagcc ttgtaatagt tctgattttt aatctgttca    16380
agagagagca agagacaggt ttagatgtca ttatctatgt agaagtagat tagttttcct    16440
taaaaatatt atttcttgtg tcaggcaagg atcatagaag gaacagagta gcaaatgcat    16500
actactcttt gtatatggct attggcaaca tccttggctt tgccacagga tcatacacta    16560
gctggtacac tattcttcca ttcactcgca ctcatgcttg cagtgaaagt tgtgccaatc    16620
tcaagtcagc tttcctcatc gacattatat ttatagtaat aacaacgtat ataagtatca    16680
cagctgctca tgaagttcct ttgaataccg aggatggagg cactggcata tcagaaggat    16740
ctcagccatc tggccatgct gaggaagcct tcttttggga actatttgga acttttagat    16800
atctacctgg acctgtttgg attatccttt cggttactgc actgacttgg attgggtggt    16860
ttccattcct actctttgac actgactgga tgggtcggga agtttatggt ggtgatccag    16920
```

```
atgaagggca aatctaccat agaggagtca gtacaggtgc tcttggcctg atgtcgcaat   16980
cagttgttct gggtataact tcattgttga tggagaagct ctgcaagaag ttgggttctg   17040
ggattttgtg gggcatctca aacattatta tgtctttgtg ttttgttgca atgcttgtca   17100
tcgcttttgt actgagcaag gcagactcct ttggttccgg gagtcctcct aatggtgctg   17160
ttattgctgc agtgattgtt ttcacgattc tcggtatgcc attggcggta agtaactctc   17220
aatctttata tgatcaaatg agaagacgct taaaagtaga gaagtaagaa caatttgtgt   17280
ggattttttt cgtggctatg tgcattcttt tagagtatac acagttcttt aaaactaatg   17340
aataaatgca ttcttttga atagaatgtg catatctttt ttgtggattt tttattttat   17400
ttttaccttg tccttctatc ccccccttt ctctctctct ttttgaagt ggaatcgcta   17460
cttttttgtct ttagttttct tcagtgcctt ctcatatatg gtactcaggt aaacataatg   17520
aatgatctaa ttctagattt aacaatagaa atagaacact ttattataat caggtgttgc   17580
actaggatac gtttgctgaa ttagctggtg aacatggttt gtgataaatt tttatggtga   17640
aggggctaca attttctctt taatttgcta aaaattgtaa tgaatcaacc taggaagagg   17700
ggtacttttg gtattataat aattagttag attttagtag tagcttgaag aataagctag   17760
ggagttaggg agtaaatatc tctataaata gaatggaata gggagagaga aagcatgttg   17820
aatattgagt atattttggg tgaactttta agagttcaat gggagagaac aagcctctcg   17880
aaagcttgta attatcaact tgtttactg ttttcaaga aaactatcaa tcaagtccat   17940
tttacttctt aatcttcttc tctaatctgt cctagtgatg tcagttcatc acaaatggta   18000
tcagagcagt tcgttcccgg agattaagta ctgattttca gtttcaaaaa aaaaaaaaaa   18060
aaaaaaaaaa aaaaaaaaaa aaaatctgca atggagtttg cttcgcagga gacaaagaaa   18120
ttagctgaag atttaaatga gataatcaga aaaggttttg agaaatttca gcaagacctc   18180
caaaaagacc tcaagaaaag aatcagcgat gttttggctc caatcaaaac ggagttgcat   18240
tctcttcgaa aagagctgga ggatgaagaa aatgaagcaa atcggaggt ggtggcggaa   18300
gaggacgaag aggtggaaag aacaggtgat gattcactaa tcttcgtcac cggcggaatt   18360
gcagtggaac cagagagaat ggagatggat aaaagatctg aaggttcctc tagtggaagg   18420
caaaggaatt gctcgggtgg ttataacggt gtagtacatg gtggtgtcgc aaaaaaatca   18480
gatcgtgttg tcgaggtgg tccacttgga ggatattttg agagaggagg tgccggagga   18540
agtggttccg gtggaggtcc aggcgttgtc ttcggtggtt cgctgggtag taaatctggt   18600
agtggttgtt tacaggttct gggagatatt tgtggtggtg gatgtatgtt ggacggtgga   18660
aaaaaatgtt tcacaggtgg atctggttgt ggtctgagtt atttggccgg aaattggaag   18720
tttgatgttg gaaccgccac ttgtggtggc ctgaagaggg aaggaggagt agtcctgaag   18780
tgcagatttg gctcaaatgg atcgagtggt ggacctggaa cattttccga tgagaaatcc   18840
accggtgatt cagatcccct tgccggcaaa aatgttggtg aggaagatgg acgacattca   18900
tggagggtt tattgcagaa ggttccagaa cttgagcagc aaagaaggat gagtgaggtc   18960
tgggttggct tagagaagaa gccagggcta gaaggaggta gtaatggcaa tcttgtaatt   19020
actgaaaaaa gagagtccat gggccagccc atttctaaat tctctcagcc caatcttcct   19080
gtctcacata taaaccccac tactcacaga cccactttct taacacccaa aattttgagc   19140
ccttatttca ttaaactcat ccagcattta attgttacac taaattcctt ttctgatttc   19200
cccaacccaa atactaacaa tcagatatca aaatcacctt gccacactat cagttccact   19260
```

```
ctcactttga cttcacaacc tcacggcctt ccacttcctt gtgaccactt gatcaccacc    19320
ccaactttct tcatctcacc agttccaaat tttctgagtt cttccacagc ttcactcact    19380
tcttcactcc atcttttaa  acccaaaact ttcaagccac aagcgcataa caccagcagc    19440
acaccagacc atttcagaca ctctttcctt catcacttcc aggacttttt ctttctagtg    19500
gaggcactca ctcgagccag agaactttat gaggaggagc agcaacacga gctgaagcat    19560
aaactaggct tggggcctga agggctgcaa gacactgaat atacgagtag agggccagaa    19620
tttagtgatg attacgaccc accttgagga caaggtgaaa gtttgggcgg ccggtaatgt    19680
aatgaatcaa cctaggaaga ggggtacttt tggtattata ataattagtt agattttagt    19740
agtagcttga agaataagct agggagttag ggagtaaata tctctataaa tagaatggaa    19800
tagggagaga gaaagcatgt tgaatattga gtatattttg ggtgaacttt taagagttca    19860
atgggagaga acaagcctct cgaaagcttg taattatcaa cttgttttac tgttttcaa    19920 gaaaactatc aatcaagtcc attttacttc ttaatcttct tctctaatct gtcctagtga    19980
tgtcagttca tcacaaaaat ctagggtgtg ataaagacta agtagaattc tgaaaaaaca    20040
tttgtcagtg ggagggaggg atcaaagaag aaaatataat gaggatggaa atacacatgg    20100
atactctgaa ggaggtggct atgtaggaat attcccacaa aattttatgg atgtcgctaa    20160
tttccactaa attgggtcct aataagatgt taatagctat gatgttgaat tttaaagaac    20220
aatgctctta aagaatgtgc agtaactcaa tgttattttt gccttttgat tgcaggttac    20280
ttatagcatc ccatatgcac tgatttcctc caggattgag tcactggggc taggccaagg    20340
taaaggttgc tggatttttc ctcagttact ctgtattaaa atactgtaga ctaataatta    20400
ctttctctgc aggcttatca atgggtgtgt taaatcttgc aattgtgctt ccccaggtga    20460
agtttcaaag cccattctta ttttgtctt gtttttcga cttgaagcga tagtactcat    20520
cttaattcat ataaagaaa catctaaggt gcaaggagac atgatatgtg gagcagacta    20580
gcctgacaac aatgacatat tcaacccttg tacctgcgga ttagaaagat tttgtctttg    20640
ataaagcaat gtcccaagag aaccagaagt cttctccaca atgttataat taatcactgt    20700
gaattcaccc tattatacat cagataaaga agctcacaag aagctccaga agcttatgtc    20760
aacattaaca tataaattca tcatatgtta aaagagcacg ctatttgagc tttgctttct    20820
agctagatcc ttatagttat tcacatcaaa ccacacatct aagtttactc caagcttagg    20880
ctagtaactc gtgatcaagt taggctgtgt gggccaatcc ggtcctagtt tgggtaggta    20940
gaactagaat tataagtagt attatgctat cactttgtct attggtgttg ataagagaga    21000
accagttagg ttgttttggg aatttgcatc aattagatga ccacactgat aaaagaagtc    21060
agagttgcga ttggtattat ggagattttg gaagtccgag gaggccaaaa atgactttgt    21120
tagagggcgt taagaatgat ttaaggaaat tatgtttgca ggagcatata gcaattgaca    21180 aaagaatgg  atgtgaaggt tccatgtgaa ccatcaccag agataaaatt tgattcatgt    21240
ggccgtcttc atcctatcag cattgtcgtc tgacagtgtg caataatgat tgttgtcct   21300 gtctaaaaca aggtggatg  aagttagggt gagagagaaa ccttttaaaa aaactacgtg    21360
acaaacaatt cttcgaaaat ttgctcttac ggggcaagaa gtgtagtcgt gcaattgaaa    21420
ctatcattga aggagttcct cataaaaaag ttttataggc aattcctcac aaattgaccc    21480
ttttaaagga actatgtgac aaactgtcct tcaaaaatgg ttttcttaaa gtatcataca    21540 caatttttg  agtgtaaaat tgattgacaa catgagtaaa gtagaagcat gccatactaa    21600
agatcaatca gagggatgcc acataggaag gccatgggat aagggggagat aatgccttt   21660
```

```
aagatgatat taagaactta accgtataat atgatactgt attactatta gtaatataaa   21720
aggaccaaaa tctgaaagac tcatccgtga cttactatag tatcatatta tgcaatttgg   21780 tccttttat attcatgaag cattaaaagg accaaccta aagccataca tctaatggat    21840
ctaatacttt atgaaattca ttaagagcct acctccatgg tacatcaagg ggccattctg   21900
taataaattc tccaaatgag caaaattctg ttcataattc tattcactta tttctctctt   21960
ttctttcctc ctctttttt actcctcttc ttcattaatg tctcattcgt tgttttctt    22020 accgctaaat ttttctctcc tttattgttt ctcacctcca aatttctctc tcctttattg   22080
tttctcacct ccaaatttct ctgttttatt gtttctcatc tccaaatttc tctctcctca   22140
atttatttct cctacattgt ttctctcttc cctccaaatt tgcaatattc attgtaatta   22200
atcaatagca aatcaagtat tggagttttg aatttcatca atggtgatta atttcagatt   22260 tgaaatcaa caattgtgtt tctaaaattc ttcaagggcg gaattaatga tagataatgc    22320
aaaagataat ttaagaatca acactagttt tagattcttc tctgctccat tgtttctctt   22380
acctcaaaat ttctctcttc cattgtttct catcgtctaa tttctctcaa ctttatggtt   22440
gatgagaatc aatagcaaat caaatgatga attgtaaaat atgatttgaa aaaggtgggc   22500
ttcatcgatg ggaaaaacaa atatagaagt ttcggagttt atcaatgatg aactcagttt   22560
tacatttgaa atcaatatga gcaagcactt atagcataag cgttagttca tttgggcaaa   22620
agtgtgctca atttgacaaa tgagtagaag tgtttctcat ttgaaaaagt tcgcttattt   22680
gagatttctc aaatgagtaa tgagcaaaag agtcttgcgt ataccgtgag tccatgagta   22740
tgatacctct aggtgtatga taaaagttta tgacgaaata gcaaaccaga aaatgaatct   22800
aaacctgatt atatccagaa caagccaaat atggcgcaag ccgactgata gaataggaaa   22860
tatttttgta tatattttgt gattatattg taatctcttt tgactttatc tttattattc   22920
tgttcacatt ttgtatgact gctgtactgg tatacatatt gaagggagta cgcaattcca   22980
tggtatggca attatggaaa aactcttaag atttctttt cctctccccc agccgtgacc    23040
tgtttacctc ctcttctcct caattttctc tatggacgca ggaaacgaag atcatcttac   23100
ttcatattac ccatcttcca cctggtccta ggtgtcacca atattcagaa ccttgtccct   23160 cataacctt tgatctggaa aagctgcagt tttcctcatg gacagagtta ttcaagtgct   23220
tggtctgtgc ataacatcct ttgtcggatt aatgctagaa accctaaatc ctccaacatc   23280
gatgattttt tgtggaaaag actagatgcc attatcaagc aatgtatata ttctccaaac   23340
aatgctcaag ctccaccgca aaggacacat gggattacct atctgacgta ttcaaaaaca   23400
aatatacacg tgacgacatg acgtctatct cgaaaatcag cttttcttata ctttctctcg   23460 agatcccgta aggcctctac ctattgtcaa caattgaaga acttatctca tcaattgtat   23520
aattgtagga gcgtcgtgtg agatagcaag cttgatcttc aacaacttca ctcatgatta   23580
tagtagaggg gccacaatga tgctgcaatc agatcctctc ccgcccttct acaaagcatg   23640
ctcaatgttg gtgcttaagg aaactaagca tgctcaacat gcctattcct cccgcaacac   23700
tcgtttaacc ctcctttcct aaagtccac cccaagaata caataatgga tgtaatacta    23760
ttaaccgtgg aggagccaat gggcatgggt gtggattgaa gaatctcaat gagcaccgtg   23820
atagtggcgg atgaaatgcc tgcggggtg gccgttggaa taataatcag cattgaaata    23880
gttggcagca gcagtaactc tggaaccagt cttgtgtgca tagcagaacc acaggggtaa   23940
gtgggcagca cctacgtgtc cttacccttt gatcccgctc catctgcagc acccactggg   24000
```

```
aagcaatatg gctgcaggag tccttggtcc gagtctgtgg caacaacaag catatcctgt   24060
ctgtcctcca tcagtccaca acaacgatac tttttagaca atgagtccta ctcgccccaa   24120
tgatgcatgg tatgtggact tagggagcgt cgtttcatct cactacaatg caagtaacct   24180
cactagaagg ttaaatttgc gcactaatac taatattttg gtgggaaacg ctcatcttgt   24240
tccaatataa ggtctaggct catctcaact acacccttt ctttcaccat gctctctatc   24300
ctctgaaagt cattaaaaac ctgatattga gtttctattg agtttgacct ttggacttta   24360
tgtgaaggat cttcatatag gagcttacct tatgagatgt aatagctcct gagagttgta   24420 tccctcatg ccgtcaactc accaatgtgc tgccagcctg ccactatcat ttcccttgct   24480
gccatctttc ctagcatctg gcaacaatca ttctgttcat cctcttcgat gtcttcattt   24540
taggaattta ttacagtgga ttaaggagtc cacctccacc tattgttact cttgtcaagt   24600
tgtaaaacat gtcaggaatc cgttctccct atctgagaat gtaacccatt cctgttttga   24660
aatgataaat agttatttat ggactttttt agtgcccgtt tgttatcgtt ttttgttttc   24720
aattttcagt ttttttgaaa tctaaaaacc aaaaactgga aactagaaaa agtggttttc   24780
acttttcagt tgtcagtttt caaagtcatc atgttcccaa caaatttga ctaattttt    24840 tattcattat aggacatata tcatatgact ttaaaaatca aaaaccaaa aaacagaaaa    24900 ccacagtaat actgaacagg cccttagttt ctagttagaa tgttttcatt tttatttagt   24960 gcttttgat gattgctctt attatctttg ggtttttcc tcttaagaat aaattagaag     25020
tgtacaagat atatttaatt ttattgttta tgttcaaact caatttgagc accttgttcc   25080
aatattaagc ctttgcggac tccaaatagg aatgcaacta tgcaaggtaa gtatagtgtg   25140
ttgattaaca atagtactta gggacttagt gccatgcctc cttgggggct tatgtgatca   25200
atgtggttat ataagatcaa aatcaaatca gatggtagaa aaacataaag caagattgaa   25260
ggtaaatggt aagtccaagg ctcggaattg attataatga gatattagac cttaagttta   25320
ttggtgaaac cggaacaatg cacattgtat taagcgtggc tactttgagt tcatggccta   25380
ttcatcaact tgatgtcaaa aatgctttct tgcatcggaa cttacattca acagtgtata   25440
tacatcaatt gccgggtttt gttgataaaa acgtcttgtg atcaagtgtt tgcttcggcg   25500
aaacctttgt atggccttaa ataggctcct tgggatcggt accaaaaatt tgccgcattt   25560
attatgcaat caggatttgt caacagtaaa tctgacactt cttgttcat ctacctcaat    25620 ggtgttgaaa tgatatatct tattctctat gttgatgaca ttatgctcac cacgttgtcg   25680
aaacactttg catgtaacac ccccaaaacc cacgtgcgcc caccactgct gcgtcgcgtc   25740
gacctcgggg gcgttaccgc cgcgatggaa cgcaaggcat aataagggtt aacgataact   25800
taaaacatta acttgaaaac taaaatgcag cggaattaaa atataaatac aactcgggaa   25860
tcatcaatga cccctttcat tcaaaccaca aaccatacat aagtcttaga aaaccaata    25920 atacttattt caaatgcttt taaatgcaaa tacccaagcc tagtcccgt atgctcgaga    25980 ttatgcagca gcaccannnn nnnnnnnnnn nnnnnnnnnn nnnnnnnnnn nnnnnnnnnn   26040
nnnnnnnnnn nnnnnnnnnn nnnnnnnnnn nnnnnnnnnn nnnnnnnnnn nnnnnnnnnn   26100
nnnnnnnnnn nnnnnnnnnn nnnnnnnnnn nnnnnnnnnn nnnnnnnnnn nnnnnnnnnn   26160
nnnnnnnnnn nnnnnnnnnn nnnnnnnnnn nnnnnnnnnn nnnnnnnnnn nnnnnnnnnn   26220
nnnnnnnnnn nnnnnnnnnn nnnnnnnnnn nnnnnnnnnn nnnnnnnnnn nnnnnnnnnn   26280
nnnnnnnnnn nnnnnnnnnn nnnnnnnnnn nnnnnnnnnn nnnnnnnnnn nnnnnnnnnn   26340
nnnnnnnnnn nnnnnnnnnn nnnnnnnnnn nnnnnnnnnn nnnnnnnnnn nnnnnnnnnn   26400
```

```
nnnnnnnnnn nnnnnnnnnn nnnnnnnnnn nnnnnnnnnn nnnnnnnnnn nnnnnnnnnn    26460
nnnnnnnnnn nnnnnnnnnn nnnnnnnnnn nnnnnnnnnn nnnnnnnnnn nnnnnnnnnn    26520
nnnnnnnnnn nnnnnnnnnn nnnnnnnnnn nnnnnnnnnn nnnnnnnnnn nnnnnnnnnn    26580
nnnnnnnnnn nnnnnnnnnn nnnnnnnnnn nnnnnnnnnn nnnnnnnnnn nnnnnnnnnn    26640
nnnnnnnnnn nnnnnnnnnn nnnnnnnnnn nnnnnnnnnn nnnnnnnnnn nnnnnnnnnn    26700
nnnnnnnnnn nnnnnnnnta tcatgcttct aggttccaat aacatagatt gcaacctaat    26760
catgatacta atacttggga ttaaactggt acgcgtacgt accttgtaac ggagaatttt    26820
cgctgtctta atcgaacgtt ccgcttatga aattgggacc taaaccgtta aataaaagct    26880
ttagtgctac gtcgttggta atattaacaa ctactacgta actaagacta tacggtttaa    26940
taatttgaag taaacgataa ctaaacccct tgtttatgaa tcttcgttac ttttctatta    27000
taaagagttt aacgtctttt aagagtcaaa gctagtgaac atactaatat tagttagtgt    27060
cattagtcca ctatctttac caaccagtt aaattataaa tccaaccatg ttttatctcc     27120
aaaatcttat gccaaaagtc ttaaatccaa tccagtattg tgtccaaaag ttatattcgc    27180
aattatagtc agaataataa catgaactca ttaacttgta ttattaatta attaattata    27240
atttaacata attatgaaaa cataacttat aattaaactt tacataataa tataattgat    27300
tttataccgt taagctcgcc ggcaatcaat ttccggcgac cgatttccgg caacggcgca    27360
acaacttcgt cgcaccactt gcacagcagc agcagcgcac gtttcgagct tcgtcgcaca    27420
actcgcacaa ctcgcacagc agcagccttg cgcaaggctt cgtcgtccct cgctcaacac    27480
tcgaaccact cgactcgcac ttcgagcttc gtcgcactaa gcccctcctg cttgctcaac    27540
actcgaacca ctcgactcgc acttcgagct tcgtcgcact atgcccctcc tgctcgctcc    27600
tttgctcgca cccgagcctc gcaccagctt cgtcgctcgc agcccctcgca cgtccctcga   27660 acacacggac tcgctcgctc acccacacac cagcacgttc gcttgcacac acccgctccc    27720
ttcactcgca cacctcgaca aggatccgcg aagaacccag cgagggagac gaagagagag    27780
acgaacagcg agagagaggg agatgaggaa gaacagtgcg agagaggaga gagaaattga    27840
gagagaagaa gaaggggga tgacggctga aggagaaagg aaacttaggg ttttctgaaa     27900
tttctcctct tgcttccctt tttataacct tctaaaagtg gtaactctag atcgggtgaa    27960
ctcggtttaa cctttataaa tccgaaatta acacaaccga ctcgtattaa tattattata    28020
ttcttattat tcttgtaaat aatactaaat ccttttattt aacttcctta tattttctta    28080
attaatacga attaattctc aaaaatacgg agtattcat tgcatgtgtt ctgcatctag     28140
ccatctcaca tttacatgtc gagtttccta tgacaaagct gggtcctttg atttactctt    28200
tgggtgttgc ggtcactcaa catcctaata gttatttatg ttagaggaaa tagttaatgg    28260
tgctagcatg tcgaatgata aacctgttgc tacaccggta gatgcaaagg caaaaattca    28320
gtgatgacga ggcccattta tatttgattc ttcactctat tgtagccttg ccagagtttt    28380
gctatatctc accttcgtct gatatagcta ggtgtgtctt tttatgcacg cgcctcatga    28440
gccacacttt aatgctccac cgttcataat tcggtatttt agaggtacct ttggtgcagt    28500
agggtacccg gacgcatgca ggtcgacttc agttgctagg tgacaatttt gtttctcgca    28560
atggagctga agcgtaatat agcaatgaaa atctctactc aaactgcatt gaccattata    28620
ttgtgctaca atcagtatgg tgataatgtc aatgtcatct acctttctag taatccctta    28680
agcatcgacg aacgacacat gtagagatgg atattcgttt aggctcagaa aaggttgctt    28740
```

```
tagtccaagt tggagtcctt tatgtttctg cttctacatt caagcatgcg ctccccccccc  28800
cccaatcccc ttccaattgt gaggtgtgat agagtaggta atgttcttgg ttatattttg  28860
tcaatatatt atgatctctt tgatttcacc tttattattg taccgacaat cttccctttt  28920
tggatcactg ctgtattgct atttatattg aagggaatac acaaatctaa gtaaggagat  28980
tctcatatat ctaaatcgac ctaatttaat aaaaacgaca ttttttttgtt ttgcaaattg  29040
tgttaaaaga gacctctagt tgtaatttat tattttgggt ctatggccat agtcacaagt  29100
tacaatcgcg tctgtgatgt tcgttataaa aaccaatttt aagagaatga aaagaaggaa  29160
aagtaataat acctatgaga caaacccaa acgactttta tagaaagcaa taatgaaatt  29220
agtgcttctc atctagtttt tgagcttaac aacttaaagc aaatcgtgga attattgaaa  29280
caacaacatc ttctttaatc aaattactgc tccaatattt tcccaaatcc caagcactct  29340
ctacttagcg ccagaaaacca agtgtgaact aagaagatct tgttcttttt atcttcccct  29400
cttcaccaag aaaaaccagt ccatcaattt ctctaaattc cttcaaagag gatggaacaa  29460
aagcattcat attatataat ctgaacatgg atttctatga aattgttttt cccatgttgt  29520
tttatttcct aggatgtata ataagttgtt tagtttagga ggacaagtaa tactccccat  29580
gtttgtttta atgtcaacca aacgagttca aagtataact ctctcttttg taactataac  29640
tgttgtttac catggagtgg aacgggttaa aaagaaaga aaacgtaaag gcaaaatgac  29700
aaatgagaag cggccacccc acttggctag gtcaacaaaa ctgaaaatgc aaaggcaaaa  29760
ttacaaatga gaagcggcca ccctacttgg ctaggtcaac aaaaactcca ttggatttag  29820
agttggagat gagtcttttg atcttgtaaa cccattttc acctatagcc aaggaaaaaa  29880
tcacggatgt ggtcgcggtc gcgagtttgc accgtcgtgg aagtagcttg taacggatga  29940
ttgaaacaaa tcactgtcga cacgacatcc aaaaattcac attaatatat gctaaactta  30000
tttgcaattg ttttagttta tgaagcatta ttacaattta caacataatt aaatcaaatc  30060
tatcataata tcatgtttta ttagcttat aattaattca taaattgaat gtctgaaaaa  30120
aagatctaac agggataaaa atgttctaac gcggggagtt cgcgttacgg aacggaaatg  30180
cagcaaaaat tatatgattt ttattataat gtttcttaac gagacttcac gaaacgtgca  30240
aatccaaaat tcttttgtag aacgaccgtt ctgtaacgga acggaagagt tttaattcca  30300
tgcctatagc cttatggcct tttggcaatg taaccaactc ccatatatca attttctcta  30360
ttgagtggat ctcctctttt attacagatc tccattattc ttttgtagca acttcttcaa  30420
aattgatgga ttcatacgtt atacttcctc cgttccataa aaagtgaaat gacttgacca  30480
taacacgtta actagtggaa tgttttgatt ccgtaagact ttctccagat gatctagtat  30540
ccggagcagc tttctcttcat tacttaaggt tcgtcaagt tgtagggcct cgtaagataa  30600
cacatgagag gggtcatgta catacttccg taattgggat acatgaaaaa cattgtggat  30660
ttaggacatc tttgtcggta gcgagatctt atatgctacc tcaccgaccc tttgaagaat  30720
ctcgtacagt ccaataaact tcgggctaag cttcccctga ataccaaatc tcttcccacc  30780
cttagtaggt gataccttaa ggaaaacctt atcacccacc ttgaattcta atttcctact  30840
ccgattatcg gcatatttct cttggcaatt tagggtgatt tcatttttct tccgaatcac  30900
tcggacttga tccacggtct cttgtatttc gccactcaaa ttgtcccagc aaatcggtgt  30960
tcgacatctt cgattatata aagcttcatg tggggccgtt ttgattgtgg tttggtatcc  31020
tctcaaaact cttggaactc catggcacat gcctgtagca tgttagtgcg ttctgtttga  31080
ccattagtgg ccggttagat cgcgattcta aattcagtgt tatcccaaat gcttcttgaa  31140
```

```
acttttgcca gaagtgtgct agaaatcgag ggtccatgcc tgaaacaata attactggta    31200
ccccatgaag tcgaacaata tatcggatat aagcttcggt tgtcttttca tatatgtctg    31260
ttaggcttct catcttagca tgtgttttca tcatatgaat cattgttatt tctttgagtc    31320
tttggttgag ttttttcaga attcgtcccc gtaatataat atgttcttca aacacattta    31380
tttttccttt ttccctgtct tgattatccc atttccatga ttcttcttca ctaaagatta    31440
caacttatga taatccacat tatcgtcatt tttctaaata ggaattttac cttttccaaa    31500
tgatttccat ttttttttata atcttcaaat cgtgcatagg aattaaagga gcgatcatat    31560
taagagaata attctttatt gccctatatg attgcttgat atggtgtcac attatcttgg    31620
ccttcctcat tattacaaac caataatacc gtctcctcta gttcattttc agatttctcc    31680
gtgtgattaa ccttttcttc tacaggggat ttagaataac attctgtaat gtacatgttt    31740
attgcaattg aaacattaaa cacgagactt atctggattt tcattacttc tgaattcttg    31800
acctcaacta cgaccatatc cacgctcacg accttgttgt cgctgattgg aattatattc    31860
acgatggtac caaacacctt cattcacaat gtatctttct cctccttaag cctcaacctc    31920
cagaatttcc atgtctattt acaagtgttt tagcttgcaa tgcttgctct tcaagctcat    31980
aagaattcgt cctttcctca tgtactaaca gtaccatgta cctcatttaa agaaagatgt    32040
ttttgatgct tcgctcatat aacatgcata ctattgtctg aaacttagaa attatagatc    32100
taagaatctc taatactatt tcggattctt tgatgttatc gccaagtgct ttcatgttat    32160
ttgctataga aataatctga tcaatatgct cggatgttgt tttcgaactt ttcattttta    32220
gaagttcaaa atatgatttc aaatgttgaa tttgacaatt ttacaagggt atttccttga    32280
caagttttat caaggatatc ctagctattt tctcaaacgg gttttgtcca tccatagccg    32340
aatggataaa cttaaagact tcaattcttt ttttcttgtt tcatttagtt ccttcttttg    32400
tggttcagtc ataacaacct cctcttcttc tattggctcc ttataatcac tttgtacaac    32460
atcccacact tcatgaaact tgaaaataac tttcatttgc acattccaag gctcatagtt    32520
tttatcggag aatttaggca aaatgggact tgaagtggta cttgatgatg ccattctctt    32580
aggtttatag ttagagtact tagagggata ttgtaattca cgggatatat aaggttttgc    32640
taatattcgt tgaaggatta gtgagaccgt tggttgttct ttttgtacct cttaaggggg    32700
aggttcccac gttaaattta cgttgtcatt gctttaaatt tcgctcccta gatgtgatat    32760
attgttactt gctactacac ttccgcataa gtcctaacaa gtggtatgaa gagcctaggt    32820
gaaacctaga atagatggac aagattttg gaggaaagtt caagatgaaa ttgttcaatg    32880
acaagaacaa atttgcatta ttgacaaagc atgatgaaag atattatgac tcaacaagga    32940
ttgtataatg cctttgtaga caagaaaccc gaagatgtca aagatcccaa atgggaagac    33000
atggagaggc atgcaacatt gagtatcgga ttagcccttg caccagagat taagtatgat    33060
gtgcttaaag aaacaaaacc caaagagttg tgggataaat tggagaaggt gtttcaatct    33120
aagtctttgg tgagtaagtt gtttcttaga aaaaatttct tcggtttgga aatggaccaa    33180
agcaaagact ttacatatca catcatgttc aataaattga tcacccaatt ggtaaagttg    33240
gatgagatgt tcaaggatga agacaagaca aatttgctcc tagtatctct ttcaataaaa    33300
tttaatactg ttattacttc tttgttggta gggaagacaa cattgacctt ggatgagatg    33360
cctttcataa gtcgaaaagt tgatgaagca aggaggagga tcatcaagtc aaagggagc    33420 ctttagtgtg tcggcgtgtg gtaaatgggg taagaaagtg tgtatttctg atgtgacctc    33480
```

| | | | |
|---|---|---|---|
| tcactattgt | gataaaaagg | ggcacttcca | atcgcaacgc | ccaaaggcaa | agatggattt | 33540 |
| gaagaagctc | agggagtgaa | agggaatgac | gaccatggtt | tgaggggggag | atacatttga | 33600 |
| cgaggaatat | ccacatgacg | ctccgttggt | tgcaagtatt | gtagaaccaa | caagcgaatg | 33660 |
| agttttagat | ttgagatgct | tgtttcatat | ttgccacaag | gagcatgact | gttttttaga | 33720 |
| aggtgtgaaa | aagaagcgat | caatctactt | gatggggata | gagtgaagga | tgacgggata | 33780 |
| ggtgagatcg | tgctcgagcc | tcatggtcat | tgtagacatc | ttacgcaagt | aagatacatc | 33840 |
| ctactcgtaa | ataataacat | gatttctcta | gaaaaacttc | acgatggatg | cactatcaag | 33900 |
| agacattaag | gagctatttt | agttatagag | tgctgggaga | caatcatgaa | agcaacacgg | 33960 |
| aatacgaaaa | gcgtcttcgt | agttgaagca | tgtgtcaagc | acggagaggt | cttggtttga | 34020 |
| ggggaggcat | cgtcacccca | ccaacgacgt | gaagctcttg | atcgttgatc | gaagaggttg | 34080 |
| gccgtgtttg | agcttgatgg | gaggttcttt | gttatgcaag | tccaatagtc | caatatggtt | 34140 |
| agtatgtgtg | ttttgggagt | gttcaaggaa | aaattaatac | gaattggata | atttttgttt | 34200 |
| gcccgtaggg | tagaaccctc | tcccgcggga | cttttttgatt | tcttttcttt | tttttattt | 34260 |
| tattattttc | taagtcttgt | catgttagga | ttctttagag | attatttatt | tcctaataaa | 34320 |
| ttgataattg | tattaagaaa | taaataatta | cttttctaag | tctagttaga | attagattgt | 34380 |
| gttagatgct | aattctacta | gtgataggat | ttcatcctaa | gtataaaggg | ggattaggat | 34440 |
| cattatttta | tacactcatc | aaatacatgg | ggaagttaca | aagactctta | ggtttctagt | 34500 |
| tagagttatt | gagagattgt | aattcacggg | atttgtgagt | tttggagttt | tgctaatatt | 34560 |
| cgttgaagga | ttagtgaagc | cattggtggt | ttttctctgc | ttgttgatgg | gggaggtttc | 34620 |
| cactctttgc | atttgtcatt | gctttaattt | tgctcctttg | atttgtttat | atagtttatt | 34680 |
| tgcttctaga | ctaacgctaa | gtcctgacag | ctccaaggta | gaaaaatttc | ctagctatat | 34740 |
| gtaaatagtg | aagagtttat | tttgtttaaa | gctgataact | gataaatgag | cttccatggt | 34800 |
| caagatgcac | aagtattgtg | cctcaataaa | tactctgatg | aatttgcagg | tgattgtgtc | 34860 |
| cttgggaagc | gggccatggg | atcaattgtt | tggtggggga | aactcaccat | ctatagctgt | 34920 |
| agcaggagtc | gcgtcttttg | ctagtggact | catggccatc | ttggctcttc | ctcgatctag | 34980 |
| aactgataaa | tccagagttc | atgtgatgca | tgtatgaggt | atttaaagtt | ttgattttgt | 35040 |
| ttagctattc | atgcatatga | atagcaagat | gtgaaacatg | agaatctgta | catagtgata | 35100 |
| tacccatttg | ttataataaa | aagaacgtgt | tccacttgat | gatggttcag | ctataaccat | 35160 |
| tactgaatat | aattggattt | gctattttta | ttagattatt | agatgtttgt | ttgtttttgtt | 35220 |
| cttcaggaat | ggaaacattt | ctctttggtg | gcaaggtaaa | actaaataga | ga | 35272 |

<210> SEQ ID NO 5
<211> LENGTH: 1605
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of BvSUT4/SUC4

<400> SEQUENCE: 5

| | | | |
|---|---|---|---|
| atgacaggcc | aggaccaaaa | taaaacagag | atcaccagag | aaacaattac | aaaaccccga | 60 |
| cgacaaaccc | actcaagccg | tcaacctcgt | cccacaaccc | gaccaccacc | acctcgtcct | 120 |
| ccacaacctc | ctccaacccg | gcccgcccga | gtcccactaa | aaaagctctt | aaaagtaaca | 180 |

| | |
|---|---|
| tccgttgcag gtggcataca attcggttgg gccttacaac tctctctcct aactccttac | 240 |
| gttcaagagt taggcatccc tcatgctttt gctagtatca tttggctttg tggtcctgtc | 300 |
| tctggtttca tcgtccagcc tttagtcggc catattagtg accgctctac tagtcgctat | 360 |
| ggccgtcgtc gccctttat tcttgctggt gctgccatga tcattgctgc tgtttcaatt | 420 |
| gttggattct ccgctgatat tgggttttg atggggata aagttgatgg aggagagaga | 480 |
| aaacgaccga tggcgattgt tgttttgtt attggctttt ggttgcttga tgttgctaat | 540 |
| aatactactc aaggtccttg tagagctttg cttgctgatc ttactggcaa ggatcataga | 600 |
| aggaacagag tagcaaatgc atactactct ttgtatatgg ctattggcaa catccttggc | 660 |
| tttgccacag gatcatacac tagctggtac actattcttc cattcactcg cactcatgct | 720 |
| tgcagtgaaa gttgtgccaa tctcaagtca gctttcctca tcgacattat atttatagta | 780 |
| ataacaacgt atataagtat cacagctgct catgaagttc ctttgaatac cgaggatgga | 840 |
| ggcactggca tatcagaagg atctcagcca tctggccatg ctgaggaagc cttcttttgg | 900 |
| gaactatttg gaacttttag atatctacct ggacctgttt ggattatcct ttcgttact | 960 |
| gcactgactt ggattgggtg gtttccattc ctactctttg acactgactg gatgggtcgg | 1020 |
| gaagtttatg gtggtgatcc agatgaaggg caaatctacc atagaggagt cagtacaggt | 1080 |
| gctcttggcc tgatgtcgca atcagttgtt ctgggtataa cttcattgtt gatggagaag | 1140 |
| ctctgcaaga agttgggttc tgggattttg tggggcatct caaacattat tatgtctttg | 1200 |
| tgttttgttg caatgcttgt catcgctttt gtactgagca aggcagactc ctttggttcc | 1260 |
| gggagtcctc ctaatggtgc tgttattgct gcagtgattg ttttcacgat tctcggtatg | 1320 |
| ccattggcgg ttacttatag catcccatat gcactgattt cctccaggat tgagtcactg | 1380 |
| gggctaggcc aaggcttatc aatgggtgtg ttaaatcttg caattgtgct tccccaggtg | 1440 |
| attgtgtcct tgggaagcgg gccatgggat caattgtttg gtgggggaaa ctcaccatct | 1500 |
| atagctgtag caggagtcgc gtctttgct agtggactca tggccatctt ggctcttcct | 1560 |
| cgatctagaa ctgataaatc cagagttcat gtgatgcatg tatga | 1605 |

<210> SEQ ID NO 6
<211> LENGTH: 534
<212> TYPE: PRT
<213> ORGANISM: Beta vulgaris

<400> SEQUENCE: 6

Met Thr Gly Gln Asp Gln Asn Lys Thr Glu Ile Thr Arg Glu Thr Ile
1               5                   10                  15

Thr Lys Pro Arg Arg Gln Thr His Ser Ser Arg Gln Pro Arg Pro Thr
            20                  25                  30

Thr Arg Pro Pro Pro Arg Pro Gln Pro Pro Thr Arg Pro
        35                  40                  45

Ala Arg Val Pro Leu Lys Lys Leu Leu Lys Val Thr Ser Val Ala Gly
    50                  55                  60

Gly Ile Gln Phe Gly Trp Ala Leu Gln Leu Ser Leu Leu Thr Pro Tyr
65                  70                  75                  80

Val Gln Glu Leu Gly Ile Pro His Ala Phe Ala Ser Ile Ile Trp Leu
                85                  90                  95

Cys Gly Pro Val Ser Gly Phe Ile Val Gln Pro Leu Val Gly His Ile
            100                 105                 110

Ser Asp Arg Ser Thr Ser Arg Tyr Gly Arg Arg Arg Pro Phe Ile Leu
        115                 120                 125

```
Ala Gly Ala Ala Met Ile Ile Ala Ala Val Ser Ile Val Gly Phe Ser
    130                 135                 140

Ala Asp Ile Gly Phe Leu Met Gly Asp Lys Val Asp Gly Gly Glu Arg
145                 150                 155                 160

Lys Arg Pro Met Ala Ile Val Val Phe Val Ile Gly Phe Trp Leu Leu
                165                 170                 175

Asp Val Ala Asn Asn Thr Thr Gln Gly Pro Cys Arg Ala Leu Leu Ala
            180                 185                 190

Asp Leu Thr Gly Lys Asp His Arg Arg Asn Arg Val Ala Asn Ala Tyr
        195                 200                 205

Tyr Ser Leu Tyr Met Ala Ile Gly Asn Ile Leu Gly Phe Ala Thr Gly
    210                 215                 220

Ser Tyr Thr Ser Trp Tyr Thr Ile Leu Pro Phe Thr Arg Thr His Ala
225                 230                 235                 240

Cys Ser Glu Ser Cys Ala Asn Leu Lys Ser Ala Phe Leu Ile Asp Ile
                245                 250                 255

Ile Phe Ile Val Ile Thr Thr Tyr Ile Ser Ile Thr Ala Ala His Glu
                260                 265                 270

Val Pro Leu Asn Thr Glu Asp Gly Gly Thr Gly Ile Ser Glu Gly Ser
            275                 280                 285

Gln Pro Ser Gly His Ala Glu Glu Ala Phe Phe Trp Glu Leu Phe Gly
    290                 295                 300

Thr Phe Arg Tyr Leu Pro Gly Pro Val Trp Ile Ile Leu Ser Val Thr
305                 310                 315                 320

Ala Leu Thr Trp Ile Gly Trp Phe Pro Phe Leu Leu Phe Asp Thr Asp
                325                 330                 335

Trp Met Gly Arg Glu Val Tyr Gly Gly Asp Pro Asp Glu Gly Gln Ile
                340                 345                 350

Tyr His Arg Gly Val Ser Thr Gly Ala Leu Gly Leu Met Ser Gln Ser
            355                 360                 365

Val Val Leu Gly Ile Thr Ser Leu Leu Met Glu Lys Leu Cys Lys Lys
        370                 375                 380

Leu Gly Ser Gly Ile Leu Trp Gly Ile Ser Asn Ile Ile Met Ser Leu
385                 390                 395                 400

Cys Phe Val Ala Met Leu Val Ile Ala Phe Val Leu Ser Lys Ala Asp
                405                 410                 415

Ser Phe Gly Ser Gly Ser Pro Pro Asn Gly Ala Val Ile Ala Ala Val
                420                 425                 430

Ile Val Phe Thr Ile Leu Gly Met Pro Leu Ala Val Thr Tyr Ser Ile
            435                 440                 445

Pro Tyr Ala Leu Ile Ser Ser Arg Ile Glu Ser Leu Gly Leu Gly Gln
    450                 455                 460

Gly Leu Ser Met Gly Val Leu Asn Leu Ala Ile Val Leu Pro Gln Val
465                 470                 475                 480

Ile Val Ser Leu Gly Ser Gly Pro Trp Asp Gln Leu Phe Gly Gly Gly
                485                 490                 495

Asn Ser Pro Ser Ile Ala Val Ala Gly Val Ala Ser Phe Ala Ser Gly
            500                 505                 510

Leu Met Ala Ile Leu Ala Leu Pro Arg Ser Arg Thr Asp Lys Ser Arg
        515                 520                 525

Val His Val Met His Val
    530
```

<210> SEQ ID NO 7
<211> LENGTH: 3556
<212> TYPE: DNA
<213> ORGANISM: Arabidopsis thaliana

<400> SEQUENCE: 7

```
tttttctttt atgagtttct aactttctat ataaagtttc gaaaacatta ccaataatcg      60
tcgtaaatca ctccccacct cattcatatt tttagccgcc agaagaactg attggtgtaa     120
aatccaattt tcttgctgtt gtgagttttc acttctccga ggtaaaaaaa ctaatcccgg     180
cggtgagaat ctcttgggaa cttgctctga acgaaacttt tgttgcaat aattgtaacc      240
aaaaaataaa gaagacaaaa tcttttttgtc cttattgtag attccatcgc cggagcctgt    300
ccgaaaataa aatttaacta aacttggcaa aattcattca aaacgagtcc aaatcaaatc    360
aaccccctatt tcaacgcctc tttttctccc tgatttatat atcggagaga tttcaaggca    420
aagcttctc atttcctcgt aattgccggc gaattctact aaaggtgaga cctttttcat      480
tttcccagaa agtgaagcaa tcttttttggg gttttattct ctttagcttt cttaactgat   540
caaactaaaa aagcaattct gtttttttctt tcttccctcc tataggttag ttactctgca   600
tttttgatta ctgtttgatg attttttatgt ttagggttt taattgagca aattcttctg     660
ggtttatcag attttatatt tttgtgaatt ggttaagatt tagatctgga tttagatttt   720
tctttgtttc atggttgact gaaagtttga aacttcaaat ggagaatcac tgaatctgac    780
tgatttgaat tttggtggtg tttctagagt ttgttgagca atgaagggag cgactctcgt    840
tgctctcgcc gccacaatcg gcaatttctt acaaggatgg gacaatgcca ccattgctgg    900
tttgtttctt ttttcactct tgttggtgca attgtgtttt gttttgatca attatcatct    960
gagatttgaa aaatgttaca atgatgttgt attggatttg attgcaggag ctatggttta   1020
tatcaacaaa gacttgaatc taccaacctc tgttcaaggt cttgtcgttg ctatgtcatt   1080
gatcggtgca acggtcatca cgacttgctc aggaccgata tctgattggc tcggcagacg   1140
ccccatgctc attttatcat cagttatgta tttcgtctgc ggtttgataa tgttgtggtc   1200
tcccaatgtc tatgttctgt gctttgctag gcttcttaat gggtttggtg ccgggctcgc   1260
ggttacactt gtccctgttt acatttctga aaccgctcct ccggagatca gaggacagtt   1320
aaatactctc cctcagtttc ttggctctgg tggaatgttt ttgtcatact gtatggtttt   1380
cactatgtcc ctgagtgact cccctagctg gagagccatg ctcggtgtcc tctcgatccc   1440
ttctcttctt tatttgtttc tcacggtgtt ttatttgccc gagtctcctc gttggctggt   1500
tagtaaagga agaatggacg aggctaagcg agttcttcaa cagttatgtg gcagagaaga   1560
tgttaccggt aaggtttctt ctcgctatct tttttggtta tatcacctga atccactttt   1620
gacggttctt tttatattaa atgcagatga gatggcttta ctagttgaag gactagatat   1680
aggaggagaa aaaacaatgg aagatctctt agtaacttg gaggatcatg aaggtgatga    1740
tacacttgaa accgttgatg aggatggaca aatgcggctt tatggaaccc acgagaatca   1800
atcgtacctt gctagacctg tcccagaaca aaatagctca cttgggctac gctctcgcca   1860
cggaagctta gcaaaccaaa gcatgatcct taaagatccg ctcgtcaatc ttttttggcag   1920
tctccacgag aagatgccag aagcaggcgg aaacactcgg agtgggattt ccctcatttt   1980
cggaagcatg ttcagtacta ctgccgatgc gcctcacggt aaaccggctc attgggaaaa   2040
ggacatagag agccattaca acaaagacaa tgatgactat gcgactgatg atggtgcggg   2100
tgatgatgat gactcggaca acgatttgcg tagcccctta atgtcgcgcc agaccacaag   2160
```

-continued

```
catggacaag gatatgatcc cacatcctac aagtggaagc actttaagca tgagacgaca    2220
cagtacgctt atgcaaggca acggcgaaag tagcatggga attggtggtg gttggcatat    2280
gggatataga tacgaaaacg atgaatacaa gaggtattat cttaaagaag atggagctga    2340
atctcgccgt ggctcgatca tctctattcc cggaggtccg gatggtggag gcagctacat    2400
tcacgcttct gcccttgtaa gcagatctgt tcttggtcct aaatcagttc atggatccgc    2460
catggttccc ccgagaaaaa ttgctgcctc tggaccactc tggtctgctc ttcttgaacc    2520
tggtgttaag cgtgccttgg ttgttggtgt cggcattcaa atactgcagc aggtaagata    2580
aaactttga ttgttcagac acgagtactc ttggatctat catttgatca cttctctgat    2640
tatctcgagt tttattttgt atgcagtttt caggtatcaa tggagttctc tactacactc    2700
ctcagattct cgaacgggct ggcgtagata ttcttctttc gagcctcgga ctaagttcca    2760
tctctgcgtc attcctcatc agcggtttaa caacattact catgctccca gccattgtcg    2820
ttgccatgag actcatggat gtatccggaa gaaggtaaat atcaaaacct ataagatatt    2880
ttaacatgtt tccttgtttt ctcatgatac taaagttatc tctgtttcat tttgcaggtc    2940
attacttctc tggacaatcc cagttctcat tgtctcactt gtcgtccttg tcatcagcga    3000
gctcatccac atcagcaaag tcgtgaacgc agcactctcc acaggttgtg tcgtgctcta    3060
cttctgcttc ttcgtgatgg gttacggtcc cattccaaac atcctctgtt ctgaaatctt    3120
cccaacaaga gtccgtggtc tctgcatcgc catatgtgct atggtctttt ggattggaga    3180
cattattgtc acgtactcac ttcccgttct cctcagctcg atcggactag ttggtgtttt    3240
cagcatttac gctgcggttt gcgttatctc atggatcttc gtttacatga aagtcccgga    3300
gactaaaggc atgcctttgg aagttatcac agactacttt gcctttggag ctcaagctca    3360
agcttctgct ccttctaagg atatataact tgtaactttc ttcttcgtca attgctctgt    3420
gtacctaaag attctcttca tcccctttt gttttgtttt tcagataccct tcatatcgtt    3480
tttgtttctt tttttttttt ttttttcct ttgtttcgtt gtcaaaatca atctaataag    3540
tactcaattt tctctc                                                   3556
```

<210> SEQ ID NO 8
<211> LENGTH: 2205
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of AtTMT1

<400> SEQUENCE: 8

```
atgaaggag cgactctcgt tgctctcgcc gccacaatcg gcaatttctt acaaggatgg      60
gacaatgcca ccattgctgg agctatggtt tatatcaaca aagacttgaa tctaccaacc     120
tctgttcaag gtcttgtcgt tgctatgtca ttgatcggtg caacggtcat cacgacttgc     180
tcaggaccga tatctgattg gctcggcaga cgccccatgc tcatttatc atcagttatg     240
tatttcgtct gcggttttgat aatgttgtgg ctcccaatg tctatgttct gtgctttgct     300
aggcttctta atgggtttgg tgccgggctc gcggttacac ttgtccctgt ttacatttct     360
gaaaccgctc ctccggagat cagaggacag ttaaatactc tccctcagtt tcttggctct     420
ggtgaatgt ttttgtcata ctgtatggtt ttcactatgt ccctgagtga ctcccctagc     480
tggagagcca tgctcggtgt cctctcgatc ccttctcttc tttatttgtt tctcacggtg     540
```

```
ttttatttgc cgagtctcc tcgttggctg gttagtaaag gaagaatgga cgaggctaag      600
cgagttcttc aacagttatg tggcagagaa gatgttaccg atgagatggc tttactagtt      660
gaaggactag atataggagg agaaaaaaca atggaagatc tcttagtaac tttggaggat      720
catgaaggtg atgatacact tgaaaccgtt gatgaggatg acaaatgcg gctttatgga      780
acccacgaga atcaatcgta ccttgctaga cctgtcccag aacaaaatag ctcacttggg      840
ctacgctctc gccacggaag cttagcaaac caaagcatga tccttaaaga tccgctcgtc      900
aatcttttg gcagtctcca cgagaagatg ccagaagcag gcggaaacac tcggagtggg      960
attttccctc atttcggaag catgttcagt actactgccg atgcgcctca cggtaaaccg     1020
gctcattggg aaaaggacat agagagccat acaacaaag acaatgatga ctatgcgact     1080
gatgatggtg cgggtgatga tgatgactcg gacaacgatt gcgtagccc ttaatgtcg     1140
cgccagacca aagcatgga caaggatatg atcccacatc ctacaagtgg aagcactta     1200
agcatgagac gacacagtac gcttatgcaa ggcaacggcg aaagtagcat gggaattggt     1260
ggtggttggc atatgggata tagatacgaa aacgatgaat acaagaggta ttatcttaaa     1320
gaagatggag ctgaatctcg ccgtggctcg atcatctcta ttcccggagg tccggatggt     1380
ggaggcagct acattcacgc ttctgccctt gtaagcagat ctgttcttgg tcctaaatca     1440
gttcatggat ccgccatggt tccccggag aaaattgctg cctctggacc actctggtct     1500
gctcttcttg aacctggtgt taagcgtgcc ttggttgttg gtgtcggcat tcaaatactg     1560
cagcagtttt caggtatcaa tggagttctc tactacactc ctcagattct cgaacgggct     1620
ggcgtagata ttcttctttc gagcctcgga ctaagttcca tctctgcgtc attcctcatc     1680
agcggtttaa caacattact catgctccca gccattgtcg ttgccatgag actcatggat     1740
gtatccggaa gaaggtcatt acttctctgg acaatcccag ttctcattgt ctcacttgtc     1800
gtccttgtca tcagcgagct catccacatc agcaaagtcg tgaacgcagc actctccaca     1860
ggttgtgtcg tgctctactt ctgcttcttc gtgatgggtt acggtccat tccaaacatc     1920
ctctgttctg aaatcttccc aacaagagtc cgtggtctct gcatcgccat atgtgctatg     1980
gtcttttgga ttggagacat tattgtcacg tactcacttc ccgttctcct cagctcgatc     2040
ggactagttg gtgttttcag catttacgct gcggtttgcg ttatctcatg gatcttcgtt     2100
tacatgaaag tcccggagac taaaggcatg cctttggaag ttatcacaga ctactttgcc     2160
tttggagctc aagctcaagc ttctgctcct tctaaggata tataa                      2205
```

<210> SEQ ID NO 9
<211> LENGTH: 734
<212> TYPE: PRT
<213> ORGANISM: Arabidopsis thaliana
<400> SEQUENCE: 9

```
Met Lys Gly Ala Thr Leu Val Ala Leu Ala Ala Thr Ile Gly Asn Phe
  1               5                  10                  15

Leu Gln Gly Trp Asp Asn Ala Thr Ile Ala Gly Ala Met Val Tyr Ile
                 20                  25                  30

Asn Lys Asp Leu Asn Leu Pro Thr Ser Val Gln Gly Leu Val Val Ala
             35                  40                  45

Met Ser Leu Ile Gly Ala Thr Val Ile Thr Thr Cys Ser Gly Pro Ile
         50                  55                  60

Ser Asp Trp Leu Gly Arg Arg Pro Met Leu Ile Leu Ser Ser Val Met
 65                  70                  75                  80
```

```
Tyr Phe Val Cys Gly Leu Ile Met Leu Trp Ser Pro Asn Val Tyr Val
                85                  90                  95

Leu Cys Phe Ala Arg Leu Leu Asn Gly Phe Gly Ala Gly Leu Ala Val
            100                 105                 110

Thr Leu Val Pro Val Tyr Ile Ser Glu Thr Ala Pro Pro Glu Ile Arg
            115                 120                 125

Gly Gln Leu Asn Thr Leu Pro Gln Phe Leu Gly Ser Gly Gly Met Phe
        130                 135                 140

Leu Ser Tyr Cys Met Val Phe Thr Met Ser Leu Ser Asp Ser Pro Ser
145                 150                 155                 160

Trp Arg Ala Met Leu Gly Val Leu Ser Ile Pro Ser Leu Leu Tyr Leu
                165                 170                 175

Phe Leu Thr Val Phe Tyr Leu Pro Glu Ser Pro Arg Trp Leu Val Ser
            180                 185                 190

Lys Gly Arg Met Asp Glu Ala Lys Arg Val Leu Gln Gln Leu Cys Gly
            195                 200                 205

Arg Glu Asp Val Thr Asp Glu Met Ala Leu Leu Val Glu Gly Leu Asp
        210                 215                 220

Ile Gly Gly Glu Lys Thr Met Glu Asp Leu Leu Val Thr Leu Glu Asp
225                 230                 235                 240

His Glu Gly Asp Asp Thr Leu Glu Thr Val Asp Glu Asp Gly Gln Met
                245                 250                 255

Arg Leu Tyr Gly Thr His Glu Asn Gln Ser Tyr Leu Ala Arg Pro Val
            260                 265                 270

Pro Glu Gln Asn Ser Ser Leu Gly Leu Arg Ser Arg His Gly Ser Leu
            275                 280                 285

Ala Asn Gln Ser Met Ile Leu Lys Asp Pro Leu Val Asn Leu Phe Gly
        290                 295                 300

Ser Leu His Glu Lys Met Pro Glu Ala Gly Gly Asn Thr Arg Ser Gly
305                 310                 315                 320

Ile Phe Pro His Phe Gly Ser Met Phe Ser Thr Thr Ala Asp Ala Pro
                325                 330                 335

His Gly Lys Pro Ala His Trp Glu Lys Asp Ile Glu Ser His Tyr Asn
            340                 345                 350

Lys Asp Asn Asp Asp Tyr Ala Thr Asp Asp Gly Ala Gly Asp Asp Asp
            355                 360                 365

Asp Ser Asp Asn Asp Leu Arg Ser Pro Leu Met Ser Arg Gln Thr Thr
        370                 375                 380

Ser Met Asp Lys Asp Met Ile Pro His Pro Thr Ser Gly Ser Thr Leu
385                 390                 395                 400

Ser Met Arg Arg His Ser Thr Leu Met Gln Gly Asn Gly Glu Ser Ser
                405                 410                 415

Met Gly Ile Gly Gly Gly Trp His Met Gly Tyr Arg Tyr Glu Asn Asp
            420                 425                 430

Glu Tyr Lys Arg Tyr Tyr Leu Lys Glu Asp Gly Ala Glu Ser Arg Arg
            435                 440                 445

Gly Ser Ile Ile Ser Ile Pro Gly Gly Pro Asp Gly Gly Ser Tyr
        450                 455                 460

Ile His Ala Ser Ala Leu Val Ser Arg Ser Val Leu Gly Pro Lys Ser
465                 470                 475                 480

Val His Gly Ser Ala Met Val Pro Pro Glu Lys Ile Ala Ala Ser Gly
                485                 490                 495
```

Pro Leu Trp Ser Ala Leu Leu Glu Pro Gly Val Lys Arg Ala Leu Val
            500                 505                 510

Val Gly Val Gly Ile Gln Ile Leu Gln Gln Phe Ser Gly Ile Asn Gly
        515                 520                 525

Val Leu Tyr Tyr Thr Pro Gln Ile Leu Glu Arg Ala Gly Val Asp Ile
        530                 535                 540

Leu Leu Ser Ser Leu Gly Leu Ser Ser Ile Ser Ala Ser Phe Leu Ile
545                 550                 555                 560

Ser Gly Leu Thr Thr Leu Leu Met Leu Pro Ala Ile Val Val Ala Met
            565                 570                 575

Arg Leu Met Asp Val Ser Gly Arg Arg Ser Leu Leu Leu Trp Thr Ile
            580                 585                 590

Pro Val Leu Ile Val Ser Leu Val Val Leu Val Ile Ser Glu Leu Ile
            595                 600                 605

His Ile Ser Lys Val Val Asn Ala Ala Leu Ser Thr Gly Cys Val Val
            610                 615                 620

Leu Tyr Phe Cys Phe Phe Val Met Gly Tyr Gly Pro Ile Pro Asn Ile
625                 630                 635                 640

Leu Cys Ser Glu Ile Phe Pro Thr Arg Val Arg Gly Leu Cys Ile Ala
                645                 650                 655

Ile Cys Ala Met Val Phe Trp Ile Gly Asp Ile Ile Val Thr Tyr Ser
            660                 665                 670

Leu Pro Val Leu Leu Ser Ser Ile Gly Leu Val Gly Val Phe Ser Ile
            675                 680                 685

Tyr Ala Ala Val Cys Val Ile Ser Trp Ile Phe Val Tyr Met Lys Val
            690                 695                 700

Pro Glu Thr Lys Gly Met Pro Leu Glu Val Ile Thr Asp Tyr Phe Ala
705                 710                 715                 720

Phe Gly Ala Gln Ala Gln Ala Ser Ala Pro Ser Lys Asp Ile
                725                 730

```
<210> SEQ ID NO 10
<211> LENGTH: 3231
<212> TYPE: DNA
<213> ORGANISM: Arabidopsis thaliana

<400> SEQUENCE: 10 tcaaatcat ttcgtttcaa caaaaatatg tattttatcc atagagaaac aacaaacctt    60
acactatata ccctcttta acgtgcccac ttttcattat ttacacaatt tccccaacaa   120
atttaaaaca atttacaaaa agcactcaac tttcctaaag tagattcctt tagtccaatg   180
gaattcttac aacatcttct tcttcgccac cttttctct ccactttaag cttttcact    240 ctctctacgc cacgacgact gtgaagcgag aaatggctac ttccgatcaa gatcgccgtc   300
acagagtcac tcgcaaccgt ccaccaatag ctcgaccctc tacttcttca tctcgtcccg   360
ttgtatctcc tcctagatca aaagtttcga agcgtgtgct ctccgtgta gcttccgtcg   420 catgcgggat tcaattcgga tgggctcttc agctttctct cctcacacct tacgttcaag   480
agctggggat cccacacgct tgggctagtg tgatttggct ttgcggtcct ctctctggtt   540
tgttcgtgca accgctcgtt gggcatagta gcgataggtg tactagtaag tacggtcgtc   600
ggagaccgtt tattgtcgcc ggagctgtgg cgatttctat ctctgttatg gttattggtc   660
atgcggcgga tattgatgg gcatttgggg atagagaagg gaagattaag ccgagggcga   720
tgttgctttt tgttttaggg tttggattc ttgatgttgc taataatatg actcaaggtc   780
```

```
cttgtagagc tctccttgct gatcttactg gtaaagttcc tgactttagt gttgattggg      840
tcttcaattt gaaatcattc aaatgtagta aatttgggat tctcgtgatt atacactcac      900
atgcaaaaca tgaaaatgca taaatttgtg attttggata caatttgggg ttatataatt      960
acctaattgg ttcctaacaa tcaaaaggtc ccttctttgt ttctggtcgg tggcttatcg     1020
ttgagtcaca gagactttgt tttttctctt tcccttgaat caaattgtgg attttggtga     1080
agttaatcgt agcctacgat tgtgtgataa cctcatggag tgaaaacaaa gatatgttgt     1140
gttttaattc ttgtcctatt gctttatttt cagagaatga taatcgcaga acccgagttg     1200
caaatggcta cttctctctc tttatggctg ttggcaatgt tcttggctat gctactggat     1260
catacaatgg ttggtacaag atcttcactt ttacgaagac agttgcatgt aatgtggaat     1320
gtgccaatct caagtctgcc ttctacatag atgttgtctt tattgcaata actacgatcc     1380
taagcgtctc agcggctcat gaggtgccac ttgcttcatt ggcttctgaa gcacatgggc     1440
aaaccagtgg aacagacgaa gcttttcttt ctgagatatt tggaactttc agatattttc     1500
caggaaatgt ttggataatc ttgcttgtta cagcattgac atggattggt tggtttccat     1560
ttattctgtt tgatactgat tggatgggtc gagagatcta tggcggtgaa ccgaacatag     1620
ggacttcata tagtgctggg gtcagtatgg gtgcacttgg tttgatgttg aattctgttt     1680
ttcttggaat cacttctgtg ctcatggaga aactttgcag aaagtggggg gctggttttg     1740
tttgggaat atcaaatatc ttaatggcta tttgctttct tggaatgata atcacctcat      1800
ttgttgcgtc tcaccttggc tacattggcc atgaacaacc tcctgccagc atcgtgtttg     1860
ctgctgtgtt aatctttaca attctgggca ttccattggc ggtaagttta ctcctgtaat     1920
tctgctgtca tgttacttac actattactt atgatatttt gcctgctcat ctgtaacaac     1980
atgatgaaat ttatttacgc tttcgctgta actaatgcta ttgctactct tctgcagata     2040
acttacagcg tcccatatgc gttgatttcc atacgtattg aatccctggg cttaggtcaa     2100
ggtgtgcagg cttatctttg ggtgttgttt cttataaaag ttctgttgtg ttgtttctta     2160
gaaaagttct gctcaatgat tttactctac atatgagtgt tgtttcttat aaaagttctg     2220
ttgtggcagg cttatctttg ggtgtgctaa atttggcgat agtcatccca caggtacact     2280
tctttcaacc atccttttag cattatattt gccgcaactc aaaatcatat tcttctttga     2340
atgtttctgc ctgtaaaagg aagtctataa gcataacatg cagcagagtt actgcattat     2400
ttgtcaattg tcattaataa acgattcgtt tttttagtta tggtcattgg ccagtgatga     2460
aagtacactt tttatttctc tatattagtt gattgatgaa tttcttccct atgttggtta     2520
tggtttttgg catcaaactc aaattctgtt gttcaatcat ttatgtgttt gcaggtaatt     2580
gtgtctgttg gcagtggccc atgggatcaa ctgtttggag gtgggaattc accggcactt     2640
gcagtaggag cagctacagg cttcattggc ggaattgtag ctatcttggc tcttccacgg     2700
acaaggattc agaagcccat ccctctccca tgagattctc tcttttgtta tataaggtaa     2760
taatgtcaca attctttcac aaaaagtaca tagtaagcac ttaagttgtc actgattatt     2820
aaaagcggct aatgcgaaat agatgagtgt caagcgagga acgcataagg ggagtgcttg     2880
gaaatggcaa ggagatggaa cacttaatgt gatccttgtc gaaaattcgt gcaatggctt     2940
ctcgtgtgac taacttattt gcagctacta ggacttaatc ccctctactt tggggactat     3000
gatccttgta tacacgaggc accatagaac caatgaaaat aatacatcat tcagtttgtg     3060
aggtatatgc atctctcctt tattggaagt tccagttcgg gatcttctct gttttttttg     3120
ttgttgttgt aaattaatgt aaaaacctgt gtacaacaga gtgtttgtaa gggcccctga     3180
```

```
gttctgtaac tgtttataaa gttcattttc tttagaatta gtttgataaa g        3231
```

<210> SEQ ID NO 11
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of AtSUT4/SUC4

<400> SEQUENCE: 11

```
atggctactt ccgatcaaga tcgccgtcac agagtcactc gcaaccgtcc accaatagct    60
cgaccctcta cttcttcatc tcgtcccgtt gtatctcctc ctagatcaaa agtttcgaag   120
cgtgtgcttc tccgtgtagc ttccgtcgca tgcgggattc aattcggatg ggctcttcag   180
ctttctctcc tcacacctta cgttcaagag ctggggatcc cacacgcttg gctagtgtg    240
atttggcttt gcggtcctct ctctggtttg ttcgtgcaac cgctcgttgg gcatagtagc   300
gataggtgta ctagtaagta cggtcgtcgg agaccgttta ttgtcgccgg agctgtggcg   360
atttctatct ctgttatggt tattggtcat gcggcgata ttggatgggc atttggggat    420
agagaaggga agattaagcc gagggcgatt gttgcttttg ttttagggtt ttggattctt   480
gatgttgcta ataatatgac tcaaggtcct tgtagagctc tccttgctga tcttactgag   540
aatgataatc gcagaacccg agttgcaaat ggctacttct ctctctttat ggctgttggc   600
aatgttcttg gctatgctac tggatcatac aatggttggt acaagatctt cactttttacg   660
aagacagttg catgtaatgt ggaatgtgcc aatctcaagt ctgccttcta catagatgtt   720
gtctttattg caataactac gatcctaagc gtctcagcgg ctcatgaggt gccacttgct   780
tcattggctt ctgaagcaca tgggcaaacc agtggaacag acgaagcttt tctttctgag   840
atatttggaa ctttcagata ttttccagga atgtttggaa taatcttgct tgttacagca   900
ttgacatgga ttggttggtt tccatttatt ctgtttgata ctgattggat gggtcgagag   960
atctatggcg gtgaaccgaa catagggact tcatatagtg ctggggtcag tatgggtgca  1020
cttggtttga tgttgaattc tgttttttct tggaatcactt ctgtgctcat ggagaaactt  1080
tgcagaaagt gggggggctgg ttttgtttgg ggaatatcaa atatcttaat ggctatttgc  1140
tttcttggaa tgataatcac ctcatttgtt gcgtctcacc ttggctacat ggccatgaa    1200
caacctcctg ccagcatcgt gttgctgct gtgttaatct ttacaattct gggcattcca   1260
ttggcgataa cttacagcgt cccatatgcg ttgatttcca tacgtattga atccctgggc   1320
ttaggtcaag gcttatcttt gggtgtgcta aatttggcga tagtcatccc acaggtaatt   1380
gtgtctgttg gcagtggccc atgggatcaa ctgtttggag gtgggaattc accggcactt   1440
gcagtaggag cagctacagg cttcattggc ggaattgtag ctatcttggc tcttccacgg  1500
acaaggattc agaagcccat ccctctccca tga                                 1533
```

<210> SEQ ID NO 12
<211> LENGTH: 510
<212> TYPE: PRT
<213> ORGANISM: Arabidopsis thaliana

<400> SEQUENCE: 12

```
Met Ala Thr Ser Asp Gln Asp Arg Arg His Arg Val Thr Arg Asn Arg
1               5                   10                  15
```

```
Pro Pro Ile Ala Arg Pro Ser Thr Ser Ser Arg Pro Val Val Ser
            20                  25                  30

Pro Pro Arg Ser Lys Val Ser Lys Arg Val Leu Leu Arg Val Ala Ser
        35                  40                  45

Val Ala Cys Gly Ile Gln Phe Gly Trp Ala Leu Gln Leu Ser Leu Leu
    50                  55                  60

Thr Pro Tyr Val Gln Glu Leu Gly Ile Pro His Ala Trp Ala Ser Val
65                  70                  75                  80

Ile Trp Leu Cys Gly Pro Leu Ser Gly Leu Phe Val Gln Pro Leu Val
                85                  90                  95

Gly His Ser Ser Asp Arg Cys Thr Ser Lys Tyr Gly Arg Arg Arg Pro
            100                 105                 110

Phe Ile Val Ala Gly Ala Val Ala Ile Ser Ile Ser Val Met Val Ile
            115                 120                 125

Gly His Ala Ala Asp Ile Gly Trp Ala Phe Gly Asp Arg Glu Gly Lys
        130                 135                 140

Ile Lys Pro Arg Ala Ile Val Ala Phe Val Leu Gly Phe Trp Ile Leu
145                 150                 155                 160

Asp Val Ala Asn Asn Met Thr Gln Gly Pro Cys Arg Ala Leu Leu Ala
                165                 170                 175

Asp Leu Thr Glu Asn Asp Asn Arg Arg Thr Arg Val Ala Asn Gly Tyr
            180                 185                 190

Phe Ser Leu Phe Met Ala Val Gly Asn Val Leu Gly Tyr Ala Thr Gly
        195                 200                 205

Ser Tyr Asn Gly Trp Tyr Lys Ile Phe Thr Phe Thr Lys Thr Val Ala
210                 215                 220

Cys Asn Val Glu Cys Ala Asn Leu Lys Ser Ala Phe Tyr Ile Asp Val
225                 230                 235                 240

Val Phe Ile Ala Ile Thr Thr Ile Leu Ser Val Ser Ala Ala His Glu
                245                 250                 255

Val Pro Leu Ala Ser Leu Ala Ser Glu Ala His Gly Gln Thr Ser Gly
            260                 265                 270

Thr Asp Glu Ala Phe Leu Ser Glu Ile Phe Gly Thr Phe Arg Tyr Phe
        275                 280                 285

Pro Gly Asn Val Trp Ile Ile Leu Leu Val Thr Ala Leu Thr Trp Ile
290                 295                 300

Gly Trp Phe Pro Phe Ile Leu Phe Asp Thr Asp Trp Met Gly Arg Glu
305                 310                 315                 320

Ile Tyr Gly Gly Glu Pro Asn Ile Gly Thr Ser Tyr Ser Ala Gly Val
                325                 330                 335

Ser Met Gly Ala Leu Gly Leu Met Leu Asn Ser Val Phe Leu Gly Ile
            340                 345                 350

Thr Ser Val Leu Met Glu Lys Leu Cys Arg Lys Trp Gly Ala Gly Phe
        355                 360                 365

Val Trp Gly Ile Ser Asn Ile Leu Met Ala Ile Cys Phe Leu Gly Met
370                 375                 380

Ile Ile Thr Ser Phe Val Ala Ser His Leu Gly Tyr Ile Gly His Glu
385                 390                 395                 400

Gln Pro Pro Ala Ser Ile Val Phe Ala Ala Val Leu Ile Phe Thr Ile
                405                 410                 415

Leu Gly Ile Pro Leu Ala Ile Thr Tyr Ser Val Pro Tyr Ala Leu Ile
            420                 425                 430

Ser Ile Arg Ile Glu Ser Leu Gly Leu Gly Gln Gly Leu Ser Leu Gly
```

```
                435                 440                 445
Val Leu Asn Leu Ala Ile Val Ile Pro Gln Val Ile Val Ser Val Gly
        450                 455                 460

Ser Gly Pro Trp Asp Gln Leu Phe Gly Gly Gly Asn Ser Pro Ala Leu
465                 470                 475                 480

Ala Val Gly Ala Ala Thr Gly Phe Ile Gly Ile Val Ala Ile Leu
                    485                 490                 495

Ala Leu Pro Arg Thr Arg Ile Gln Lys Pro Ile Pro Leu Pro
            500                 505                 510

<210> SEQ ID NO 13
<211> LENGTH: 4595
<212> TYPE: DNA
<213> ORGANISM: Beta vulgaris
<220> FEATURE:
<221> NAME/KEY: modified_base
<222> LOCATION: (3190)..(3190)
<223> OTHER INFORMATION: a, c, g, or t

<400> SEQUENCE: 13
ctcctacctt aatttctctt tcattttcc acatacacaa acttgttcac aatttgagtt      60
tgtttccttt aaagaagcaa aatcaaacat tcttctgttt tcccttcata tttcttttag    120
ttcatctctc aataaaaaaa aaaaaacaga gaaaagatac ataaaatgaa tattgctcat    180
tttatcttcg gagtttttgg tgggtatttt cttcaattt tatttgttca ttttttttgtg    240 tggtgtaatt tgaagatagc atgaatttat ttcttgattt ttatgtttca tgcaggaaat    300
gcaactgctc tgttcctctt cttggctcct gtgtaagtag ttttttttgaa gagaaaaaaa    360 cctactaatt ttttcttgaa attttaagtg ggtttccatt tttattcact gtaatccagt    420
aatttatttc aaaagaaaag cgaagaaaac acatttttt tcttaagatt agtgggtttt    480
catttatatt cactataatc cagtaatttt ctcgaaattt ctcggtttct tgctgttttt    540
ttatctgaat ttggtgactg aagcaaattc caatgtttgt tcttcgcatt ctttcacatt    600
gtttggtcat tttcttgttc catgtgtttt ttgggacaat tttggccttt tcttttacaa    660
aagtacacaa ttattttttc tcaaaattat gcttcaatca tgaatttat attccttttt    720 tctccaaaaa tatgaaattt aattttgtgg ggctttcttc gattaacatc taatgaagat    780
tataggtggg aattaattt tgtgagtttgc tatcaaatat atttatgaca gtgtgacatt    840
taagaggatc ataaagaaca aatcaaccga gcaattctca ggaattccat atgtcatgac    900
cttgctcaac aacctgcttt ctgcatggta acttcccctat tccctacttt tcttcaactt    960
cttacctttt ctttccttaa tccatttaaa taactattaa ttattaaatt attgttgtta   1020
ctatttcttt cctataatgg tttactatat cttcctata atgggtgtag tgctacttgc   1080
aaaatcatta ttgcgttata cttcttctat ttttttaacc ttgagcagat taaaataatc   1140
aaatgttatt aatatcatgt gaaatcactg tgaagtacaa gtaaaaagtt tcacctaacg   1200
gctcatctta ctccacttga gttctactag agtataggtt ggtggttgcc ctagtgtcat   1260
ctgtcatgga tgatgtaata tcttcgattg ctaatagcta acaaaacaaa cactttgagc   1320
ttttgtgaat gaataatgtg gatgtagatc aatgttaaag ttaaactaca caagtaaatt   1380
tgcatattca aatatgaaac atgggtacac aatttgacat ttttagaac taaaaatttg    1440 ctcaaatggg agtttttttc accactttat aatatcttca ttctctatat tggctaatgt   1500
tttgaattgc tgaaattaat tagccgctaa tcatgtttct taagtaaatc tactttgaca   1560
gtgactgtca tttatcctat tttgggtgct ttatattgat taatcaaagt cttctaatta   1620
```

| | |
|---|---|
| tatcctttac tatgaaagaa ttggtcaaat ttactaaact gtttgaaatt atacaaaaac | 1680 |
| aggtatggac tccctttgt gtccccaaac aacatactag tgacaacaat caatggaact | 1740 |
| ggtgctgtaa ttgagagtgt atatgtgtta attttctga tattggctcc cagaaaggag | 1800 |
| aaggttaaga tcggtggcct tcttgctatc attctttcta ttttcgcaat tgtcgcgctt | 1860 |
| gtttcactcc ttgctcttca tgacaccaaa aggaaggttt tctgtggggt tgcagctagt | 1920 |
| gttttctcca ttatcatgta tggttcccct ctttctatca tggtaagtct aattttctg | 1980 |
| atatagtttt accacttcaa tatttccgat gttctctctt agctgcaaca cggcacttgg | 2040 |
| acaatatata tcaatatatg ttcgattgtc tataagtaaa aatcatgaga agttcagatt | 2100 |
| ttgagattat acatacacac aaatctaaca agatatcaca aaatttgctt ttgcacgtgt | 2160 |
| aaatcacaaa atatggtcaa aatggagtag gaggatggtg ccaaaagtca aattggtaga | 2220 |
| agtaaaaaaa attatggagg taataagtat gattagtatt gttaatgatg aactagtgca | 2280 |
| tgtaatgatg atctctttaa aggaaatctg ttagagcttg taattctgcg ttaaatgtaa | 2340 |
| tcgcactatg tggtggttgg aaatgggctg caattagggt aagaggttgc ttatgtctaa | 2400 |
| gatgctgata tattgatcaa aagatttgta gacctctttt tctttctttt tggaattcct | 2460 |
| tatacaacag ggtaatttga ttaatttaga aggaaaacat atcaatcttt gcacctaata | 2520 |
| taggtagtga atatatatat agaatatttc tggacttaat tcactcctat gtttactttg | 2580 |
| tataattggt atactatttg tctcacaatt gggatttaat tgtttacgta gaggttggtg | 2640 |
| atcaagacaa agagtgtgga gtacatgccc ttcttgctat cactcttctg tttcttgtgt | 2700 |
| ggtacatctt ggtttatttt cggattaatt ggccgcgatc cattcattgc tgtaagtatt | 2760 |
| tcataattat agattgtcat aaactaatct atttgttatt tgtcgagtaa atagtaattt | 2820 |
| cctctggaga ttttgggttg tttatgagta ggtggttcat tttatcaggc gattaaagat | 2880 |
| ataatgtttg taagctatac tagaagaagt ttgttagtgc tacagtagtc actaatgata | 2940 |
| gagatttcat cacattacac ctcaaagagt atgaagtatt ttcttttatg tttgtgggtt | 3000 |
| cctacttcct atcattgtct ttgattggtg atcactcatt cactttgtgt gtgctttgtt | 3060 |
| gcttccaatt gttgaacgtc ttaaaagttc tggtggtgat gtatgtaaat ctttaacata | 3120 |
| ggcaacagta caagaaagat gttttcctaa cgcataatcg atcacgaata ataatccgac | 3180 |
| taaaattatn gtaagtattt ttcttttatc gtttgtgggg ttcctacttc ctatcattgt | 3240 |
| ctttgattgg tgatcactca ttcacttgtg tgtgctttgt tgcttccaat tgttgaacgt | 3300 |
| cttaaaagtt ctggtggtga tgtatgtaaa tctttaacat aggcaacagt acaagaaaga | 3360 |
| tgttttccta acgcataatc gatcacgaat aataatccga ctaaaattat gcacctagga | 3420 |
| cttaggagca tgaggttgca atttgcaaca tgtatttgat gaatgttctt ttcatcattc | 3480 |
| ccgcatgttt tagttttatc attaatatag taatattgtc tttatatttt cctattgtga | 3540 |
| actgtatata tttataaaga cgagttgata atttaattt gaagctattg attcttttac | 3600 |
| ttcacttgtc ccttaaccaa ttggtcgaga gttcgatcct caacctttgg gaatggaaag | 3660 |
| agattcttga ccaaccctt accctta agt ggagcacctg gggcgagggg ataagtcact | 3720 |
| gctatcggcg atggatacct tggttgttca cccaaaaaaa aaaagaatg tgatctggag | 3780 |
| tgaatgatgc atatcatgct cttgggtgta ggatcaatcc cccccccac cccctcttag | 3840 |
| gttgtttgag tcgtgcttac taatagttac taaaaccaaa agtgtagtga ttttctaaag | 3900 |
| cactaaacat ataaatgggt gaagcatagg gtaatttgct agccgattac accaattata | 3960 |

-continued

```
gatcaccaaa tgatacacga aatagagttt acacaagata tatatagaat tttgttgttg    4020
tattgtcaca tataaaaatc tcctatgata taatttccaa atataggatt gtattttcac    4080
atatctatga tataatttcc aaatatagaa tttgactaaa taattaaatt atgctttatg    4140
atattggcag gtacctaatg gttttggaag tgcattagga gcaatgcagc tgatcctata    4200
tttcatttac tatgacaaaa atcctgaaga aaagaaaaag actacaactg atcatggtgt    4260
tgagttgggc ctaaatggaa atggaaaggc ccaccataat atccaagatg gcaagtccaa    4320
cactcaacct tcgattaatg ggcacgtctg atatatctta tgtgtcatca tgcctttacc    4380
acagcacatt gattgatgat gaactgatcc tttgcaatta ttttcgtatc tttcttttga    4440
gggcttattc ttgtagttat ctctcgctgt cgctgtcgct gtcgcttttg cttttgatta    4500
tgcttatgct tatgcttagg ttttattatc atcgtaattg caagtgtaaa catgttgatg    4560
atcttgtgtt gggaatgggc aattcagcta agaca                               4595
```

<210> SEQ ID NO 14
<211> LENGTH: 768
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of BvSWEET (candidate which has been
      upregulated upon cold)

<400> SEQUENCE: 14

```
atgaatattg ctcattttat cttcggagtt tttggaaatg caactgctct gttcctcttc     60
ttggctcctg ttgtgacatt taagaggatc ataaagaaca aatcaaccga gcaattctca    120
ggaattccat atgtcatgac cttgctcaac aacctgcttt ctgcatggta tggactccct    180
tttgtgtccc caaacaacat actagtgaca acaatcaatg gaactggtgc tgtaattgag    240
agtgtatatg tgttaatttt tctgatattg gctcccagaa aggagaaggt taagatcggt    300
ggccttcttg ctatcattct ttctattttc gcaattgtcg cgcttgtttc actccttgct    360
cttcatgaca ccaaaaggaa ggttttctgt ggggttgcag ctagtgtttt ctccattatc    420
atgtatggtt cccctctttc tatcatgagg ttggtgatca agacaaagag tgtggagtac    480 atgccttct  tgctatcact cttctgtttc ttgtgtggta catcttggtt tattttcgga    540
ttaattggcc gcgatccatt cattgctgta cctaatggtt ttggaagtgc attaggagca    600
atgcagctga tcctatattt catttactat gacaaaaatc ctgaagaaaa gaaaagact    660 acaactgatc atggtgttga gttgggccta aatggaaatg gaaaggccca ccataatatc    720
caagatggca agtccaacac tcaaccttcg attaatgggc acgtctga                 768
```

<210> SEQ ID NO 15
<211> LENGTH: 255
<212> TYPE: PRT
<213> ORGANISM: Beta vulgaris

<400> SEQUENCE: 15

```
Met Asn Ile Ala His Phe Ile Phe Gly Val Phe Gly Asn Ala Thr Ala
  1               5                  10                  15

Leu Phe Leu Phe Leu Ala Pro Val Val Thr Phe Lys Arg Ile Ile Lys
                 20                  25                  30

Asn Lys Ser Thr Glu Gln Phe Ser Gly Ile Pro Tyr Val Met Thr Leu
             35                  40                  45
```

```
Leu Asn Asn Leu Leu Ser Ala Trp Tyr Gly Leu Pro Phe Val Ser Pro
 50                  55                  60

Asn Asn Ile Leu Val Thr Thr Ile Asn Gly Thr Gly Ala Val Ile Glu
 65                  70                  75                  80

Ser Val Tyr Val Leu Ile Phe Leu Ile Leu Ala Pro Arg Lys Glu Lys
                 85                  90                  95

Val Lys Ile Gly Gly Leu Leu Ala Ile Ile Leu Ser Ile Phe Ala Ile
            100                 105                 110

Val Ala Leu Val Ser Leu Leu Ala Leu His Asp Thr Lys Arg Lys Val
            115                 120                 125

Phe Cys Gly Val Ala Ala Ser Val Phe Ser Ile Ile Met Tyr Gly Ser
130                 135                 140

Pro Leu Ser Ile Met Arg Leu Val Ile Lys Thr Lys Ser Val Glu Tyr
145                 150                 155                 160

Met Pro Phe Leu Leu Ser Leu Phe Cys Phe Leu Cys Gly Thr Ser Trp
                165                 170                 175

Phe Ile Phe Gly Leu Ile Gly Arg Asp Pro Phe Ile Ala Val Pro Asn
            180                 185                 190

Gly Phe Gly Ser Ala Leu Gly Ala Met Gln Leu Ile Leu Tyr Phe Ile
            195                 200                 205

Tyr Tyr Asp Lys Asn Pro Glu Glu Lys Lys Lys Thr Thr Thr Asp His
210                 215                 220

Gly Val Glu Leu Gly Leu Asn Gly Asn Gly Lys Ala His His Asn Ile
225                 230                 235                 240

Gln Asp Gly Lys Ser Asn Thr Gln Pro Ser Ile Asn Gly His Val
                245                 250                 255

<210> SEQ ID NO 16
<211> LENGTH: 4441
<212> TYPE: DNA
<213> ORGANISM: Beta vulgaris

<400> SEQUENCE: 16
ttcctcagat tagaattttc aggtgtttct ttctgataga ctcaacacaa gtttctgtca      60
cccccaataa accttggaaa acaaagcaag agagggagct aagtttaata gtagagaact     120
aaaaaaaaaa agagagaagg aaatccccaa atacaaaaaa gagagaaatt catattaccc     180
aatattcaag ccatgtttac catccaccac ccatgggttt ttgcctttgg cctactaggt     240
atatactatc ctttattttt taaacattaa gttttagctc attaagcaat ataagtgtct     300
ctatctttat aaacatataa agaaaaccgt tttattaatt caattaccat agttttagat     360
gagaaaaaac aatcagtttt tcctaaagta acgaaaaatc tcgtttctac aagagtgaaa     420
agtgtagttc cttctttttt tctattcatt tcgcattggt ctatctatct cttggtacac     480
ttggatagat gtaacaagtg catgtttctc ttccatcatt catattaatt ttcttaatca     540
tgcatgcttt tggttggggt gttacaagtt tcagggcaag tgggcaacag tgcatgttat     600
tgcgttatca acgtaagaag gcgcgctatt tctatatcaa agatggcaat ttacgttgtc     660
tgatcctcat tgatgtaacc tgtagtatat tatagtttta aaggaaaacc gctattaaaa     720
acaaacaatc ttgttatatc tttcctagca actgatataa caaatagatc ttttattgag     780
gtgtaccaaa aatttaattc aacaacattc acaaagtatt ctaaaaggtt attgaaatga     840
tcttcatgta tatataaatg gccgaaacta tgtatattaa tattttttc ttcttacata     900 aaatttcctt ctaaattgaa cagaattcac ctgaaaatat tgtcattctt tattaaccca     960
```

```
cctcatgata atattattac ttaagtttga tcaatcaatt aagctttgga tcacaaggac    1020
taatcatttt tgtcaccttg tgtgatccta ttatgttgca ggcaacgtca tctctttcat    1080
ggtgtttctt gcaccactgt aagtattatt ttatcattat agtattcctg ttcattaatt    1140
cttttcactt agacgtttac tttgtccctt ttcatatgca tgaaatatag ttaatcctag    1200
aatttatatt gttattataa gataacacca ctaagtagag actgtatatt ctaatcatac    1260
ttttaatgat agtgctaaag ttgatttgat taaatttatc aatcgatatt acaggccaac    1320
ttttatacgg gtgtacaaga aaaaatcaac agaaggattc caatcagtac cctatgtcgt    1380
agcaatcttc agtgccatgt tatggatcta ctatgcattg ttgaagggca attctgtcct    1440
tctaatcacc atcaatgttg ctggagttat tattgagacc atttacgttg ccatatacat    1500
tacctatgca ccaaggcaag caagggtacg tatgataggt tattgacata tcatcaagac    1560
atcaacgtac cattatttac tgtaccaaga aaagaggtgt atttgataaa tatagactaa    1620
actatggatc atcgaaggtg ataataaagt aactgtactc aaactaagaa aaggaaaaga    1680
ctgaaagtct gaattacata cataatgcta tttgttcggc acttccaaaa cttaatattt    1740
caacttgaag tcactacctt tagttctatt aacatgattt gattttttgat ctatgtttgt    1800 cagttttctct aatgaaatat tatatatatt atcatatata aattatcatt ccatgcatct    1860
gcaagtaata tatattcaac acagtaacat aataaaagtg gctgggctag tcaattttc    1920 aaataaaagt taagattttt ctattattat agttactatt tatttattat tgttattgtt    1980
gttgttgtta atgcttataa ttatacaaat aaattgttta ctctctaaaa aacgctaaaa    2040
aacctagtat ttgggaaaca ttttgattgt tatcatactg cattcacgtg gcattcacaa    2100
gtgttagcaa ttttaaaaac attatcggtg gtatatttta taagcggatc tacaggggta    2160
caaggggtat tatatctcca ttatttctgg aaaataataa aaacaaaata atatggtaag    2220
gcttgtcatg ctggcagcag aaagaaaaag aaagatacat gaattcatga aaagatcttg    2280
agttcgaaat cccacaaagt ttttttttttg cttttaatta ttaactcagg tttaattttat    2340 cttcaagact tctacagttc tactatatac tattccctat gagcctatgg ctattagtct    2400
gcaactaaaa atttagaagt aataaaattt ataagtaaga ttactctgca accacaaatt    2460
cataagccca caaagatcaa agcttcaaaa taatatcttt atctctatta tttttccctca    2520 aattttcctc gttatatatc ttaaacaatt gttttttaaag tgaacaactt attttttaaag    2580 tcgtggttat ttaaattgaa atattgaacg attaaatagc tagcaatcat atctaagttc    2640
ttactcaaac ttatgaagac aaaaatattg acaaagcttt attttttaaa aaaattaaca    2700
aatctaacta ctaacatatt catatatccta tgagtaaatt cctaggtatg tcagtggact    2760
acattcggct taatttcacc tcataacctt atgtgattac tcgttttttgc agatatcgac    2820 actgaagcta cttttgttca tgaattttttg cgggttttgt acaattgtcc tcttctgcca    2880
ttacttagtt aaagcggaaa atcgacttca agttttcgga tggatatgcg tcgcgttctc    2940
tattagtgta tttgctgcac ctttgagtgt aatggtaagt gaatcattat acctaaccaa    3000
agctaaaaaa atctccaaac aaacattttt gttaactctt cactctcgaa ttaaaccttt    3060
agcacttcac ttatcaaata tcaatttgtt ttttttacag aggacagtaa taagcacaaa    3120
gagcgtggaa tacatgccaa ttaacttgtc cataagtctc acattaaccg ctactatatg    3180 gttttttgtat ggatttgtcc agaaagatct ttacatcaca gtaagtccaa ttttatacat    3240
ataaaaccat aaatttgcatt atatttatgt ttttgagata aagattaagc gtcccttctc    3300
tcaagggaaa ggccaaaacc atatgtttta atttgcgtta tatgcttatt gatatatgct    3360
```

```
agatttcggg tcaattccct taatcggagt gtgttcattg atcattaata tatataggtt    3420
tacaataaat catatccgaa atacaatcgg actatgcaaa gtatatctaa tacaaaaata    3480
ttaaagataa tattttcata ttctatcaat atatacttga ttactaccaa ggatgttttg    3540
gcctaatgat taagactagg tgctgtgaac gatagggcac acattcgaat ccccttccc     3600 cttctttgtt tgtactgcct tcgtggttca tatggatcaa tatatatata tactagatta    3660
cttaattact atattattaa tcatacttat ttgttcatat tttgcaaaaa aaaaaaatgg    3720
cagcttccaa atgttgtggg gttcatgttt ggtgtggcac aaatgggatt atattcaata    3780
tacaggaaat atgacataaa agctaaaaaa gagaagctac cagaagttgc aagtccagtg    3840
aagcaagaaa cagtcgagat agatacaata aattccagtc ctaacaaaac agaatctgag    3900
gattatattc ctccacatga gaaaactcca gaaattgagg ttgtagttac tggaaacaaa    3960
gatgatgata ttgatgatga gcaactgggt aataaagacc accaagaata tttatatggg    4020
ccgccacaag gcccatcaaa atgcaacgtg gatgtcgaca aggttgttgg tgggccagca    4080
cccggcccaa cttctgttca attggttcag tgtgccgttt gaagtagggc atttgatatt    4140
agtttctaag cttttgggtt tgttacccat tttgttctta ccccttaacg cccaatccct    4200
tcagaataag ggcattggaa aaaaaaatta gatttgggtt agatatgtaa atttgggaag    4260
gccttttgtg gggtcgactc tgatgaatga agggcatcag gagtttgatt agaggatcat    4320
atcattatat cccaccgctt ctcttgtatg tttgttcctg atcttctgaa aatccctcaa    4380
aggttccttt aattattatt gtagtatgtc tcttttcct caattaatgg aattttgttt       4440
t                                                                    4441
```

<210> SEQ ID NO 17
<211> LENGTH: 975
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of BvSWEET (candidate which has been
      upregulated upon cold)

<400> SEQUENCE: 17

```
atgtttacca tccaccaccc atgggttttt gcctttggcc tactaggcaa cgtcatctct      60
ttcatggtgt ttcttgcacc actgccaact tttatacggg tgtacaagaa aaaatcaaca     120
gaaggattcc aatcagtacc ctatgtcgta gcaatcttca gtgccatgtt atggatctac     180
tatgcattgt tgaagggcaa ttctgtcctt ctaatcacca tcaatgttgc tggagttatt     240
attgagacca tttacgttgc catatacatt acctatgcac caaggcaagc aaggatatcg     300
acactgaagc tactttttgtt catgaatttt tgcgggtttt gtacaattgt cctcttctgc    360
cattacttag ttaaagcgga aaatcgactt caagttttcg gatggatatg cgtcgcgttc    420
tctattagtg tatttgctgc acctttgagt gtaatgagga cagtaataag cacaaagagc    480
gtggaataca tgccaattaa cttgtccata agtctcacat taaccgctac tatatggttt    540
ttgtatggat ttgtccagaa agatctttac atcacacttc caaatgttgt ggggttcatg    600
tttggtgtgg cacaaatggg attatattca atatacagga aatatgacat aaaagctaaa    660
aaagagaagc taccagaagt tgcaagtcca gtgaagcaag aaacagtcga gatagataca    720
ataaattcca gtcctaacaa aacagaatct gaggattata ttcctccaca tgagaaaact    780
```

-continued

```
ccagaaattg aggttgtagt tactggaaac aaagatgatg atattgatga tgagcaactg    840
ggtaataaag accaccaaga atatttatat gggccgccac aaggcccatc aaaatgcaac    900
gtggatgtcg acaaggttgt tggtgggcca gcacccggcc caacttctgt tcaattggtt    960
cagtgtgccg tttga                                                    975
```

<210> SEQ ID NO 18
<211> LENGTH: 324
<212> TYPE: PRT
<213> ORGANISM: Beta vulgaris

<400> SEQUENCE: 18

```
Met Phe Thr Ile His His Pro Trp Val Phe Ala Phe Gly Leu Leu Gly
1               5                   10                  15

Asn Val Ile Ser Phe Met Val Phe Leu Ala Pro Leu Pro Thr Phe Ile
            20                  25                  30

Arg Val Tyr Lys Lys Ser Thr Glu Gly Phe Gln Ser Val Pro Tyr
        35                  40                  45

Val Val Ala Ile Phe Ser Ala Met Leu Trp Ile Tyr Tyr Ala Leu Leu
    50                  55                  60

Lys Gly Asn Ser Val Leu Leu Ile Thr Ile Asn Val Ala Gly Val Ile
65                  70                  75                  80

Ile Glu Thr Ile Tyr Val Ala Ile Tyr Ile Thr Tyr Ala Pro Arg Gln
                85                  90                  95

Ala Arg Ile Ser Thr Leu Lys Leu Leu Leu Phe Met Asn Phe Cys Gly
            100                 105                 110

Phe Cys Thr Ile Val Leu Phe Cys His Tyr Leu Val Lys Ala Glu Asn
        115                 120                 125

Arg Leu Gln Val Phe Gly Trp Ile Cys Val Ala Phe Ser Ile Ser Val
    130                 135                 140

Phe Ala Ala Pro Leu Ser Val Met Arg Thr Val Ile Ser Thr Lys Ser
145                 150                 155                 160

Val Glu Tyr Met Pro Ile Asn Leu Ser Ile Ser Leu Thr Leu Thr Ala
                165                 170                 175

Thr Ile Trp Phe Leu Tyr Gly Phe Val Gln Lys Asp Leu Tyr Ile Thr
            180                 185                 190

Leu Pro Asn Val Val Gly Phe Met Phe Gly Val Ala Gln Met Gly Leu
        195                 200                 205

Tyr Ser Ile Tyr Arg Lys Tyr Asp Ile Lys Ala Lys Lys Glu Lys Leu
    210                 215                 220

Pro Glu Val Ala Ser Pro Val Lys Gln Glu Thr Val Glu Ile Asp Thr
225                 230                 235                 240

Ile Asn Ser Ser Pro Asn Lys Thr Glu Ser Glu Asp Tyr Ile Pro Pro
                245                 250                 255

His Glu Lys Thr Pro Glu Ile Glu Val Val Thr Gly Asn Lys Asp
            260                 265                 270

Asp Asp Ile Asp Asp Glu Gln Leu Gly Asn Lys Asp His Gln Glu Tyr
        275                 280                 285

Leu Tyr Gly Pro Pro Gln Gly Pro Ser Lys Cys Asn Val Asp Val Asp
    290                 295                 300

Lys Val Val Gly Gly Pro Ala Pro Gly Pro Thr Ser Val Gln Leu Val
305                 310                 315                 320

Gln Cys Ala Val
```

<210> SEQ ID NO 19
<211> LENGTH: 1716
<212> TYPE: DNA
<213> ORGANISM: Beta vulgaris

<400> SEQUENCE: 19

```
tgaactgaac tgttaattat ttcaactaat acaaactgaa ctgatatcaa ctgaactgtt      60
tggttataac cataactgaa ctgttgaact gaattgacac ctctaattgc aacggcaaca     120
atagaactgt tacagtagcc caatctacaa aactaaattg acaagaactg ttgcattaga     180
tactcctact acaacggtac gtaataatgt gttgcactag taaattttag cctttgcctt     240
tgattaaaaa tgttgtagtg acacatcaca ataaaatcaa atctaatgaa tatgctataa     300
acaaacaatt gttccaaaat caactattct tacgaaatac tcttttcgag ggacgacatt     360
tttctgaaac accctaagcg acgttattga ctctaataca tagatgaaat atcaataaaa     420
agggatttat atgaggtatt ctttaatttt tttttaagaa catatgaggt accatagtat     480
tttaaaaatc aatccatgtg cccctaactt cgtaatgtat ccatcatata tatcccttttt     540
ttttttaggg gtccatcata tatatcctta atgcatgact atcaaacatt agatatgtct     600
taatcccccc ctaacaatca accaaaattc caaaattggt tactctattt gttcctatta     660
caccttccac caatctcaac aaattttggc attctggtta agtactcgaa ggactactta     720
acgaaatatt tgatgtttgt tagccattaa ggtttatgtg ttggattcat tataaatggt     780
ttgaaaagtt tattatcatc tttattaaaa gttcaatagt acctcatgag aactctctat     840
aaatcaacta tattagttat caataataag atacattcgg attctatttg gcaacacatt     900
taagtcaccct caaatgaata ggtgttaaaa gtttaagtca cctaaaataa atagtcatga     960
ttaaagtaag agcttaaatc aaatgtaagc taaaaaattg actgaaatta aattggtatc    1020
aagtataaca tcttaattta aggtgttaaa attttcaact aacttatcaa ttgagctttt    1080
ttcatcaatt tcacctctat ttcagctttg tttttagctt atatttccaa aattgccaat    1140
aggtctcatt tatacctaag atattcaaca atcctggctc tcttcctgct cgttcattcc    1200
aaatttccca aatgtaatca gattaaagca gtagtgatcg gatcattgca gacttttcgg    1260
tagaataact gaataagtgt actgagatag tgtcaaaata ctgttattta agttttctat    1320
aagtactaaa atatgaatta gttcaacatc atcttatatt gtcggccaat aagattgccc    1380
actgtataat aatataaaac aaaatcacag aggtgatatc gccttaaaaa aaaaaaatca    1440
tagatgtgaa ttaatgtaac cgagcataaa tcaactgttt cctttttttt taaaagagaa    1500
atcaactgtt tcctagaaac aattgaatat tatatggtgg tttattgttt caaatttcag    1560
aaaaacaaaa aaaaaaaagc ctttgctact tacttacata gttgcatcta tataaagggc    1620
acctagccca accattttac ttacctaaac tgtctgtgtt tgcaccactc tcatctaaaa    1680
aatctgtgaa agtgagcgtt tcaaaatttt caaaag                              1716
```

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
caccatgaca ggccaggacc aaaata                                            26
```

```
<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tacatgcatc acatgaactc tgg                                          23
```

METHOD FOR INCREASING COLD OR FROST TOLERANCE IN A PLANT

CROSS-REFERENCE TO RELATED APPLICATIONS

This application is a U.S. National Phase of International Patent Application No. PCT/EP2020/085835, filed on Dec. 11, 2020, which claims priority to European Application No. 19215963.0, filed Dec. 13, 2019. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 8, 2022, is named 245761_000171_SL.txt and is 116,682 bytes in size.

FIELD OF THE INVENTION

The present invention relates to methods of increasing the cold tolerance of a plant or part thereof and/or preventing or inhibiting bolting of a plant, comprising deregulating the phloem flux in said plant or part thereof. The invention also extends to the use of genes for deregulating phloem flux in a plant or part thereof; and/or increasing cold tolerance of a plant or part thereof; and/or preventing or inhibiting bolting in a plant. The invention also provides methods of selecting and/or producing a plant with deregulated phloem flux and/or increased cold tolerance and/or delayed or inhibited bolting. The invention also extends to constructs, isolated polynucleotides and polypeptides which can be used to deregulate phloem flux, plant cells transformed with such constructs, and to plants or parts thereof having deregulated phloem flux.

The invention also relates to the use of plants or parts thereof having deregulated phloem flux and harvested roots of such plants. In some aspects the invention relates to methods of increasing the sucrose concentration of a sucrose storage organ of a plant.

BACKGROUND

The present invention relates to increasing cold tolerance and/or preventing or inhibiting the bolting of crop plants. In particular, the invention relates to the deregulation of phloem flux and the use thereof for increasing cold tolerance and/or preventing or inhibiting bolting of crop plants. The present invention has particular utility in the field of industrial sugar production from crops.

Sugar is a collective term for all sweet-tasting mono- and disaccharides and is the common commercial name for the disaccharide saccharose. Saccharose is the ordinary household or granulated sugar and is also known as sucrose. Saccharose is a dimer of one molecule of a-D-glucose and -D-fructose, which are interconnected via a-1,2-glycosidic bond.

Saccharose is formed in plants by photosynthesis. Saccharose is a non-reducing disaccharide and is therefore the most important transport sugar in plant, used as nutrient and energy source. Saccharose is synthesized in the leaves of plants and is the primary sugar transported via the phloem from source to sink organs.

After unloading at the sinks, saccharose can be metabolised and used as an energy precursor and as a building block for growth and storage compound biosynthesis. Non-green storage organs like tubers or taproots must maintain a steep source to sink gradient. Imported sucrose is rapidly converted into relatively inert storage compounds like starch or is compartmentalised intracellularly into large cell vacuoles. Sink and source identities of plant organs are dynamic and transitions are initiated in response to endogenous developmental signals or in response to specific environmental stimuli.

Commercially important plants for the production of saccharose are sugar beet (*Beta vulgaris* subsp. *vulgaris*), sugar cane (*Saccharum officinarum*) and sugar palm (*Arenga pinnata*, syn.: *Arenga saccharifera* Labill., mainly in Indonesia). In temperate zones such as Europe and North Africa sugar beet is the major crop species providing industrial sucrose.

Sugar beet is a biennial plant which forms a large taproot during the first year of its development. This taproot contains up to 20% of its fresh weight as sucrose. During the second year, the taproot provides stored sucrose as a precursor for the formation of a large inflorescence. Production of the inflorescence depends on a previous phase of prolonged cold temperatures approximately 2° C. to 10° C., which induces vernalization, the process during a period of cold in which the plant changes from the vegetative to the reproductive stage. Vernalization-dependent bolting leads to a decrease in yield of sucrose. Despite being a biennial plant, sugar beet is grown commercially as an annual plant due to its sensitivity towards frost and because once vernalized, flowering is initiated in sugar beet, which in turn decreases sugar yield at harvest. It is thought that the concomitant loss of taproot sugar may be detrimental for the taproot's tolerance towards frost as sugars are known to protect tissue from frost damage.

A prolonged cultivation period (e.g. from spring to autumn) and identification of bolting resistant varieties are desirable commercially.

Two major early-bolting loci, B and B2 have been identified in the sugar beet genome, encoding the pseudo response regulator gene BOLTING TIME CONTROL 1, BTC1 (Pin et al., 2012 Current Biology 22: 1095-1101, incorporated herein by reference) and the DOUBLE B-BOX TYPE ZINC FINGER protein BvBBX19 (Dally et al., 2014 Proc Natl Acad Sci USA 111: 10365, incorporated herein by reference), respectively. In annual beets, expression of both genes leads to repression of the floral repressor gene FT1, and subsequent induction of the floral inducer gene FT2 and vernalization-independent flowering upon long-days. Biennial beets are homozygous for the recessive btc1 and bbx19 alleles, which encode non-functional proteins unable to repress the inhibitory function of FT1 (Pfeiffer et al., 2014 Theoretical and applied genetics 127: 2479-2489, incorporated herein by reference). Accordingly, biennial sugar beets require vernalization for BTC1- and BBX19-independent FT1 repression and flowering (Pin et al., 2010 Science 330: 1397, incorporated herein by reference).

As described in the Examples, the inventors sought to provide plants with improved cold and frost resistance and/or delayed or prevented bolting.

SUMMARY OF THE INVENTION

It has been surprisingly found that in response to cold temperatures, sink (e.g. taproot) to source (e.g. leaf) reversal may occur pre-bolting and pre-flowering. Deregulation of phloem flux modulates cold tolerance and/or bolting of plants. By deregulating the phloem flux in plants as taught herein, tolerance to cold may be increased and/or bolting may be inhibited or prevented. Phloem flux acts as a regulator of cold tolerance and/or bolting in plants.

In one aspect, the present invention provides a method of increasing the cold tolerance of a plant or part thereof and/or preventing or inhibiting bolting of a plant, comprising deregulating the phloem flux in said plant or part thereof.

Suitably, the phloem flux from sink tissues (e.g. taproots) to source tissues (e.g. shoots) may be reduced, inhibited or reversed when said plant or part thereof is grown in cold conditions.

Suitably the phloem flux may be reduced, inhibited or reversed post-vernalization.

Suitably, the method may comprise modifying said plant or part thereof to:
i) increase the activity or expression of a gene comprising:
  a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;
  b) a nucleotide sequence having the coding sequence as set forth in SEQ ID No: 2 or 8, or a coding sequence which has at least 80% or at least 85%, preferably at least 90%, at least 92%, or at least 94%, more preferably at least 96%, at least 98%, or at least 99% identity to SEQ ID No. 2 or 8;
  c) a nucleotide sequence that hybridizes with a sequence complementary to one of the nucleotide sequences according to a) or b) under stringent conditions;
  d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;
  e) a nucleotide sequence encoding a homologue, analogue or orthologue of a polypeptide comprising an amino acid sequence as set forth in SEQ ID No. 3 or 9; or
ii) increase the activity or expression of a polypeptide:
  a) encoded by a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7, or 8;
  b) encoded by a nucleotide sequence that hybridizes with a sequence complementary to one of the nucleotide sequences according to a) under stringent conditions;
  c) comprising an amino acid sequence as set forth in SEQ ID No. 3 or 9; or an amino acid sequence having at least 80% or at least 85%, preferably at least 90%, at least 92%, or at least 94%, more preferably at least 96%, at least 98%, or at least 99% identity to SEQ ID No. 3 or 9;
  d) which is a homologue, analogue or orthologue of a polypeptide comprising an amino acid sequence as set forth in SEQ ID No. 3 or 9.

Suitably, the method may comprise modifying said plant or part thereof to:
i) decrease the activity or expression of a gene comprising:
  a) a nucleotide sequence as set forth in SEQ ID No. 4, 5, 10, 11, 13, 14, 16 or 17, or a nucleotide sequence which has at least 80% identity to SEQ ID No. 4, 5, 10, 11, 13, 14, 16 or 17;
  b) a nucleotide sequence having the coding sequence as set forth in SEQ ID No. 5, 11, 14 or 17, or a coding sequence which has at least 80% identity to SEQ ID No. 5, 11, 14 or 17;
  c) a nucleotide sequence that hybridizes with a sequence complementary to one of the nucleotide sequences according to a) or b) under stringent conditions;
  d) a nucleotide sequence which encodes a polypeptide comprising an amino acid sequence as set forth in SEQ ID No. 6, 12, 15 or 18 or a sequence which has at least 80% or at least 85%, preferably at least 90%, at least 92%, or at least 94%, more preferably at least 96%, at least 98%, or at least 99% identity to SEQ ID No. 6, 12, 15 or 18;
  e) a nucleotide sequence encoding a homologue, analogue or orthologue of a polypeptide comprising an amino acid sequence as set forth in SEQ ID No. 6, 12, 15 or 18; or
ii) decrease the activity or expression of a polypeptide:
  a) encoded by a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17; 15
  b) encoded by a nucleotide sequence that hybridizes with a sequence complementary to one of the nucleotide sequences according to a) under stringent conditions;
  c) comprising an amino acid sequence as set forth in SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18;
  d) which is a homologue, analogue or orthologue of a polypeptide comprising an amino acid sequence as set forth in SEQ ID No. 6, 12, 15 or 18.

In another aspect, the present invention provides the use of a gene:
  a) comprising a nucleotide sequence as set forth in SEQ ID No. 1, 2, 4, 5, 7, 8, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 1, 2, 4, 5, 7, 8, 10 or 11, 13, 14, 16 or 17;
  b) comprising a nucleotide sequence having the coding sequence as set forth in SEQ ID No. 2, 5, 8, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 2, 5, 8, 11, 14 or 17;
  c) comprising a nucleotide sequence that hybridizes with a sequence complementary to one of the nucleotide sequences according to a) or b) under stringent conditions; 35 d) comprising a nucleotide sequence which encodes a polypeptide comprising an amino acid sequence as set forth in SEQ ID No. 3, 6, 9, 12, 15 or 18, or a sequence which has at least 80% or at least 85%, preferably at least 90%, at least 92%, or at least 94%, more preferably at least 96%, at least 98%, or at least 99% identity to SEQ ID No. 3, 6, 9, or 12, 15 or 18;

e) encoding an amino acid sequence as set forth in SEQ ID No. 3, 6, 9, 12, 15 or 18; or an amino acid sequence having at least 80% or at least 85%, preferably at least 90%, at least 92%, or at least 94%, more preferably at least 96%, at least 98%, or at least 99% identity to SEQ ID No. 3, 6, 9, 12, 15 or 18; or f) encoding a homologue, analogue or orthologue of a polypeptide comprising an amino acid sequence as set forth in SEQ ID No. 3, 6, 9, 12, 15 or 18;

for deregulating phloem flux in a plant or part thereof; and/or increasing cold tolerance of a plant or part thereof; and/or preventing or inhibiting bolting in a plant.

In another aspect, the present invention provides the use of a gene:

a) comprising a nucleotide sequence as set forth in SEQ ID No. 1, 2, 4, 5, 7, 8, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 1, 2, 4, 5, 7, 8, 10 or 11, 13, 14, 16 or 17;

b) comprising a nucleotide sequence having the coding sequence as set forth in SEQ ID No. 2, 5, 8, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 2, 5, 8, 11, 14 or 17;

c) comprising a nucleotide sequence that hybridizes with a sequence complementary to one of the nucleotide sequences according to a) or b) under stringent conditions;

d) comprising a nucleotide sequence which encodes a polypeptide comprising an amino acid sequence as set forth in SEQ ID No. 3, 6, 9, 12, 15 or 18, or a sequence which has at least 80% or at least 85%, preferably at least 90%, at least 92%, or at least 94%, more preferably at least 96%, at least 98%, or at least 99% identity to SEQ ID No. 3, 6, 9, or 12, 15 or 18;

e) encoding an amino acid sequence as set forth in SEQ ID No. 3, 6, 9, 12, 15 or 18; or an amino acid sequence having at least 80% or at least 85%, preferably at least 90%, at least 92%, or at least 94%, more preferably at least 96%, at least 98%, or at least 99% identity to SEQ ID No. 3, 6, 9, 12, 15 or 18; or f) encoding a homologue, analogue or orthologue of a polypeptide comprising an amino acid sequence as set forth in SEQ ID No. 3, 6, 9, 12, 15 or 18;

to select a plant having deregulated phloem flux in a plant or part thereof; and/or increased cold tolerance; and/or delayed or inhibited bolting.

In a further aspect, the present invention provides a method of selecting a plant with deregulated phloem flux and/or increased cold tolerance and/or delayed or inhibited bolting by selection of an allele, wherein the allele is associated with deregulated phloem flux, wherein said allele is:

a) a nucleotide sequence as set forth in SEQ ID No. 1, 2, 4, 5, 7, 8, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 1, 2, 4, 5, 7, 8, 10, 11, 13, 14, 16 or 17;

b) a nucleotide sequence having the coding sequence as set forth in SEQ ID No. 2, 5, 8, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 2, 5, 8, 11, 14 or 17;

c) a nucleotide sequence which hybridizes with a sequence complementary to one of the nucleotide sequences according to a) or b) under stringent conditions;

d) a nucleotide sequence encoding a polypeptide comprising an amino acid sequence as set forth in SEQ ID No. 3, 6, 9, 12, 15 or 18, or a sequence which has at least 80% or at least 85%, preferably at least 90%, at least 92%, or at least 94%, more preferably at least 96%, at least 98%, or at least 99% identity to SEQ ID No. 3, 6, 9, 12, 15 or 18;

e) a nucleotide sequence encoding a homologue, analogue or orthologue of a polypeptide comprising an amino acid sequence as set forth in SEQ ID No. 3, 6, 9, 12, 15 or 18;

f) an allele of any of a), b), c), d) or e); and said method comprises determining the presence or absence of said allele, preferably wherein said allele is identified by detecting the presence of a single nucleotide polymorphisms, length polymorphisms, indel polymorphisms.

In yet another aspect, the present invention provides a method of producing a cold tolerant plant and/or a plant with delayed or inhibited bolting, comprising crossing a donor plant comprising an allele associated with deregulated phloem flux wherein said allele comprises a polynucleotide sequence comprising:

a) a nucleotide sequence as set forth in SEQ ID No. 1, 2, 4, 5, 7, 8, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 1, 2, 4, 5, 7, 8, 10, 11, 13, 14, 16 or 17;

b) a nucleotide sequence having the coding sequence as set forth in SEQ ID No. 2, 5, 8, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 2, 5, 8, 11, 14 or 17;

c) a nucleotide sequence that hybridizes with a sequence complementary to one of the nucleotide sequences according to a) or b) under stringent conditions;

d) a nucleotide sequence encoding a polypeptide comprising an amino acid sequence as set forth in SEQ ID No. 3, 6, 9, 12, 15 or 18, or a sequence which has at least 80% or at least 85%, preferably at least 90%, at least 92%, or at least 94%, more preferably at least 96%, at least 98%, or at least 99% identity to SEQ ID No. 3, 6, 9, 12, 15 or 18;

e) a nucleotide sequence encoding a homologue, analogue or orthologue of a polypeptide comprising an amino acid sequence as set forth in SEQ ID No. 3, 6, 9, 12, 15 or 18; or f) an allele of any of a), b), c), d) or e);

with a recipient plant that possesses commercially desirable traits.

In a further aspect, the present invention provides a plant or part thereof obtainable (or obtained) from a method according to the present invention, or a use according to the present invention.

In another aspect, the present invention provides a plant propagation material (such as a seed) obtainable (or obtained) from a plant according to the present invention.

In another aspect, the present invention provides a modified plant cell wherein the plant cell has been modified to:
i) increase the activity or expression of a gene comprising:
   a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;
   b) a nucleotide sequence having the coding sequence as set forth in SEQ ID No. 2 or 8, or a nucleotide sequence which has at least 80% or at least 85%, preferably at least 90%, at least 92%, or at least 94%, more preferably at least 96%, at least 98%, or at least 99% identity to SEQ ID No. 2 or 8;
   c) a nucleotide sequence that hybridizes with a sequence complementary to one of the nucleotide sequences according to a) or b) under stringent conditions;
   d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;
   e) a nucleotide sequence encoding a homologue, analogue or orthologue of a polypeptide comprising an amino acid sequence as set forth in SEQ ID No. 3 or 9; or
ii) increase the activity or expression of a polypeptide:
   a) encoded by a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7, or 8;
   b) encoded by a nucleotide sequence that hybridizes with a sequence complementary to one of the nucleotide sequences according to a) under stringent conditions;
   c) comprising an amino acid sequence as set forth in SEQ ID No. 3 or 9; or an amino acid sequence having at least 80% or at least 85%, preferably at least 90%, at least 92%, or at least 94%, more preferably at least 96%, at least 98%, or at least 99% identity to SEQ ID No. 3 or 9;
   d) which is a homologue, analogue or orthologue of a polypeptide comprising an amino acid sequence as set forth in SEQ ID No. 3 or 9.
iii) decrease the activity or expression of a gene comprising:
   a) a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
   b) a nucleotide sequence having the coding sequence as set forth in SEQ ID No. 5, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 5, 11, 14 or 17;
   c) a nucleotide sequence that hybridizes with a sequence complementary to one of the nucleotide sequences according to a) or b) under stringent conditions;
   d) a nucleotide sequence which encodes a polypeptide comprising an amino acid sequence as set forth in SEQ ID No. 6, 12, 15 or 18 or a sequence which has at least 80% or at least 85%, preferably at least 90%, at least 92%, or at least 94%, more preferably at least 96%, at least 98%, or at least 99% identity to SEQ ID No. 6, 12, 15 or 18;
   e) a nucleotide sequence encoding a homologue, analogue or orthologue of a polypeptide comprising an amino acid sequence as set forth in SEQ ID No. 6, 12, 15 or 18; or
iv) decrease the activity or expression of a polypeptide:
   a) encoded by a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
   b) encoded by a nucleotide sequence that hybridizes with a sequence complementary to one of the nucleotide sequences according to a) under stringent conditions;
   c) comprising an amino acid sequence as set forth in SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18;
   d) which is a homologue, analogue or orthologue of a polypeptide comprising an amino acid sequence as set forth in SEQ ID No. 6, 12, 15 or 18.

In another aspect, the present invention provides a modified plant or part thereof, comprising a modified plant cell according to the present invention.

In a further aspect, the present invention provides plant propagation material obtainable (or obtained) from the modified plant according to the present invention.

Suitably, the plant or part thereof or plant cell for use in any aspect of the present invention may be from the Amaranthaceae family.

Suitably, the plant or part thereof or plant cell for use in any aspect of the present invention is from the Beta genus.

Suitably, the plant or part thereof or plant cell for use in any aspect of the present invention is *Beta vulgaris*, preferably *Beta vulgaris* subsp. *vulgaris*, more preferably *Beta vulgaris* subsp. *vulgaris* var. *altissima*, *Beta vulgaris* ssp. *vulgaris* var. *vulgaris*, Beta *vulgaris* ssp. *vulgaris* var. *conditiva*, *Beta vulgaris* ssp. *vulgaris* var. *crassa/alba*, and preferably wherein phloem flux from taproots to shoots is reduced, inhibited or reversed when said plant or part thereof is grown in cold conditions.

In another aspect, the present invention provides the use of a plant or part thereof or plant cell according to the present invention to breed a plant.

In a further aspect, the present invention provides the use of a plant or part thereof or plant cell according to the present invention for the production of a foodstuff, such as sugar, sugar beet syrup, molasses or a beverage.

In a further aspect, the present invention provides the use of a plant or part thereof or plant cell according to the present invention for the production of animal feed.

In yet another aspect, the present invention provides the use of a plant or part thereof or plant cell according to the present invention to grow a crop.

In an further aspect, the present invention provides a harvested root of a plant according to the present invention, or obtainable (or obtained) from a plant propagated from a propagation material according to the present invention, or obtainable (or obtained) from a method according to the present invention.

In one aspect, the present invention provides the use of a nucleotide sequence selected from:
- a) a nucleotide sequence as set forth in SEQ ID No. 1, 2, 4, 5, 7, 8, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 1, 2, 4, 5, 7, 8, 10, 11, 13, 14, 16 or 17;
- b) a nucleotide sequence having the coding sequence as set forth in SEQ ID No. 2, 5, 8, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 2, 5, 8, 11, 14 or 17;
- c) a nucleotide sequence that hybridizes with a sequence complementary to one of the nucleotide sequences according to a) or b) under stringent conditions;
- d) a nucleotide sequence which encodes a polypeptide comprising an amino acid sequence as set forth in SEQ ID No. 3, 6, 9, 12, 15 or 18, or a sequence which has at least 80% or at least 85%, preferably at least 90%, at least 92%, or at least 94%, more preferably at least 96%, at least 98%, or at least 99% identity to SEQ ID No. 3, 6, 9, 12, 15 or 18;
- e) a nucleotide sequence encoding a homologue, analogue or orthologue of a polypeptide comprising an amino acid sequence as set forth in SEQ ID No. 3, 6, 9, 12, 15 or 18;

to select a plant having deregulated phloem flux and/or increased cold tolerance and/or delayed or inhibited bolting.

In a further aspect, the present invention provides a method of increasing the sucrose concentration of a sucrose storage organ of a plant, which method comprises modifying said plant or part thereof to:
- i) decrease the activity or expression of a gene comprising:
  - a) a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
  - b) a nucleotide sequence having the coding sequence as set forth in SEQ ID No. 5, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 5, 11, 14 or 17;
  - c) a nucleotide sequence that hybridizes with a sequence complementary to one of the nucleotide sequences according to a) or b) under stringent conditions;
  - d) a nucleotide sequence which encodes a polypeptide comprising an amino acid sequence as set forth in SEQ ID No. 6, 12, 15 or 18 or a sequence which has at least 80% or at least 85%, preferably at least 90%, at least 92%, or at least 94%, more preferably at least 96%, at least 98%, or at least 99% identity to SEQ ID No. 6, 12, 15 or 18;
  - e) a nucleotide sequence encoding a homologue, analogue or orthologue of a polypeptide comprising an amino acid sequence as set forth in SEQ ID No. 6, 12, 15 or 18; or
- ii) decrease the activity or expression of a polypeptide:
  - a) encoded by a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
  - b) encoded by a nucleotide sequence that hybridizes with a sequence complementary to one of the nucleotide sequences according to a) under stringent conditions;
  - c) comprising an amino acid sequence as set forth in SEQ ID No. 6, 12, 15 or 18; or an amino acid sequence having at least 80% or at least 85%, preferably at least 90%, at least 92%, or at least 94%, more preferably at least 96%, at least 98%, or at least 99% identity to SEQ ID No. 6, 12, 15 or 18;
  - d) which is a homologue, analogue or orthologue of a polypeptide comprising an amino acid sequence as set forth in SEQ ID No. 6, 12, 15 or 18.

In another aspect, the present invention provides a method of selecting plants, parts thereof or plant cells having deregulated phloem flux and/or increased cold tolerance and/or delayed or inhibited bolting after vernalization by screening said plant or part thereof or plant cell for:
- i) decreased activity or expression of a gene comprising:
  - a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;
  - b) a nucleotide sequence having the coding sequence as set forth in SEQ ID No. 2 or 8, or a nucleotide sequence which has at least 80% or at least 85%, preferably at least 90%, at least 92%, or at least 94%, more preferably at least 96%, at least 98%, or at least 99% identity to SEQ ID No. 2 or 8;
  - c) a nucleotide sequence that hybridizes with a sequence complementary to one of the nucleotide sequences according to a) or b) under stringent conditions;
  - d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;

e) a nucleotide sequence encoding a homologue, analogue or orthologue of a polypeptide comprising an amino acid sequence as set forth in SEQ ID No. 3 or 9; and/or ii) decreased activity or expression of a polypeptide:
   a) encoded by a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7, or 8;
   b) encoded by a nucleotide sequence that hybridizes with a sequence complementary to one of the nucleotide sequences according to a) under stringent conditions;
   c) comprising an amino acid sequence as set forth in SEQ ID No. 3 or 9; or an amino acid sequence having at least 80% or at least 85%, preferably at least 90%, at least 92%, or at least 94%, more preferably at least 96%, at least 98%, or at least 99% identity to SEQ ID No. 3 or 9;
   d) which is a homologue, analogue or orthologue of a polypeptide comprising an amino acid sequence as set forth in SEQ ID No. 3 or 9; and/or iii) increased activity or expression of a gene comprising:
   a) a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
   b) a nucleotide sequence having the coding sequence as set forth in SEQ ID No. 5, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 5, 11, 14 or 17;
   c) a nucleotide sequence that hybridizes with a sequence complementary to one of the nucleotide sequences according to a) or b) under stringent conditions;
   d) a nucleotide sequence which encodes a polypeptide comprising an amino acid sequence as set forth in SEQ ID No. 6, 12, 15 or 18 or a sequence which has at least 80% or at least 85%, preferably at least 90%, at least 92%, or at least 94%, more preferably at least 96%, at least 98%, or at least 99% identity to SEQ ID No. 6, 12, 15 or 18;
   e) a nucleotide sequence encoding a homologue, analogue or orthologue of a polypeptide comprising an amino acid sequence as set forth in SEQ ID No. 6, 12, 15 or 18; and/or iv) increased activity or expression of a polypeptide:
   a) encoded by a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
   b) encoded by a nucleotide sequence that hybridizes with a sequence complementary to one of the nucleotide sequences according to a) under stringent conditions;
   c) comprising an amino acid sequence as set forth in SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18;
   d) which is a homologue, analogue or orthologue of a polypeptide comprising an amino acid sequence as set forth in SEQ ID No. 6, 12, 15 or 18.

In a further aspect, the present invention provides an isolated polynucleotide comprising a nucleotide sequence selected from the group consisting of:
   a) a nucleotide sequence as set forth in SEQ ID No. 4 or 5, or a nucleotide sequence which has at least 80% or at least 85%, preferably at least 90%, at least 92%, or at least 94%, more preferably at least 96%, at least 98%, or at least 99% identity to SEQ ID No. 4 or 5;
   b) a nucleotide sequence having the coding sequence as set forth in SEQ ID No. 5, or a nucleotide sequence which has at least 80% or at least 85%, preferably at least 90%, at least 92%, or at least 94%, more preferably at least 96%, at least 98%, or at least 99% identity to SEQ ID No. 5;
   c) a nucleotide sequence that hybridizes with a sequence complementary to one of the nucleotide sequences according to a) or b) under stringent conditions;
   d) a nucleotide sequence which encodes a polypeptide comprising an amino acid sequence as set forth in SEQ ID No. 6, or a sequence which has at least 80% or at least 85%, preferably at least 90%, at least 92%, or at least 94%, more preferably at least 96%, at least 98%, or at least 99% (such as at least 75%, at least 80%, at least 85%, at least 95%, at least 97%, at least 99%) identity to SEQ ID No. 6;
   e) a nucleotide sequence encoding a homologue, analogue or orthologue of a polypeptide comprising an amino acid sequence as set forth in SEQ ID No. 6.

In another aspect, the present invention provides an isolated polypeptide selected from the group consisting of:
   a) a polypeptide comprising an amino acid sequence as set forth in SEQ ID No. 6; or
   b) a polypeptide comprising an amino acid sequence having at least 80% or at least 85%, preferably at least 90%, at least 92%, or at least 94%, more preferably at least 96%, at least 98%, or at least 99% (such as at least 75%, at least 80%, at least 85%, at least 95%, at least 97%, at least 99%) identity to SEQ ID No. 6; or
   c) a homologue, analogue or orthologue of a polypeptide comprising an amino acid sequence as set forth in SEQ ID No. 6.

In yet another aspect, the present invention provides a genetic construct or vector comprising a polynucleotide according to the present invention; or a polynucleotide encoding a polypeptide according to the present invention.

BRIEF DESCRIPTION OF THE DRAWINGS

Embodiments of the invention will now be described, by way of example only, with reference to the accompanying drawings, in which:

FIG. 8 shows the phylogeny of *Beta vulgaris* SPS isoforms and protein abundance of BvSPS isoforms in taproots. (A) Phylogeny of BvSPS proteins. (B,C) SPSA1 and SPSA2 protein abundance based on MS counts (label free intensities, LFQ units) from GT1, GT2, GT3 (BvSPSA1=Bv2_030670_mgoq.t1; BvSPSA2=Bv8_193450_doak.t1).

FIG. 9 shows the phylogeny of *Beta vulgaris* SUS isoforms and protein abundance of BvSUS isoforms in taproots. (A) Phylogenetic tree of sucrose synthase amino acid sequences from sugar beet, *Arabidopsis* and potato. Sugar beet proteins had the following identifiers: BvSUS1: Bv8_190960_nnjy.t1, BvSUS2: Bv7_163460_jmqz.t1, BvSUS3: Bv7_173620_ffuo.t1, BvSUS4: Bv4_084720_myet.t1. *Arabidopsis* proteins had the following identifiers: AtSUS1: AT5G20830, AtSUS2: AT5G49190, AtSUS3: AT4g02280, AtSUS4: AT3G43190, AtSUS5: AT5G37180, AtSUS6: AT1G73370. Potato proteins had the following identifiers: StSUS1: NP_001275237.1, StSUS2: XP_015166930.1. (B,C) BvSUS1 and BvSUS2 protein abundance (label free intensity) in soluble protein fraction of 993 taproots from three different genotypes (white=GT1, dark grey=GT2, light grey=GT3) grown at 20° C. or grown at 20° C. and transferred for two weeks to 4° C.

FIG. 13 shows the phylogeny, sequence and predicted 2D-protein structure of BvSUT4. (A) Unrooted phylogenetic tree of sucrose transporters from the SUT/SUC family of *Beta vulgaris* and *Arabidopsis thaliana*. Bayesian phylogenetic analysis was performed with MrBayes version 3.2.6 (Ronquist et al., 2012). Mr Bayes was run by conducting two parallel Metropolis coupled Monte Carlo Markov chain analyses four twenty thousand generations. The standard deviation of split frequencies was below 0.01. The tree was visualized using FigTree v.1.4.3. Sugar beet protein sequences had the following identifiers (RefBeet 1.2): BvSUT1: Bv1_000710_gzum.t1, BvSUT3: Bv6_154300_yemu.t1, BvSUT4: Bv5_124860_zpft.t1. *Arabidopsis* proteins had the following identifiers: AtSUC1: AT1G71880, AtSUC2: AT1G22710, AtSUC3: AT2G02860, AtSUC4: AT1G09960, AtSUC5: AT1G71890, 1032 ATSUC9: AT5G06170. (B) Sequence and schematic depiction of the BvSUT4 protein. The protein has 535 aa and 12 transmembrane domains (underlined). The N-terminus includes the first 58 aa and the C-terminus the very last 14 aa, located in the cytoplasm of the cell. It has a central loop between transmembrane domain six and seven that includes 35 aa. FIG. 13B discloses SEQ ID NO: 6.

SEQUENCE LISTING

Figure 1:
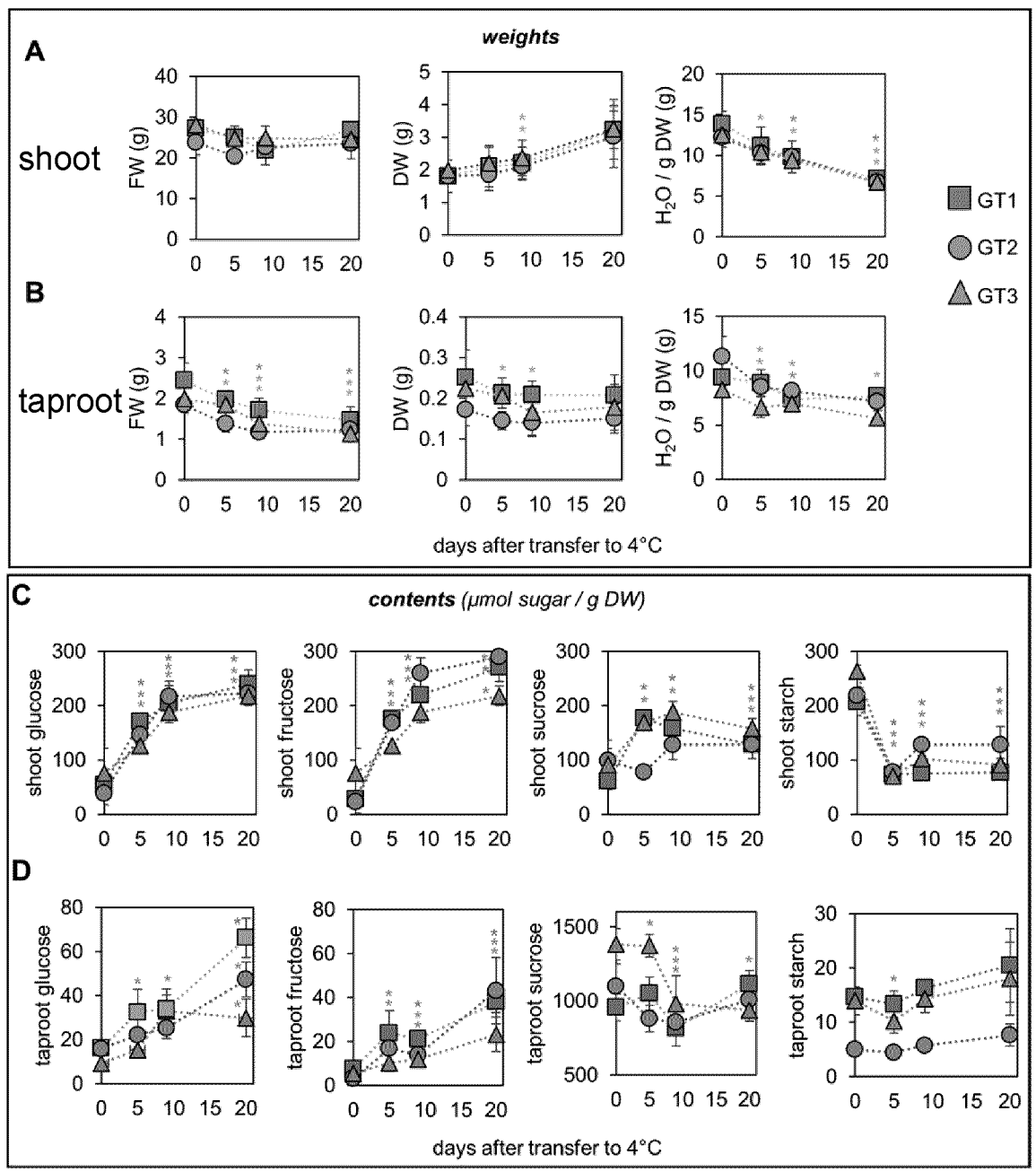
FIG. 1 shows biomass and sugar accumulation response to cold temperatures in shoots and taproots of 6-week old sugar beet plants from three different genotypes (GT1=square; GT2=circle; GT3=triangle). Plants were grown for six weeks at 20° C., then transferred to 12° C. for one week and then to 4° C. (start of recording of biomass and sugar accumulation) for 19 days. For each data point, whole organs (shoots or taproots) were harvested at midday. Data points show means from n=6 to 10 plants±SD. (A,B) Fresh weight (FW), dry weight (DW) and water content of shoots and roots. (C,D) Sugar and starch accumulation during the course of the chilling (4° C.) period in shoots and taproots, respectively. Significant changes to the control condition (first data point) were calculated using double sided Student's t-test (*=p<0.05).

A summary of sequence identifiers used throughout the subject specification and the corresponding sequence listing is provided wherein:

SEQ ID No. 1 corresponds to the genomic sequence of a tonoplast sugar transporter (TST) TST2.1 from *Beta vulgaris* (BvTST2.1).

SEQ ID No. 2 corresponds to the cDNA sequence of TST2.1 from *Beta vulgaris* (BvTST2.1).

SEQ ID No. 3 corresponds to the amino acid sequence of TST2.1 from *Beta vulgaris* (BvTST2.1).

SEQ ID No. 4 corresponds to the genomic sequence of SUT4 from *Beta vulgaris* (BvSUT4).

SEQ ID No. 5 corresponds to the cDNA sequence of SUT4 from *Beta vulgaris* (BvSUT4).

SEQ ID No. 6 corresponds to the amino acid sequence of SUT4 from *Beta vulgaris* (BvSUT4).

SEQ ID No. 7 corresponds to the genomic sequence of TMT1 from *Arabidopsis thaliana* (AtTMT1).

SEQ ID No. 8 corresponds to the cDNA sequence of TMT1 from *Arabidopsis thaliana* (AtTMT1).

SEQ ID No. 9 corresponds to the amino acid sequence of TMT1 from *Arabidopsis thaliana* (AtTMT1).

SEQ ID No. 10 corresponds to the nucleotide sequence of SUC4 from *Arabidopsis thaliana* (AtSUC4).

SEQ ID No. 11 corresponds to the cDNA sequence of SUC4 from *Arabidopsis thaliana* (AtSUC4).

SEQ ID No. 12 corresponds to the amino acid sequence SUC4 from *Arabidopsis thaliana* (AtSUC4).

SEQ ID No. 13 corresponds to a first genomic sequence of SWEET from *Beta vulgaris* (BvSWEET).

SEQ ID No. 14 corresponds to a first cDNA sequence of SWEET from *Beta vulgaris* (BvSWEET).

SEQ ID No. 15 corresponds to a first amino acid sequence of SWEET from *Beta vulgaris* (BvSWEET).

SEQ ID No. 16 corresponds to a second genomic sequence of SWEET from *Beta vulgaris* (BvSWEET).

SEQ ID No. 17 corresponds to a second cDNA sequence of SWEET from *Beta vulgaris* (BvSWEET).

SEQ ID No. 18 corresponds to a second amino acid sequence of SWEET from *Beta vulgaris* (BvSWEET).

SEQ ID No. 19 corresponds to the DNA sequence of the taproot specific Feb. 1, 1948 promoter.

DETAILED DESCRIPTION

For the first time the present inventors have shown that by deregulating the phloem flux in a plant or part thereof i.e. by decoupling phloem flux from regulation by one or more mechanism(s) which phloem flux is typically subjected, the cold tolerance of said plant or part thereof may be increased. The inventors have additionally shown that by deregulating the phloem flux in a plant or part thereof, i.e. by decoupling phloem flux from regulation by one or more mechanism(s) which phloem flux is typically subjected, bolting may be prevented or inhibited.

The inventors have surprisingly found that flux transition occurs pre-bolting i.e. before the formation of an inflorescence what would act as a new sink organ utilizing remobilised sugars as building blocks. More specifically this invention relates to methods of enhancing cold tolerance and/or preventing or inhibiting bolting of plants of industrial or commercial relevance by altering regulation of phloem flux.

The present invention provides a method of increasing the cold tolerance of a plant or part thereof and/or preventing or delaying bolting of a plant, comprising deregulating the phloem flux in said plant or part thereof.

The present inventors have surprisingly determined that phloem flux transition occurs after exposure to cold temperatures (such as post-vernalization) but pre-bolting i.e. before the formation of an inflorescence that would act as a new sink organ utilizing remobilised taproot sugars as building blocks.

It has been surprisingly found that by deregulating the phloem flux in a plant or part thereof, the cold tolerance of said plant or part thereof may be increased and/or bolting of said plant can be prevented or inhibited post-vernalization. Plants suitable for growing in cold conditions which maintain yield and sucrose content in harvestable roots are provided by the present invention. *Beta vulgaris* according to the present invention can be sown earlier, leading to a longer growing season leading to higher biomass and higher sugar yield. Suitably, the plants may be grown s "winter" beets. This allows the farmer an additional crop rotation.

Deregulated Phloem Flux

As used herein "deregulated phloem flux" means that phloem flux has been decoupled from regulation by one or more regulatory mechanism(s) to which phloem flux is usually subjected.

Suitably the phloem flux may be reduced, inhibited or reversed relative to a comparable plant under the same conditions.

The "phloem" is the living tissue in vascular plants which transports soluble organic compounds made during photosynthesis (such as sucrose) to parts of the plants where it is needed.

As used herein "phloem flux" has its normal meaning in the art and refers to the direction of flow through the phloem transport system.

The mass movement of phloem transport requires that the plasma membrane remains intact. At the source end of the phloem, sugars are moved into the phloem sieve elements. This increase in solute decreases the water potential of the cell and causes water to flow in from surrounding areas by osmosis. The increase in the volume of water in the cell causes an increase in pressure which forces the sugar/water/amino acid solution to move toward the sink tissue. At the sink tissue, the sugars are taken out of the phloem by active transport which increases the water potential and causes water to flow out of the phloem by osmosis. The sieve elements must keep a functioning plasma membrane in order to help control the flow of sugars into and out of the sieve element.

Two distinct methods can be employed by plants to move sugars into the phloem. Symplastic loading involves the movement of sugars through the plasmodesmata from one cell to another. Apoplastic loading involves the movement of sugars from the apoplast (the extracellular cell wall space) across the plasma membrane and into the cell. This movement of sugar against a concentration gradient is accomplished by sugar transporters in the plasma membrane Other molecules such as proteins and mRNA are also transported throughout the plant via phloem.

When grown in moderate temperatures, leaves photosynthesise and produce sucrose, the resulting sucrose is loaded into the phloem where it is transported to sink tissues (e.g. taproots). Cold treatment of plants (such as *Beta vulgaris*) typically leads to a reversal of flux in the phloem, i.e. tissues which had been sources during photosynthesis become sinks and vice versa. For example, post-cold treatment sucrose stored in the taproot is typically loaded to the phloem and transported to leaves/shoots. Post-vernalization, phloem flux is typically from tissues with relatively high concentrations of sucrose (e.g. storage organs) to tissues with relatively lower concentrations of sucrose (e.g. leaves/shoots) to provide energy and nutrients for bolting and/or flowering.

In one embodiment, phloem flux is deregulated pre-bolting and/or pre-flowering. Suitably, the phloem flux from storage organs to sink organs may be reduced, inhibited or reversed pre-bolting and/or pre flowering.

In one embodiment, phloem flux is deregulated post cold-temperature-induced vernalization. Suitably, the phloem flux from storage organs (e.g. taproots) to sink organs (e.g. leaves and/or shoots) may be reduced, inhibited or reversed post cold-temperature-induced vernalization. In one embodiment, phloem flux is deregulated post cold-temperature-induced vernalization and pre-bolting and/or pre-flowering. Suitably, the phloem flux from storage organs (e.g. taproots) to sink organs (e.g. leaves and/or shoots) may be reduced, inhibited or reversed post cold-temperature-induced vernalization and pre-bolting and/or pre-flowering.

In one embodiment, the phloem flux of a plant according to the invention is not reversed post cold-treatment and/or vernalization. In other words, a plant according to the present invention maintains the same source and sink tissue identities post-cold treatment and/or post vernalization as pre-cold treatment e.g. whilst the leaves of the plant were photosynthesising. Suitably, the phloem flux post cold-temperature-induced vernalization and pre-bolting and/or pre-flowering of a plant according to the present invention may be from leaves and/or shoots to taproots.

As used herein "vernalization" has its normal meaning in the art and refers to the transition from the vegetative to the generative phase induced by a prolonged period of low temperature, such as the prolonged cold experienced during winter or artificially generated conditions. Plants that have been vernalized may require additional signals or growth before they will bolt or flower. Bolting and/or flowering may occur weeks later.

In one aspect, vernalization may refer to exposure of a plant to cold temperature such as 12° C. or less, (preferably 10° C. or less, 8° C. or less, 6° C. or less, 4° C. or less, 2° C. or less) for a period of at least one (such as at least two, at least three, at least four, at least five or at least six) months.

"Cold temperatures" or "cold conditions" as used herein may refer to temperatures which are sufficient to initiate vernalization of a given plant. Suitably, cold temperatures may refer to temperatures such as 12° C. or less, (preferably 10° C. or less, 8° C. or less, 6° C. or less, 4° C. or less, 2° C. or less). Suitably, cold temperatures may refer to temperatures between about 2° C. to about 12° C., about 5° C. to about 10° C. or about 6° C. to about 8° C.

In one embodiment, deregulated phloem flux means that the phloem flux is reduced, inhibited or reversed relative to the phloem flux in a comparable plant under the same conditions. Suitably, the deregulated phloem flux is reduced, inhibited or reversed relative to the phloem flux in a comparable plant under cold conditions and/or post vernalization.

In one aspect, the phloem flux from sink tissues (e.g. taproots) to source tissues (e.g. leaves or shoots) is reduced, inhibited or reversed when said plant or part thereof is grown in cold conditions.

As used herein, "sink tissues" refer to any tissue of the plant which is storing or using sucrose. Typically, sinks are tissues in the plant with low osmotic concentration and low water pressure relative to other tissues in the plant.

Whilst a plant is photosynthesising, sink tissues can include storage organs such as roots (e.g. taproots). Under certain conditions, other tissues such as leaves or shoots can function as sink tissues. For example, after exposure to cold temperatures or post-vernalization, growing tissues such as leaves and/or shoots require energy and nutrients and can function as sink tissues.

As used herein "source tissues" refer to any tissue of the plant which is producing or releasing sucrose. Typically, sources are tissues in the plant with areas of high osmotic concentration and high water pressure relative to other tissues in the plant.

Source tissues include leaves during photosynthesis, when sucrose concentrations are relatively high compared to the rest of the plant. Under certain conditions, storage organs such as roots (e.g. taproots) can function as sources. For example, post-vernalization taproots can function as sources and sucrose can be moved into the phloem and redistributed to other tissues which require sucrose e.g. tissues which require energy for bolting and/or flowering. In one aspect, phloem flux from sink tissues (e.g. taproots) to source tissues (e.g. shoots) is reduced.

Suitably phloem flux from sink tissues (e.g. taproots) to source tissues (e.g. shoots) is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%.

Phloem flux may be measured using any method known in the art. For example, by using a radiolabelled translocation assay. Radiolabelled translocation assays are known in the art, for example those described in Liu et al., Journal of Experimental Botany, Volume 63, Issue 11, 28 Jun. 2012, Pages 4315-4320 which is incorporated herein by reference.

Cold Tolerance

The cultivation of commercial crops as winter crops can improve their economic performance by improving yield. Cold tolerance is a prerequisite for successfully cultivating winter crops. However, cool temperatures may also induce premature vernalization and subsequent early bolting and reduce yield such as reduce sugar production. The present inventors have found that by deregulating phloem flux, sucrose can be retained in sink tissues (e.g. taproots) and cold tolerance can be improved and/or bolting can be prevented or inhibited.

The degree of plant injury by cold or frost depends on a number of factors including for example, plant sensitivity to temperature (e.g. tropical plants typically have not developed avoidance of intracellular freezing), cooling and warming rates, relative humidity of air cold—hardening of plant tissue, and the minimum temperature reached by the plant tissue.

As used herein "cold tolerance" relates to the ability of a plant or part thereof or plant cell to withstand cold temperatures.

Suitably, plants according to the present invention exhibit less tissue damage after exposure to cold temperatures relative to comparable plants (or controls). In one embodiment, plants according to the present invention have at least 5%, 10%, 15%, 20%, 25%, 30%, 35%, 40%, 45%, 50%, 55%, 60%, 65%, 70%, 75%, 80%, 85%, 90%, 95% less tissue damage after exposure to cold temperatures relative to a comparable plant.

Tissue damage may be measured using any suitable method known in the art. For example, tissue damage following cold temperatures can be determined by measuring electrolyte release from tissue (see for example, M B Murray et al., New Phytol 1989, 113, 307-311; P A Klemens et al., Plant Physiol. 2013, 63(3): 1338-52. doi: 10.1104/U.S. Plant Pat. No. 113,224972; and P A Klemens et al., New Phytol. 2014, 202(1): 188-97. doi: 10.1111/nph.12642.) which are incorporated herein by reference).

Injured cells are unable to maintain the chemical composition of their contents and release electrolytes through damaged membranes. The increased rate of loss of electrolytes can be determined by placing tissue in water and measuring the conductivity of the resultant solution. In one embodiment, plants according to the present invention have at least 5%, 10%, 15%, 20%, 25%, 30%, 35%, 40%, 45%, 50%, less electrolyte leakage relative to a comparable plant wherein the electrolyte release assay is performed under the same conditions.

Electrolyte Release Assay/Electrical Conductivity Measurements

Electrical conductivity measurement of frozen leaf tissue (as e.g. applied in Klemens et al., 2013, Klemens et al., 2014) was assessed with four-week-old plants, which were acclimated to 4° C. for 4 days. One fully expanded leaf harvested at midday was placed in a glass tube containing 2 ml sterile deionized water. The tubes were transferred to a cryostat at 0° C. for 1 h followed by cooling of 1° C. per hour up to a temperature minimum of −6° C. Freezing of the water inside the glass tubes was initiated at −1° C. with an iced inoculation loop. Subsequently, the tubes were thawed overnight and afterwards shaken overnight on a horizontal shaker at 4° C. After thawing, the tubes were filled with 3 ml of sterile deionized water and gently shaken for one more hour at room temperature. The electrical conductivity of each sample was quantified at room temperature using a LF521 conductivity meter (WTW, Weilheim, Germany) and compared to the total electrical conductivity after boiling for 2 hours and shaking overnight. Suitably, plants according to the present invention may survive cold and/or frost better than respective comparable plants (or controls). In one embodiment, a crop plants according to the present invention have at least a 5%, 10%, 15%, 20%, 25%, 30%, 35%, 40%, 45%, 50%, 55%, 60%, 65%, 70%, 75%, 80%, 85%, 90%, 95% higher survival rate relative to a crop of comparable plants.

Suitably, plants according to the present invention may withstand colder temperatures without suffering tissue damage or dying relative to a comparable plant Suitably, plants according to the present invention may withstand colder temperatures for a longer period of time without suffering tissue damage or dying relative to a comparable plant The present invention relates to methods for producing plants or parts thereof having increased cold tolerance. The present invention relates to plants that exhibit increased cold tolerance, relative to the level of cold tolerance in comparable plants.

In one embodiment, plant seedlings according to the present invention having 6 or fewer (such as two, or four) true leaves have increased cold tolerance relative to comparable seedlings. In one embodiment, plant seedlings according to the present invention having 6 or more (such as 8 or more) true leaves have increased cold tolerance relative to comparable seedlings. As used herein "frost tolerance" relates to the ability of a plant or part thereof or plant cell to withstand frost. Suitably, frost tolerance may relate to the ability of a plant or part thereof or plant cell to withstand extracellular ice.

In some embodiments, frost tolerance includes frost avoidance, which relates to the ability of a plant or part thereof or plant cell to avoid extracellular or intracellular ice formation.

The critical minimum temperature a plant can withstand is determined by a combination of environmental and genetic factors. Direct frost damage occurs when ice crystals form inside the protoplasm of cells (intracellular freezing), whereas indirect damage can occur when ice forms inside the plants but outside of the cells (i.e. extracellular freezing). It is not cold temperature but ice formation that actually injures the plant. It is believed that intracellular ice formation causes a mechanical disruption of the protoplasmic structure. The extent of damage due to intracellular freezing depends mainly on how fast the temperature drops and to what level it supercools before freezing.

Bolting

In one embodiment, the present invention provides a method of preventing or inhibiting bolting of a plant, comprising deregulating the phloem flux in said plant (e.g. a *Beta vulgaris* plant) or part thereof.

Suitably plants (e.g. a *Beta vulgaris* plants) according to the present invention may be bolting resistant.

As used herein, "bolting" has its usual meaning in the art and refers to the process where a plant has stopped productive growth and has switched to reproductive growth. Bolting typically refers to the first visible signs of production of a flowering stem (or stems) which are part of the plant's attempt to produce seed in order to reproduce. To produce a bolted stem, a plant typically redirects resources from producing leaves, roots or other edible parts. Bolting is typically used as a predictor of flower formation.

Plants which have bolted typically produce a poor yield and impaired flavour compared to plants which have not bolted.

In some embodiments, the present invention provides methods of preventing or inhibiting bolting and/or flowering of a plant.

An "inhibition of bolting and/or flowering" of a plant (e.g. a *Beta vulgaris* plant) refers to a reduction in the proportion of bolting and/or flower forming plants relative to a comparable plant i.e. a plant of the same subspecies or variety in a comparable stage of development, particularly in the second year after passing through a corresponding cold period, i.e. after vernalization.

Suitably, plants according to the invention (e.g. a *Beta vulgaris* plant) exhibit less than 80%, preferably less than 70%, 60%, 50%, 40%, 30%, 20% or 10%, more preferably less than 5%, 4%, 3%, 2%, 1%, 0.5%, 0.4%, 0.3%, 0.2% or 0.1% of the percentage of bolting relative to comparable plants not according to the invention.

In one embodiment, bolting and/or flowering may be substantially prevented or completely prevented.

The term "substantially prevented" or "completely prevented" bolting and flowering is understood to mean inhibition of at least 80%, at least 90%, at least 95%, at least 98%, at least 99%, preferably at least 99.5%, more preferably at least 99.8%, or at least 99.9%, that is, a reduction of the proportion of bolters to not more than 20%, not more than 15% or not more than 10%, not more than 5%, not more than 2%, not more than 1% or not more than 0.5%, especially in the second year after vernalization, relative to a comparable plant or plant population i.e. a plant or plant population of the same subspecies or variety in a comparable stage of development, particularly in the second year after passing through a corresponding cold period, i.e. after vernalization.

Methods

The present inventors have surprisingly determined that phloem flux transition occurs after exposure to cold conditions but pre-bolting i.e. before the formation of an inflorescence that would act as a new sink organ utilizing remobilized taproot sugars.

The present invention provides methods for increasing cold tolerance and/or inhibiting or preventing bolting by deregulating of the change in phloem flux which normally occurs as a result of cold treatment i.e. post vernalization and pre-bolting.

By targeting the activity and/or expression of genes involved in the regulation of phloem flux, the present invention provides plants with increased tolerance to cold and with delayed or inhibited bolting relative to comparable plants.

In one aspect, phloem flux may be deregulated by modifying the activity or expression of genes which control the transport of sucrose.

In one aspect, phloem flux may be deregulated by modulating the activity or expression of sucrose transporters. Without wishing to be bound by theory, modifying the activity or expression of a sucrose transporter may increase or decrease sucrose transport out of a given tissue thereby modifying phloem flux.

The "expression" of a gene typically refers to the level of transcription. The expression of a gene may be measured using any method known in the art, for example by northern blot, RNA-Seq, in situ hybridization, DNA microarrays and RT-PCR Alternatively, the expression of a gene may be measured indirectly by measuring the level of the gene product for example the protein encoded by said gene by western blot.

The "activity" of transporters disclosed herein relates to their ability to transport a substrate.

The activity of a transporter can be modified by changing its cellular localisation, substrate specificity or interaction with other proteins such as binding affinity for substrate.

The activity of a transporter may be determined by using a fluorescent reporter e.g. a fluorescent tagged substrate molecule and measuring transport using microscopy.

In one aspect, the activity or expression of a gene or protein is measured relative to a comparable product.

The term "a comparable plant" or "comparable product" as defined herein would be a plant or a product derived from a plant (e.g. a *Beta vulgaris* plant) which had not been modified according to the present invention, but in which all other relevant features were the same (e.g. plant species, growing conditions, method of processing the plant). The comparable plant or comparable product according to the present invention may mean a plant (e.g. a *Beta vulgaris* plant) or a part thereof, such as a root (e.g. a taproot), a harvested root (e.g. a harvested taproot), or plant propagation material (e.g. *Beta vulgaris* propagation material), or a product comprising said plant or part thereof, obtainable or obtained from a plant which has not been modified in accordance with the present invention, e.g. to deregulate phloem flux. In one embodiment a comparable plant is one which does not exhibit deregulated phloem flux during or after exposure to cold conditions. In one embodiment a comparable plant does not exhibit delayed bolting after exposure to cold conditions.

The term "modifying" or "modified" as used herein means a plant (e.g. a *Beta vulgaris* plant) that has been altered or changed. The present invention comprises the modification of plants using techniques for genetic modification of plants or non-genetic modification of plants. Such methods are well known in the art and examples of genetic modification techniques include transformation, transgenics, cisgenics, and gene editing methods. Examples of non-genetic modification techniques include fast-neutron mutagenesis, chemical mutagenesis e.g. ethyl methanesulfonate (EMS) mutagenesis and modern population analysis approaches.

The term "unmodified plant" as defined herein would be a plant (e.g. a *Beta vulgaris* plant) which had not been modified according to the present invention, to deregulate phloem flux and in which all other relevant features were the same (e.g. plant species, growing conditions, method of processing, etc.). In one embodiment an unmodified plant is one which does not exhibit deregulated phloem flux during or after exposure to cold conditions. In one embodiment an unmodified plant does not exhibit delayed bolting after exposure to cold conditions.

Increasing Gene Expression

In one aspect, the present invention provides a method of increasing the cold tolerance of a plant or part thereof and/or preventing or delaying bolting of a plant, comprising increasing the activity or expression of a sucrose/proton antiporter residing in the tonoplast of taproot storage vacuoles. The vacuolar membrane is involved in solute uptake into and solute release from the vacuole. Protons and sugars are shuttled across this membrane in addition to metabolites and inorganic ions. It is believed that the proton gradient across this membrane drives the accumulation and/or release of sugars. The sucrose/proton antiporter imports sucrose into the vacuole. Suitably, the sucrose/proton antiporter may be a proton-coupled antiporter capable of loading sucrose into the vacuole. Suitably, the sucrose/proton antiporter may be from *Beta vulgaris* or a homologue of a *Beta vulgaris* sequence. Suitably, the sucrose/proton antiporter may be from *Arabidopsis thaliana* or a homologue of an *Arabidopsis thaliana* sequence. In one aspect, the sucrose/proton antiporter gene comprises:

a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;

b) a nucleotide sequence having the coding sequence as set forth in SEQ ID No. 2 or 8, or a nucleotide sequence which has at least 80% or at least 85%, preferably at least 90%, at least 92%, or at least 94%, more preferably at least 96%, at least 98%, or at least 99% identity to SEQ ID No. 2 or 8;

c) a nucleotide sequence that hybridizes with a sequence complementary to one of the nucleotide sequences according to a) or b) under stringent conditions;

d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;

e) a nucleotide sequence encoding a homologue, analogue or orthologue of a polypeptide comprising an amino acid sequence as set forth in SEQ ID No. 3 or 9.

SEQ ID No. 1 corresponds to the genomic sequence of a tonoplast sugar transporter (TST) TST2.1 from *Beta vulgaris* (BvTST2.1).

SEQ ID No. 2 corresponds to the cDNA sequence of TST2.1 from *Beta vulgaris* (BvTST2.1).

SEQ ID No. 3 corresponds to the amino acid sequence of TST2.1 from *Beta vulgaris* (BvTST2.1).

SEQ ID No. 7 corresponds to the genomic sequence of TMT1 from *Arabidopsis thaliana* (AtTMT1).

SEQ ID No. 8 corresponds to the cDNA sequence of TMT1 from *Arabidopsis thaliana* (AtTMT1).

SEQ ID No. 9 corresponds to the amino acid sequence of TMT1 from *Arabidopsis thaliana* (AtTMT1).

Without wishing to be bound by theory, increasing the expression and/or activity of a sucrose/proton antiporter, such as TST2.1 or TMT1 (for example in the taproot), may increase loading of sucrose to the vacuole. Suitably, increasing the expression and/or activity of a sucrose/proton antiporter, such as TST2.1 or TMT1 (for example in the taproot), may increase loading of sucrose to the vacuole, deregulate phloem flux in a plant or part thereof and increase the cold tolerance of a plant or part thereof and/or prevent or inhibit bolting of a plant.

In one aspect, the sucrose/proton antiporter protein is:

a) encoded by a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7, or 8;
b) encoded by a nucleotide sequence that hybridizes with a sequence complementary to one of the nucleotide sequences according to a) under stringent conditions;
c) comprises an amino acid sequence as set forth in SEQ ID No. 3 or 9; or an amino acid sequence having at least 80% or at least 85%, preferably at least 90%, at least 92%, or at least 94%, more preferably at least 96%, at least 98%, or at least 99% identity to SEQ ID No. 3 or 9;
d) a homologue, analogue or orthologue of a polypeptide comprising an amino acid sequence as set forth in SEQ ID No. 3 or 9.

The present invention provides a method of increasing the cold tolerance of a plant or part thereof and/or preventing or inhibiting bolting of a plant, comprising deregulating the phloem flux in said plant or part thereof by modifying said plant or part thereof to:
 i) increase the activity or expression of a gene comprising:
  a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;
  b) a nucleotide sequence having the coding sequence as set forth in SEQ ID No. 2 or 8, or a nucleotide sequence which has at least 80% or at least 85%, preferably at least 90%, at least 92%, or at least 94%, more preferably at least 96%, at least 98%, or at least 99% identity to SEQ ID No. 2 or 8;
  c) a nucleotide sequence that hybridizes with a sequence complementary to one of the nucleotide sequences according to a) or b) under stringent conditions;
  d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;
  e) a nucleotide sequence encoding a homologue, analogue or orthologue of a polypeptide comprising an amino acid sequence as set forth in SEQ ID No. 3 or 9; or
 ii) increase the activity or expression of a polypeptide:
  a) encoded by a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7, or 8;
  b) encoded by a nucleotide sequence that hybridizes with a sequence complementary to one of the nucleotide sequences according to a) under stringent conditions;
  c) comprising an amino acid sequence as set forth in SEQ ID No. 3 or 9; or an amino acid sequence having at least 80% or at least 85%, preferably at least 90%, at least 92%, or at least 94%, more preferably at least 96%, at least 98%, or at least 99% identity to SEQ ID No. 3 or 9;
  d) which is a homologue, analogue or orthologue of a polypeptide comprising an amino acid sequence as set forth in SEQ ID No. 3 or 9.

In one embodiment a sucrose/proton antiporter comprises an amino acid sequence shown as SEQ ID No. 3 or a sequence which has at least 80% identity thereto, or a homologue thereof. Suitably, a sucrose/proton antiporter comprises an amino acid sequence shown as SEQ ID No. 3 or a sequence which has at least 85% identity thereto which is capable of functioning as a tonoplast sucrose/proton antiporter, or a homologue of SEQ ID NO. 3 thereof. Suitably, a homologue of SEQ ID No. 3 may be SEQ ID No. 9 or a sequence which has at least 80% identity thereto which is capable of functioning as a tonoplast sucrose/proton antiporter.

A protein which is capable of functioning as a tonoplast sucrose/proton antiporter is preferably expressed in the tonoplast.

In one embodiment a sucrose/proton antiporter comprises an amino acid sequence shown as SEQ ID No. 3 or a sequence which has at least 85%, preferably at least 90%, at least 92%, or at least 94%, more preferably at least 96%, at least 98%, or at least 99% identity thereto.

In one embodiment a sucrose/proton antiporter comprises an amino acid sequence shown as SEQ ID No. 9, or a sequence which has at least 85%, preferably at least 90%, at least 92%, or at least 94%, more preferably at least 96%, at least 98%, or at least 99% identity thereto. In one embodiment the sucrose/proton antiporter is encoded by a polynucleotide sequence comprising the sequence shown as SEQ ID No. 1, SEQ ID No. 2, SEQ ID No. 7 or SEQ ID No. 8, or a sequence which has at least 80% or at least 85%, preferably at least 90%, at least 92%, or at least 94%, more preferably at least 96%, at least 98%, or at least 99% sequence identity thereto.

Suitably, the sucrose/proton antiporter for use according to the present invention may be encoded by a polynucleotide sequence comprising the sequence shown as SEQ ID No. 1, or a sequence which has at least 85%, preferably at least 90%, at least 92%, or at least 94%, more preferably at least 96%, at least 98%, or at least 99% sequence identity thereto.

Suitably, the sucrose/proton antiporter for use according to the present invention may be encoded by a polynucleotide sequence comprising the sequence shown as SEQ ID No. 2, or a sequence which has at least 85%, preferably at least 90%, at least 92%, or at least 94%, more preferably at least 96%, at least 98%, or at least 99% sequence identity thereto.

Suitably, sucrose/proton antiporter for use according to the present invention may be encoded by a polynucleotide sequence comprising the sequence shown as SEQ ID No. 7, or a sequence which has at least 85%, preferably at least 90%, at least 92%, or at least 94%, more preferably at least 96%, at least 98%, or at least 99% sequence identity thereto.

Suitably, the sucrose/proton antiporter for use according to the present invention may be encoded by a polynucleotide sequence comprising the sequence shown as SEQ ID No. 8, or a sequence which has at least 85%, preferably at least 90%, at least 92%, or at least 94%, more preferably at least 96%, at least 98%, or at least 99% sequence identity thereto.

The term "increasing" (e.g. increasing the activity or expression of a gene) as used herein means that the activity or expression of the gene is higher compared with the gene activity or expression of the unmodified gene in a comparable product.

In some embodiments a modification which increases the activity or expression of a tonoplast sucrose/proton antiporter is selected from the group consisting of:

increasing, promoting or augmenting transcription, translation or expression of the tonoplast sucrose/proton antiporter;

increasing synthesis of the polypeptide encoded by the tonoplast sucrose/proton antiporter;

or its release from intracellular stores; or decreasing the rate of degradation of the polypeptide encoded by the tonoplast sucrose/proton antiporter gene.

Suitably the method may comprise transforming a cell of a plant (e.g. a *Beta vulgaris* plant) with a genetic construct which:

i) increases the activity or expression of a gene comprising:
   a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;
   b) a nucleotide sequence having the coding sequence as set forth in SEQ ID No. 2 or 8, or a nucleotide sequence which has at least 80% or at least 85%, preferably at least 90%, at least 92%, or at least 94%, more preferably at least 96%, at least 98%, or at least 99% identity to SEQ ID No. 2 or 8;
   c) a nucleotide sequence that hybridizes with a sequence complementary to one of the nucleotide sequences according to a) or b) under stringent conditions;
   d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;
   e) a nucleotide sequence encoding a homologue, analogue or orthologue of a polypeptide comprising an amino acid sequence as set forth in SEQ ID No. 3 or 9; or ii) increases the activity or expression of a polypeptide:
   a) encoded by a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7, or 8;
   b) encoded by a nucleotide sequence that hybridizes with a sequence complementary to one of the nucleotide sequences according to a) under stringent conditions;
   c) comprising an amino acid sequence as set forth in SEQ ID No. 3 or 9; or an amino acid sequence having at least 80% or at least 85%, preferably at least 90%, at least 92%, or at least 94%, more preferably at least 96%, at least 98%, or at least 99% identity to SEQ ID No. 3 or 9;
   d) which is a homologue, analogue or orthologue of a polypeptide comprising an amino acid sequence as set forth in SEQ ID No. 3 or 9.

Suitably the construct may comprise:
a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;
b) a nucleotide sequence having the coding sequence as set forth in SEQ ID No. 2 or 8, or a nucleotide sequence which has at least 80% or at least 85%, preferably at least 90%, at least 92%, or at least 94%, more preferably at least 96%, at least 98%, or at least 99% identity to SEQ ID No. 2 or 8;
c) a nucleotide sequence that hybridizes with a sequence complementary to one of the nucleotide sequences according to a) or b) under stringent conditions;
d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;
e) a nucleotide sequence encoding a homologue, analogue or orthologue of a polypeptide comprising an amino acid sequence as set forth in SEQ ID No. 3 or 9 or comprises a nucleotide sequence which encodes a protein which is capable of promoting or augmenting at least one endogenous tonoplast sucrose/proton antiporter. It will be appreciated that each of these options would result in an increased activity and expression of the polypeptide encoded by the tonoplast sucrose/proton antiporter gene. The method may comprise regenerating the plant from the transformed cell.

In one embodiment the activity of at least one gene encoding a tonoplast sucrose/proton antiporter may be increased by introducing (or providing) a mutation to at least one gene encoding a tonoplast sucrose/proton antiporter. In another embodiment, the activity or at last one gene encoding a tonoplast sucrose/proton antiporter may be increased by introducing (or providing) a mutation to a promoter or enhancer element which co-ordinates expression of the gene. Suitably the mutation may be outside of the coding sequence of the gene.

In one embodiment, the tonoplast sucrose/proton antiporter for use according to the present invention exhibits increased activity compared to an unmodified protein. The protein for use according to the present invention may exhibit at least about about 5%, at least about 10%, at least about 20%, at least about 30%, at least about 40%, at least about 50%, at least about 60%, at least about 70%, at least about 80%, at least about 90%, at least about 100%, at least about 200%, at least about 300%, at least about 500%, at least about 1,000%, at least about 2,000%, at least about 3,000%, at least about 5,000%, at least about 10,000%, at least about 20,000%, at least about 30,000%, at least about 50,000% or at least about 100,000% more activity compared to an unmodified tonoplast sucrose/proton antiporter.

Suitably, the promoter region of a gene may be modified to increase expression of a gene. Promoters and/or enhancers which co-ordinate expression of the gene may be modified to increase expression of the gene. In particular, the TATA box or other activating motifs within the promoter may be modified to increase expression of the gene. In one embodiment, the tonoplast sucrose/proton antiporter comprises a mutation which renders the tonoplast sucrose/proton antiporter constitutively active. In one embodiment, the activity of a tonoplast sucrose/proton antiporter may be increased by overexpressing the tonoplast sucrose/proton antiporter. Suitably, the activity of a tonoplast sucrose/proton antiporter may be increased by providing multiple copies of the tonoplast sucrose/proton antiporter gene.

Suitably, the activity of at least one gene encoding a tonoplast sucrose/proton antiporter may be increased by introducing a mutation to at least one gene encoding tonoplast sucrose/proton antiporter which comprises an amino acid sequence as set out in SEQ ID No. 3, or 9, or a functional variant or functional fragment or orthologue thereof, or a sequence which has at least 80% identity to SEQ ID No. 3, or 9; or wherein the at least one gene encoding a tonoplast sucrose/proton antiporter comprises a nucleotide sequence as set out in SEQ ID No. 1, 2, 7 or 8, or a functional variant or functional fragment or orthologue of SEQ ID No. 1, 2, 7 or 8, or a nucleic acid sequence which has at least 85%, preferably at least 90%, at least 92%, or at least 94%, more preferably at least 96%, at least 98%, or at least 99% identity to SEQ ID No. 1, 2, 7 or 8.

In one embodiment, the method of increasing gene activity and/or expression comprises the use of a promoter activating nucleic acid sequence configured for target site-specific insertion into a recipient promoter controlling the expression of a nucleic acid molecule of interest in a cell or an organism, wherein the promoter activating nucleic acid sequence causes an increased expression of the nucleic acid molecule of interest upon site specific insertion, preferably wherein the nucleic acid molecule of interest is heterologous or native to the recipient promoter and/or is an endogenous or exogenous nucleic acid molecule to the cell or organism. Such methods are described in EP 3 546 582, which is incorporated herein by reference.

Decreasing Gene Expression

In one aspect, the present invention provides a method of increasing the cold tolerance of a plant or part thereof and/or preventing or delaying bolting of a plant, comprising decreasing the activity or expression of a protein which mediates sucrose efflux, such as a sucrose/proton symporter or a protein exports sucrose e.g. SWEET proteins. Suitably, the protein may be from *Beta vulgaris* or a homologue of a *Beta vulgaris* sequence. Suitably, the protein may be from *Arabidopsis thaliana* or a homologue of an *Arabidopsis thaliana* sequence.

The vacuolar membrane is involved in solute uptake into and solute release from the vacuole. Protons and sugars are shuttled across this membrane in addition to metabolites and inorganic ions. It is believed that the proton gradient across this membrane drives the accumulation and/or release of sugars. Sucrose/proton symporters such as BvSUT4 (SEQ ID No. 6) and AtSUC4 (SEQ ID No. 12) catalyse proton-coupled sucrose export from the vacuole. Sucrose uniporters such as SWEET proteins (SEQ ID No. 15 and SEQ ID No. 18) export sucrose. SEQ ID No. 10 corresponds to the nucleotide sequence of SUC4 from *Arabidopsis thaliana* (AtSUC4).

SEQ ID No. 11 corresponds to the cDNA sequence of SUC4 from *Arabidopsis thaliana* (AtSUC4).

SEQ ID No. 12 corresponds to the amino acid sequence e SUC4 from *Arabidopsis thaliana* (AtSUC4).

SEQ ID No. 4 corresponds to the genomic sequence of SUT4 from *Beta vulgaris* (BvSUT4).

SEQ ID No. 5 corresponds to the cDNA sequence of SUT4 from *Beta vulgaris* (BvSUT4).

SEQ ID No. 6 corresponds to the amino acid sequence of SUT4 from *Beta vulgaris* (BvSUT4).

Without wishing to be bound by theory, decreasing the expression and/or activity of a sucrose/proton symporter, such as BvSUT4 or AtSUC4 (for example in the taproot), may decrease sucrose export from the vacuole. Suitably, decreasing the expression and/or activity of a sucrose/proton symporter, such as BvSUT4 or AtSUC4 (for example in the taproot), may decrease sucrose export from the vacuole, deregulate phloem flux in a plant or part thereof and increase the cold tolerance of a plant or part thereof and/or prevent or inhibit bolting of a plant.

SEQ ID No. 13 corresponds to a first genomic sequence of SWEET from *Beta vulgaris* (BvSWEET).

SEQ ID No. 14 corresponds to a first cDNA sequence of SWEET from *Beta vulgaris* (BvSWEET).

SEQ ID No. 15 corresponds to a first amino acid sequence of SWEET from *Beta vulgaris* (BvSWEET).

SEQ ID No. 16 corresponds to a second genomic sequence of SWEET from *Beta vulgaris* (BvSWEET).

SEQ ID No. 17 corresponds to a second cDNA sequence of SWEET from *Beta vulgaris* (BvSWEET).

SEQ ID No. 18 corresponds to a second amino acid sequence of SWEET from *Beta vulgaris* (BvSWEET).

Without wishing to be bound by theory, decreasing the expression and/or activity of a sucrose uniporter e.g. SWEET protein, such as SEQ ID No. 15 or SEQ ID No. 18, may inhibit unloading of sucrose from the phloem, leading to an accumulation of sucrose in the phloem. Suitably, decreasing the expression and/or activity of a sucrose uniporter e.g. SWEET protein, such as SEQ ID No. 15 or SEQ ID No. 18, may inhibit unloading of sucrose from the phloem, leading to an accumulation of sucrose in the phloem, deregulate phloem flux in a plant or part thereof and increase the cold tolerance of a plant or part thereof and/or prevent or inhibit bolting of a plant.

In one aspect, the gene whose activity or expression is decreased comprises:
a) a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
b) a nucleotide sequence having the coding sequence as set forth in SEQ ID No. 5, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 5, 11, 14, or 17;
c) a nucleotide sequence that hybridizes with a sequence complementary to one of the nucleotide sequences according to a) or b) under stringent conditions;
d) a nucleotide sequence which encodes a polypeptide comprising an amino acid sequence as set forth in SEQ ID No. 6, 12, 15 or 18 or a sequence which has at least 80% or at least 85%, preferably at least 90%, at least 92%, or at least 94%, more preferably at least 96%, at least 98%, or at least 99% identity to SEQ ID No. 3 or 9;
e) a nucleotide sequence encoding a homologue, analogue or orthologue of a polypeptide comprising an amino acid sequence as set forth in SEQ ID No. 6, 12, 15 or 18.

In one aspect, the protein whose activity or expression is decreased is:
a) encoded by a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;

b) encoded by a nucleotide sequence that hybridizes with a sequence complementary to one of the nucleotide sequences according to a) under stringent conditions;

c) comprising an amino acid sequence as set forth in SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18;

d) which is a homologue, analogue or orthologue of a polypeptide comprising an amino acid sequence as set forth in SEQ ID No. 6, 12, 15 or 18.

The present invention provides a method of increasing the cold tolerance of a plant or part thereof and/or preventing or inhibiting bolting of a plant, comprising deregulating the phloem flux in said plant or part thereof by modifying said plant or part thereof to:

i) decrease the activity or expression of a gene comprising:
   a) a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
   b) a nucleotide sequence having the coding sequence as set forth in SEQ ID No. 5, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 5, 11, 14 or 17;
   c) a nucleotide sequence that hybridizes with a sequence complementary to one of the nucleotide sequences according to a) or b) under stringent conditions;
   d) a nucleotide sequence which encodes a polypeptide comprising an amino acid sequence as set forth in SEQ ID No. 6, 12, 15 or 18 or a sequence which has at least 80% or at least 85%, preferably at least 90%, at least 92%, or at least 94%, more preferably at least 96%, at least 98%, or at least 99% identity to SEQ ID No. 6, 12, 15 or 18;
   e) a nucleotide sequence encoding a homologue, analogue or orthologue of a polypeptide comprising an amino acid sequence as set forth in SEQ ID No. 6, 12, 15 or 18; or ii) decrease the activity or expression of a polypeptide:
   a) encoded by a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
   b) encoded by a nucleotide sequence that hybridizes with a sequence complementary to one of the nucleotide sequences according to a) under stringent conditions;
   c) comprising an amino acid sequence as set forth in SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18;
   d) which is a homologue, analogue or orthologue of a polypeptide comprising an amino acid sequence as set forth in SEQ ID No. 6, 12, 15 or 18.

In one embodiment protein whose activity or expression is decreased comprises an amino acid sequence shown as SEQ ID No. 6 or a sequence which has at least 80% or at least 85%, preferably at least 90%, at least 92%, or at least 94%, more preferably at least 96%, at least 98%, or at least 99% identity thereto, or a homologue thereof. Suitably, a sucrose/proton antiporter comprises an amino acid sequence shown as SEQ ID No. 6 or a sequence which has at least 80% or at least 85%, preferably at least 90%, at least 92%, or at least 94%, more preferably at least 96%, at least 98%, or at least 99% identity thereto which is capable of functioning as a tonoplast sucrose/proton antiporter, or a homologue of SEQ ID NO.6. Suitably, a homologue of SEQ ID No. 6 may be SEQ ID No. 12 or a sequence which has at least 80% or at least 85%, preferably at least 90%, at least 92%, or at least 94%, more preferably at least 96%, at least 98%, or at least 99% identity thereto which is capable of functioning as a sucrose/proton symporter.

A protein which is capable of functioning as a sucrose/proton symporter is preferably expressed in the tonoplast.

In one embodiment a sucrose/proton symporter comprises an amino acid sequence shown as SEQ ID No. 6 or a sequence which has at least 85%, preferably at least 90%, at least 92%, or at least 94%, more preferably at least 96%, at least 98%, or at least 99% identity thereto. In one embodiment a sucrose/proton symporter comprises an amino acid sequence shown as SEQ ID No. 12, or a sequence which has at least 85%, preferably at least 90%, at least 92%, or at least 94%, more preferably at least 96%, at least 98%, or at least 99% identity thereto.

In one embodiment the sucrose/proton symporter is encoded by a polynucleotide sequence comprising the sequence shown as SEQ ID No. 4, SEQ ID No. 5, SEQ ID No. 10 or SEQ ID No. 11, or a sequence which has at least 80% or at least 85%, preferably at least 90%, at least 92%, or at least 94%, more preferably at least 96%, at least 98%, or at least 99% sequence identity thereto.

Suitably, the sucrose/proton symporter for use according to the present invention may be encoded by a polynucleotide sequence comprising the sequence shown as SEQ ID No. 4, or a sequence which has at least 85%, preferably at least 90%, at least 92%, or at least 94%, more preferably at least 96%, at least 98%, or at least 99% sequence identity thereto. Suitably, the sucrose/proton antiporter for use according to the present invention may be encoded by a polynucleotide sequence comprising the sequence shown as SEQ ID No. 5, or a sequence which has at least 85%, preferably at least 90%, at least 92%, or at least 94%, more preferably at least 96%, at least 98%, or at least 99% sequence identity thereto.

Suitably, sucrose/proton antiporter for use according to the present invention may be encoded by a polynucleotide sequence comprising the sequence shown as SEQ ID No. 10, or a sequence which has at least 85%, preferably at least 90%, at least 92%, or at least 94%, more preferably at least 96%, at least 98%, or at least 99% sequence identity thereto.

Suitably, the sucrose/proton antiporter for use according to the present invention may be encoded by a polynucleotide sequence comprising the sequence shown as SEQ ID No. 11, or a sequence which has at least 85%, preferably at least 90%, at least 92%, or at least 94%, more preferably at least 96%, at least 98%, or at least 99% sequence identity thereto.

In one embodiment protein whose activity or expression is decreased comprises an amino acid sequence shown as SEQ ID No. 15 or a sequence which has at least 80% or at least 85%, preferably at least 90%, at least 92%, or at least 94%, more preferably at least 96%, at least 98%, or at least 99% identity thereto, or a homologue thereof. Suitably, a SWEET protein comprises an amino acid sequence shown as SEQ ID No. 15 or a sequence which has at least 80% identity thereto which is capable of unloading sucrose from the phloem in the shoot, or a homologue of SEQ ID NO.15. Suitably, a homologue of SEQ ID No. 15 may be SEQ ID No. 18 or a sequence which has at least 80% or at least 85%, preferably at least 90%, at least 92%, or at least 94%, more preferably at least 96%, at least 98%, or at least 99% identity thereto which is capable of unloading sucrose from the phloem in the shoot.

A protein which is capable of unloading sucrose from the phloem in the shoot is preferably expressed in shoots.

In one embodiment a SWEET protein comprises an amino acid sequence shown as SEQ ID No. 18 or a sequence which has at least 85%, preferably at least 90%, at least 92%, or at least 94%, more preferably at least 96%, at least 98%, or at least 99% identity thereto.

In one embodiment a sucrose/proton symporter comprises an amino acid sequence shown as SEQ ID No. 18, or a sequence which has at least 85%, preferably at least 90%, at least 92%, or at least 94%, more preferably at least 96%, at least 98%, or at least 99% identity thereto.

In one embodiment the SWEET protein is encoded by a polynucleotide sequence comprising the sequence shown as SEQ ID No. 13, SEQ ID No. 14, SEQ ID No. 16 or SEQ ID No. 17, or a sequence which has at least 80% or at least 85%, preferably at least 90%, at least 92%, or at least 94%, more preferably at least 96%, at least 98%, or at least 99% sequence identity thereto.

Suitably, the SWEET protein for use according to the present invention may be encoded by a polynucleotide sequence comprising the sequence shown as SEQ ID No. 13, or a sequence which has at least 85%, preferably at least 90%, at least 92%, or at least 94%, more preferably at least 96%, at least 98%, or at least 99% sequence identity thereto.

Suitably, the SWEET protein for use according to the present invention may be encoded by a polynucleotide sequence comprising the sequence shown as SEQ ID No. 14, or a sequence which has at least 85%, preferably at least 90%, at least 92%, or at least 94%, more preferably at least 96%, at least 98%, or at least 99% sequence identity thereto.

Suitably, the SWEET protein for use according to the present invention may be encoded by a polynucleotide sequence comprising the sequence shown as SEQ ID No. 16, or a sequence which has at least 85%, preferably at least 90%, at least 92%, or at least 94%, more preferably at least 96%, at least 98%, or at least 99% sequence identity thereto.

Suitably, the SWEET protein for use according to the present invention may be encoded by a polynucleotide sequence comprising the sequence shown as SEQ ID No. 17, or a sequence which has at least 85%, preferably at least 90%, at least 92%, or at least 94%, more preferably at least 96%, at least 98%, or at least 99% sequence identity thereto.

The term "inhibiting" (e.g. inhibiting the activity or expression of a gene) as used herein means that the activity or expression of the gene is lower or decreased compared with the gene activity or expression of the gene in a comparable product.

In some embodiments the activity or expression of a gene may be modulated (i.e. increased or decreased) by at least about 10%20%30%, or 40%, suitably at least about 50%, 60%, 70%, more suitably at least about 80%, 90%, 95% or 100% when compared to the activity or expression of a gene in a plant (e.g. a *Beta vulgaris* plant) which has not been modified in accordance with the present invention. In certain embodiments the activity or expression of a gene may be modulated (i.e. increased) by at least about 200%300% or 500%, suitably at least about 1,000%, 2,000%, 3,000% or 5,000%, more suitably at least about 10,000%, 20,000%, 30,000%, 50,000% or 100,000% when compared to the activity or expression of a gene in a plant (e.g. a *Beta vulgaris* plant) which has not been modified in accordance with the present invention.

Suitably, the expression or activity of the gene comprising a nucleotide sequence as set forth in SEQ ID No. 4, 5, 10, 11, 13, 14, 16 or 17 or variants thereof as defined herein may be reduced, partly inactivated, inhibited, eliminated, knocked out or lost such that the protein expression or function of the protein is not detectable.

In one aspect, the gene comprising a nucleotide sequence as set forth in SEQ ID No. 4, 5, 10, 11, 13, 14, 16 or 17 or variants thereof is knocked out. In other words, the gene comprising a nucleotide sequence as set forth in SEQ ID No. 4, 5, 10, 11, 13, 14, 16 or 17 or variants thereof has been rendered completely inoperative.

Any method known in the art for reducing or preventing the expression or activity of a protein may be used in the methods according to the present invention.

By way of example, the present method may comprise:
providing a mutation in a nucleic acid sequence which encodes a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto;
providing a mutation in a regulatory region (e.g. a promoter or an enhancer) which contributes to controlling the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto;
providing an antisense RNA, siRNA or miRNA which reduces the level of nucleic acid sequence encoding a protein comprising the amino acid sequence shown as SEQ ID No. 6, 12, 15 or 18, or an amino acid sequence which has at least 80% or at least 85%, preferably at least 90%, at least 92%, or at least 94%, more preferably at least 96%, at least 98%, or at least 99% sequence identity thereto.

Each of the above approaches results in the reduction or prevention of expression or activity of a protein comprising the amino acid sequence shown as SEQ ID No. 6, 12, 15 or 18, or an amino acid sequence which has at least 80% or at least 85%, preferably at least 90%, at least 92%, or at least 94%, more preferably at least 96%, at least 98%, or at least 99% sequence identity thereto.

As used herein, the term "mutation" encompasses a natural genetic variant or an engineered variant. In a particular embodiment, the term "mutation" refers to a variation in the nucleotide sequence encoding the amino acid sequence or in the amino acid sequence compared to the sequence shown as SEQ ID No. 3, 6, 9, 12, 15 or 18.

In one embodiment the mutation causes deregulation of phloem flux.

In one embodiment, a method according to the present invention may comprise providing a nucleic acid sequence to a plant or part thereof or plant cell, wherein said nucleic acid results in the reduction or elimination of the expression or activity of a protein comprising an amino acid sequence as set forth in SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18 or a variant thereof described herein. Suitably said nucleic acid sequence may be introduced to the plant or part thereof or cell. Suitably an endogenous nucleic acid sequence in the plant or part thereof or cell may be modified according to the present invention (e.g. by gene editing).

In one embodiment, all of SEQ ID No SEQ ID No. 6, 12, 15 or 18 or a variant thereof described herein may be modified e.g. inhibited or mutated.

In a preferred embodiment the plant or plant cell according to the present invention is homozygous. Suitably, the plant or plant cell may be homozygous for the modification e.g. inhibition or mutation.

In one embodiment, no endogenous (or endogenous and functional protein) is present in the plant according to the present invention. If any endogenous protein is present it is preferably in an inactive form.

In one embodiment the present method may comprise providing a mutation in the nucleic acid sequence shown as SEQ ID No. 4, 5, 10, 11, 13, 14, 16 or 17, or a nucleic acid sequence which has at least 80% or at least 85%, preferably at least 90%, at least 92%, or at least 94%, more preferably at least 96%, at least 98%, or at least 99% identity thereto.

The mutation may alter the plant genome such that a nucleic acid sequence encoding a protein comprising the amino acid sequence shown as SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18 is completely or partially deleted or otherwise made non-functional.

The mutation may interrupt the nucleic acid sequence which encodes a protein comprising the amino acid sequence shown as SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto.

The interruption may cause the nucleic acid sequence to not be transcribed and/or translated.

The nucleic acid sequence may be interrupted, for example, by deleting or otherwise modifying the ATG start codon of the nucleic acid sequence such that translation of the protein is reduced or prevented.

The nucleic acid sequence may comprise one or more nucleotide change(s) that reduce or prevent expression of the protein or affect protein trafficking. For example, expression of the protein may be reduced or prevented by introduction of one or more pre-mature stop codons, a frame shift, a splice mutant or a non-tolerated amino acid substitution in the open reading frame.

A premature stop codon refers to a mutation which introduces a stop codon into the open reading frame and prevents translation of the entire amino acid sequence. The premature stop codon may be a TAG ("amber"), TAA ("ochre"), or TGA ("opal" or "umber") codon.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutant inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein.

Any method known in the art for providing a mutation in a nucleic acid sequence may be used in the method according to the present invention. For example, homologous recombination may be used, in which a vector is created in which the relevant nucleic acid sequence(s) are mutated and used to transform plants or plant cells. Recombinant plants or plant cells expressing the mutated sequence may then be selected.

In one embodiment the mutation introduces a non-tolerated amino acid substitution in a protein comprising an amino acid sequence shown as SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18.

In one embodiment the mutation reduces the activity of the protein in relation to a protein shown as SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18.

In one embodiment the mutation does not alter the level or expression but reduces the activity of the protein in relation to a protein shown as SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18.

The expression of a protein may be measured by measuring the presence of the protein using an antibody specific for the protein, for example by western blot. The activity of a transporter may be measured using a fluorescence based assay and microscopy.

In one embodiment, the protein may contain a mutation which decreases its activity or expression. Suitably, the mutation may alter the cellular localisation of the protein e.g. may prevent expression of the transporter in a membrane. Suitably, the mutation may alter the affinity of the transporter for its substrate.

The mutation may be a deletion, a splice mutant or codon encoding a non-tolerated amino acid substitution.

In one embodiment, the nucleic acid sequence may be wholly or partially deleted. The deletion may be continuous, or may comprise a plurality of sections of sequence. The deletion preferably removes a sufficient amount of nucleotide sequence such that the nucleic acid sequence no longer encodes a functional protein. The deletion may be total, in which case 100% of the coding portion of the nucleic acid sequence is absent, when compared to the corresponding genome of a comparable unmodified plant. The deletion may, for example, remove at least 50, 60, 70, 80 or 90% of the coding portion of the nucleic acid sequence. Suitably, at least part of the protein may be deleted. The deletion may, for example, remove at least 10, 20, 30, 40, 50, 60, 70, 80 or 90% of the coding portion of the protein.

The deletion may remove at least part of the transmembrane domain.

The deletion may, for example, remove at least 10, 20, 30, 40, 50, 60, 70, 80 or 90% of the transmembrane domain.

Suitably, the deletion may remove at least 50 amino acids, at least 100 amino acids, at least 150, at least 200, at least 250, amino acids from the protein. Suitably, the deletion may remove at least 50 amino acids, at least 100 amino acids, at least 150, at least 200, at least 250, amino acids from the protein.

In one embodiment, the deletion may remove at least 100 amino acids, at least 150, at least 200, at least 250, at least 300, at least 350 amino acids from the C terminus of the protein. Suitably, the mutated protein may be a truncated protein which lacks at least about 100 amino acids, at least about 150, at least about 200, at least about 250, at least about 300, at least about 350 amino acids corresponding to the amino acids from the C-terminal of SEQ ID No. 6, 12, 15 or 18 or a sequence which has at least 80% or at least 85%, preferably at least 90%, at least 92%, or at least 94%, more preferably at least 96%, at least 98%, or at least 99% sequence identity thereto to.

The deletion may remove at least part of the active site of the protein. The deletion may remove the active site of the protein.

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

Modification of the nucleic acid sequence may be performed using targeted mutagenesis methods (also referred to as targeted nucleotide exchange (TNE) or oligo-directed mutagenesis (ODM)). Targeted mutagenesis methods include, without limitation, those employing zinc finger nucleases, TALENs (see WO2011/072246 and WO2010/079430), Cas9-like, Cas9/crRNA/tracrRNA, Cas9/gRNA, or other CRISPR systems (see WO 2014/071006 and WO2014/093622), meganucleases (see WO2007/047859 and WO2009/059195), or targeted mutagenesis methods employing mutagenic oligonucleotides, possibly containing chemically modified nucleotides for enhancing mutagenesis with sequence complementarity to the gene, into plant protoplasts (e.g., KeyBase® targeted mutagenesis method or TALENs).

Alternatively, mutagenesis systems such as TILLING (Targeting Induced Local Lesions IN Genomics; McCallum et al., 2000, Nat Biotech 18:455, and McCallum et al. 2000, Plant Physiol. 123, 439-442, both incorporated herein by reference) may be used to generate plant lines which comprise a gene encoding a protein having a mutation. TILLING uses traditional chemical mutagenesis (e.g. ethyl methanesulfonate (EMS) mutagenesis, which produces random mutations) followed by high-throughput screening for mutations. Thus, plants, seeds, cells and tissues comprising a gene having the desired mutation may be obtained. The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Fast neutron deletion mutagenesis may be used in a reverse genetics sense (i.e. with PCR) to identify plant lines carrying a deletion in the endogenous gene. See for example Ohshima et al. (1998) Virology 213:472-481; Okubara et al. (1994) Genetics 137:867-874; and Quesada et al. (2000) Genetics 154:421-4315 which are incorporated herein by reference.

In another approach, dominant mutants may be used to trigger RNA silencing due to gene inversion and recombination of a duplicated gene locus. See for example Kusaba et al. (2003) Plant Cell 15:1455-1467 (incorporated herein by reference).

Modified plants may be distinguished from non-modified plants, i.e., wild type plants, by molecular methods, such as the mutation(s) present in the DNA, and by the modified phenotypic characteristics. The modified plants may be homozygous or heterozygous for the modification. Preferably modified plants are homozygous for the modification.

In one embodiment the method of reducing or preventing the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto does not comprise treating the plant with a chemical (e.g. an agrochemical).

Other ways of reducing or preventing the expression or activity will be apparent to one skilled in the art and include the use of virus-induced gene silencing (VIGS), micro RNA silencing, RNAi, antisense, tDNA insertions, or dominant negative constructs (or antimorphic mutations). In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by virus-induced gene silencing.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by microRNAs.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by RNAi.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by antisense suppression.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by sense suppression.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by tDNA insertions.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by dominant negative constructs (or antimorphic mutations).

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by a targeted mutagenesis based system.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by CRISPR based system.

In one embodiment the expression of a protein comprising the amino acid sequence shown as SEQ ID No. 6, 12, 15 or 18 or an amino acid sequence which has at least 80% or at least 85%, preferably at least 90%, at least 92%, or at least 94%, more preferably at least 96%, at least 98%, or at least 99% sequence identity thereto may be reduced or eliminated by zinc finger nuclease, TALENs, meganucleases, mutagenic oligonucleotides or TILLING.

Commercially Desirable Traits

In one embodiment the plants of the present invention have deregulated phloem flux, whilst the other commercially desirable traits are at least maintained.

In particular the yield of the plant according to the present invention is preferably not reduced compared with a comparable plant which has not been modified in accordance with the present invention.

In one embodiment the plants of the present invention produce storage organs a similar size and/or quality to comparable plants which have not been modified according to the invention. The term "commercially desirable traits" as used herein will include traits such as yield, canopy coverage, mature plant height, quality (e.g. harvested root quality), abiotic (for instance drought) stress tolerance, herbicide tolerance and/or biotic (for instance insect, bacteria or fungus) stress tolerance.

In one aspect, a plant (e.g. a *Beta vulgaris*) of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the plant (e.g. *Beta vulgaris*) yield of the present invention is approximately or at least 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 times of the yield of a comparable plant when grown in similar field conditions.

In one aspect, the plant (e.g. *Beta vulgaris*) yield of the present invention is approximately at least 20 tonnes per hectare, at least 30 tonnes per hectare, at least 40 tonnes per hectare, at least 50 tonnes per hectare, preferably at least 60 tonnes per hectare, such as at least 65, at least 70, at least 75, at least 80, at least 85, at least 90 tonnes or at least 100 tonnes per hectare.

Plant Breeding

The present invention provides a method of producing a cold tolerant plant and/or a plant with delayed or inhibited bolting, comprising crossing a donor plant comprising an allele associated with deregulated phloem flux with a recipient plant that possesses commercially desirable traits.

In one embodiment, the present invention provides a method of producing a cold tolerant plant and/or a plant with delayed or inhibited bolting, comprising crossing a donor plant comprising an allele associated with deregulated phloem flux wherein said allele comprises a polynucleotide sequence comprising:

a) a nucleotide sequence as set forth in SEQ ID No. 1, 2, 4, 5, 7, 8, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 1, 2, 4, 5, 7, 8, 10, 11, 13, 14, 16 or 17;

b) a nucleotide sequence having the coding sequence as set forth in SEQ ID No. 2, 5, 8, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 2, 5, 8, 11, 14 or 17;

c) a nucleotide sequence that hybridizes with a sequence complementary to one of the nucleotide sequences according to a) or b) under stringent conditions;

d) a nucleotide sequence encoding a polypeptide comprising an amino acid sequence as set forth in SEQ ID No. 3, 6, 9, 12, 15 or 18, or a sequence which has at least 80% or at least 85%, preferably at least 90%, at least 92%, or at least 94%, more preferably at least 96%, at least 98%, or at least 99% identity to SEQ ID No. 3, 6, 9, 12, 15 or 18;

e) a nucleotide sequence encoding a homologue, analogue or orthologue of a polypeptide comprising an amino acid sequence as set forth in SEQ ID No. 3, 6, 9, 12, 15 or 18; or f) an allele of any of a), b), c), d) or e);

with a recipient plant that possesses commercially desirable traits.

The method of producing a plant may comprise performing PCR to identify an allele associated with deregulated phloem flux. Suitably, the method may comprise performing PCR to identify an allele comprising:

a) a nucleotide sequence as set forth in SEQ ID No. SEQ ID No. 1, 2, 4, 5, 7, 8, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 1, 2, 4, 5, 7, 8, 10, 11, 13, 14, 16 or 17;

b) a nucleotide sequence having the coding sequence as set forth in SEQ ID No. 2, 5, 8, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 2, 5, 8, 11, 14 or 17;

c) a nucleotide sequence that hybridizes with a sequence complementary to one of the nucleotide sequences according to a) or b) under stringent conditions;

d) a nucleotide sequence encoding a polypeptide comprising an amino acid sequence as set forth in SEQ ID No. 3, 6, 9, 12, 15 or 18, or a sequence which has at least 80% or at least 85%, preferably at least 90%, at least 92%, or at least 94%, more preferably at least 96%, at least 98%, or at least 99% identity to SEQ ID No. 3, 6, 9, 12, 15 or 18;

e) a nucleotide sequence encoding a homologue, analogue or orthologue of a polypeptide comprising an amino acid sequence as set forth in SEQ ID No. 3, 6, 9, 12, 15 or 18; or f) an allele of any of a), b), c), d) or e);

in the resulting offspring or progeny.

Plants

The term "plant" according to the present invention includes whole plants or parts of such a whole plant. Whole plants preferably are seed plants, or a crop. "Parts of a plant" are e.g. shoot vegetative organs/structures, e.g., leaves, stems and tubers; roots, flowers and floral organs/structures, e.g. bracts, sepals, petals, stamens, carpels, anthers and ovules; seed, including embryo, endosperm, and seed coat; fruit and the mature ovary; plant tissue, e.g. vascular tissue, ground tissue, and the like; and cells, e.g. guard cells, egg cells, pollen, trichomes and the like; and progeny of the same.

In one embodiment, the plant (or part thereof or plant cell) is or is from a monocotyledonous plant. In another embodiment, the plant (or part thereof or plant cell) is or is from a dicotyledonous plant.

In a preferred embodiment, the plant (or part thereof or plant cell) is or is from a sugar crop. Suitably, the sugar crop may be sugar beet, sugar cane, sugar palm or sweet sorghum.

In one embodiment, the plant (or part thereof or plant cell) is from the Amaranthaceae family. Suitably, the plant (or part thereof or plant cell) may be from the Betoideae subfamily. The Betoideae subfamily contains several cultivar groups such as sugar beet, beetroot or garden beet, chard or spinach beet and mangel-wurzel which is a fodder crop.

In one embodiment, the plant (or part thereof or plant cell) is from the Beta genus. The Beta genus contains important crops such as sugar beet, chard, beetroot and mangel-wurzel.

In a preferred embodiment, the plant (or part thereof or plant cell) is from the species *Beta vulgaris*.

In a preferred embodiment, the plant (or part thereof or plant cell) is from the subspecies *Beta vulgaris* subsp. *vulgaris*.

The term "*Beta vulgaris*" or "*Beta vulgaris* plant" is understood to refer to a plant of the genus *Beta vulgaris*, e.g. *Beta vulgaris* ssp. *vulgaris* var *altissima* (sugar beet in the narrow sense), *Beta vulgaris* ssp. *maritima* (sea beet), *Beta vurlgaris* ssp. *vulgaris* var *vulgaris* (Mangold beet), *Beta vulgaris* ssp. *vulgaris* var *conditiva* (red beetroot/beet), *Beta vulgaris* ssp. *eras sa vulgaris* var *I alba* (fodder beet).

In another embodiment, the plant (or part thereof or plant cell) is from the Poaceae family.

In one embodiment, the plant (or part thereof or plant cell) is from the Sorghum genus. The Sorghum genus comprises important crops such as cultivated *Sorghum bicolor* which is used for food as grain and in sorghum syrup or sorghum molasses. In one embodiment, the plant (or part thereof or plant cell) is from the species *Sorghum bicolor*.

In one embodiment, the plant (or part thereof or plant cell) is from the Saccharum genus. The Saccharum genus contains important crops such as sugarcane cultivars.

In one embodiment, the plant (or part thereof or plant cell) is from the species *Saccharum officinarum*.

In another embodiment, the plant (or part thereof or plant cell) is from the Arecaceae family.

In one embodiment, the plant (or part thereof or plant cell) is from the Arenga genus. The Arenga genus contains important crops such as sugar palm cultivars.

In one embodiment, the plant (or part thereof or plant cell) is from the species *Arenga saccharifera* or *Arenga pinnata*.

In another embodiment, the plant (or part thereof or plant cell) is from the Sapindaceae family.

In one embodiment, the plant (or part thereof or plant cell) is from the Acer genus. The Acer genus contains important crops such as sugar maple cultivars.

In one embodiment, the plant (or part thereof or plant cell) is from the species *Acer saccharum*.

In one embodiment, the plant (or part thereof or plant cell) is or is from crop plant such as a root vegetable (including true roots such as taproots and tuberous roots and non-roots such as bulbs, corms, rhizomes and tubers).

Suitably, the crop plant may have a taproot. Suitably, the crop plant may be selected from: *Arracacia xanthorrhiza* (arracacha), *Beta vulgaris* (beet and mangelwurzel), *Brassica* spp. (rutabaga and turnip), *Bunium persicum* (black cumin), burdock (*Arctium*, family Asteraceae), carrot (*Daucus carota* subsp. *sativus*), celeriac (*Apium graveolens rapaceum*), Daikon (*Raphanus sativus* var. *longipinnatus*), dandelion (*Taraxacum*) spp., *Lepidium meyenii* (maca), *Microseris lanceolata* (murnong or yam daisy), *Pachyrhizus* spp. (jicama and ahipa), parsnip (*Pastinaca sativa*), *Petroselinum* spp. (parsley root), radish (*Raphanus sativus*), *Scorzonera hispanica* (black salsify), *Sium sisarum* (skirret), *Tragopogon* spp. (salsify), and *Vigna lanceolata* (bush carrot or bush potato).

Suitably, the crop plant may have a tuberous root. Suitably, the crop plant may be selected from: *Amorphophallus galbra* (yellow lily yam), *Conopodium majus* (pignut or earthnut), *Dioscorea polystachya* (nagaimo, Chinese yam, Korean yam, mountain yam), *Hornstedtia scottiana* (native ginger), *Ipomoea batatas* (sweet potato), *Ipomoea costata* (desert yam), *Manihot esculenta* (cassava or yuca or manioc), *Mirabilis expansa* (mauka or chago), *Psoralea esculenta* (breadroot, tipsin, or prairie turnip) and *Smallanthus sonchifolius* (yacón), Suitably, the crop plant may form tubers. Suitably, the crop plant may be selected from: *Apios americana* (hog potato or groundnut), *Cyperus esculentus* (tigernut or chufa), *Dioscorea* spp. (yams, ube), *Dioscorea polystachya* (Chinese yam, white name or white ñame), *Helianthus tuberosus* (Jerusalem artichoke or sunchoke), *Hemerocallis* spp. (daylily), *Lathyrus tuberosus* (earthnut pea), *Oxalis tuberosa* (oca or New Zealand yam), *Plectranthus edulis* and *P. esculentus* (kembili, dazo, and others), *Solanum tuberosum* (potato), *Stachys affinis* (Chinese artichoke or crosne), *Tropaeolum tuberosum* (mashua or añu)

and *Ullucus tuberosus* (ulluku). In one embodiment the plant propagation material may be obtainable (or obtained) from a plant of the invention.

A "plant propagation material" as used herein refers to any plant matter taken from a plant from which further plants may be produced. Suitably, a plant propagation material may be selected from a seed, plant calli and plant clumps. Suitably the plant propagation material may be a seed. Suitably, the plant propagation material may be plant calli. Suitably the plant propagation material may be plant clumps.

In one embodiment the plant cell, plant, plant part and/or plant propagation material may be obtainable (e.g. obtained) by a method according to the invention.

In a particularly preferred embodiment, the plant or part thereof or plant cell is a *Beta vulgaris* plant or part thereof or plant cell. In a particularly preferred embodiment, the plant or part thereof or plant cell is a *Beta vulgaris* subsp. *vulgaris* plant or part thereof or plant cell.

Products

The present invention also provides for products obtainable or obtained from plants according to the present invention.

A product obtainable or obtained from a pant according to the invention may be plant propagation material. Another product obtainable or obtained form a plant according to the invention may be a harvested root.

Suitably the harvested root may be subjected to downstream applications such as processing. Sugar is usually produced from sugar beet chips in an extraction process with water. The extract may then be treated with calcium oxide to precipitate the plants acids such as oxalic acid or tartaric acid and the proteins. The excess lime is separated by introducing carbon dioxide. Through the subsequent evaporation of the water from the sugar solution in a vacuum, a syrupy solution is obtained. The crystallizing sugar is separated from the remaining brown syrup by centrifugation. The residue, the molasses, is used as cattle feed or is used for alcoholic fermentation. Purification of the sugar (refining) is carried out by recrystallization, filtration and by evaporation in a vacuum. In addition, sugar beets cen be used also for the production of biogas or bio-ethanol.

In a further aspect, the present invention provides the use of a plant or part thereof or plant cell according to the present invention for the production of a foodstuff, such as sugar, sugar beet syrup, molasses or a beverage. Suitably, the plant or part thereof or plant cell according to the invention may be used for the production of sugar (e.g. refined sugar). Suitably, the plant or part thereof or plant cell according to the invention may be used for the production of sugar beet syrup. Suitably, the plant or part thereof or plant cell according to the invention may be used for the production of molasses. Suitably, the plant or part thereof or plant cell according to the invention may be used for the production of animal feed. Suitably, the plant or part thereof or plant cell according to the invention may be used for the production of beverages (e.g. alcoholic beverages).

Polynucleotides/Polypeptides/Constructs

In certain embodiments of the present invention, constructs which modulate (i.e. increase or decrease) the activity or expression of at least one gene as defined herein may be transformed into plant cells, suitably under the direction of a promoter.

In certain embodiments of the present invention, constructs are provided which:
i) increase the activity or expression of a gene comprising:
  a) a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7 or 8;
  b) a nucleotide sequence having the coding sequence as set forth in SEQ ID No. 2 or 8, or a nucleotide sequence which has at least 80% or at least 85%, preferably at least 90%, at least 92%, or at least 94%, more preferably at least 96%, at least 98%, or at least 99% identity to SEQ ID No. 2 or 8;
  c) a nucleotide sequence that hybridizes with a sequence complementary to one of the nucleotide sequences according to a) under stringent conditions;
  d) a nucleotide sequence which encodes a polypeptide comprising an amino acid sequence as set forth in SEQ ID No. 3 or 9 or a sequence which has at least 80% or at least 85%, preferably at least 90%, at least 92%, or at least 94%, more preferably at least 96%, at least 98%, or at least 99% identity to SEQ ID No. 3 or 9;
  e) a nucleotide sequence encoding a homologue, analogue or orthologue of a polypeptide comprising an amino acid sequence as set forth in SEQ ID No. 3 or 9; or
ii) increase the activity or expression of a polypeptide:
  a) encoded by a nucleotide sequence as set forth in SEQ ID No. 1, 2, 7 or 8, or a nucleotide sequence which has at least 80% or at least 85%, preferably at least 90%, at least 92%, or at least 94%, more preferably at least 96%, at least 98%, or at least 99% identity to SEQ ID No. 1, 2, 7, or 8;
  b) encoded by a nucleotide sequence that hybridizes with a sequence complementary to one of the nucleotide sequences according to a) under stringent conditions;
  c) comprising an amino acid sequence as set forth in SEQ ID No. 3 or 9; or an amino acid sequence having at least 80% or at least 85%, preferably at least 90%, at least 92%, or at least 94%, more preferably at least 96%, at least 98%, or at least 99% identity to SEQ ID No. 3 or 9;
  d) which is a homologue, analogue or orthologue of a polypeptide comprising an amino acid sequence as set forth in SEQ ID No. 3 or 9.

In other embodiments of the present invention, constructs are provided which:
i) decrease (i.e. inhibit) activity or expression of a gene comprising:
  a) a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;
  b) a nucleotide sequence having the coding sequence as set forth in SEQ ID No. 5, 11, 14 or 17, or a nucleotide sequence which has at least 80% or at least 85%, preferably at least 90%, at least 92%, or at least 94%, more preferably at least 96%, at least 98%, or at least 99% identity to SEQ ID No. 5, 11, 14 or 17;
  c) a nucleotide sequence that hybridizes with a sequence complementary to one of the nucleotide sequences according to a) or b) under stringent conditions;

d) a nucleotide sequence which encodes a polypeptide comprising an amino acid sequence as set forth in SEQ ID No. 6, 12, 15 or 18 or a sequence which has at least 80% or at least 85%, preferably at least 90%, at least 92%, or at least 94%, more preferably at least 96%, at least 98%, or at least 99% identity to SEQ ID No. 6, 12, 15 or 18;

e) a nucleotide sequence encoding a homologue, analogue or orthologue of a polypeptide comprising an amino acid sequence as set forth in SEQ ID No. 6, 12, 15 or 18; or ii) decrease the activity or expression of a polypeptide:

a) encoded by a nucleotide sequence as set forth in SEQ ID No. 4, 5, 10, 11, 13, 14, 16 or 17, or a nucleotide sequence which has at least 80% or at least 85%, preferably at least 90%, at least 92%, or at least 94%, more preferably at least 96%, at least 98%, or at least 99% identity to SEQ ID No. 4, 5, 10, 11, 13, 14, 16 or 17;

b) encoded by a nucleotide sequence that hybridizes with a sequence complementary to one of the nucleotide sequences according to a) under stringent conditions;

c) comprising an amino acid sequence as set forth in SEQ ID No. 6, 12, 15 or 18, or a sequence which has at least 80% or at least 85%, preferably at least 90%, at least 92%, or at least 94%, more preferably at least 96%, at least 98%, or at least 99% identity to SEQ ID No. 6, 12, 15 or 18;

d) which is a homologue, analogue or orthologue of a polypeptide comprising an amino acid sequence as set forth in SEQ ID No. 6, 12, 15 or 18, In some embodiments of the present invention, said constructs are transformed into plant cells under the direction of a promoter. For example, the genetic construct may be a gene editing construct or may comprise an RNAi molecule, which may comprise a small interfering RNA (siRNA) molecule, or a short hairpin loop (shRNA) molecule.

Constructs may be introduced into plants according to the present invention by means of suitable vector, e.g. plant transformation vectors. A plant transformation vector may comprise an expression cassette comprising 5'-3' in the direction of transcription, a promoter sequence, a construct sequence targeting a gene and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The construct of the present invention may also comprise a gene expression enhancing mechanism to increase the strength of the promoter. An example of such an enhancer element is one derived from a portion of the promoter of the pea plastocyanin gene, and which is the subject of International Patent Application No. WO 97/20056 which is incorporated herein by reference. Suitable enhancer elements may be the nos enhancer element derived from the nopaline synthase gene of *Agrobacterium tumefaciens* and the 35S enhancer element from cauliflower mosaic virus, for example.

These regulatory regions may be derived from the same gene as the promoter DNA sequence or may be derived from different genes, from *Beta vulgaris* or other organisms. All of the regulatory regions should be capable of operating in cells of the tissue to be transformed.

The promoter DNA sequence may be derived from the same gene as the gene of interest, e.g. the gene the promoter is going to direct, or may be derived from a different gene, from *Beta vulgaris*, or another organism.

The expression cassette may be incorporated into a basic plant transformation vector, such as pBIN 19 Plus, pBI 101, pKYLX71:35S2, pCAMBIA2300 or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "expression vector or plant transformation vector" means a construct capable of in vivo or in vitro expression. Preferably, the expression vector is incorporated in the genome of the organism. In one embodiment the vector of the present invention expresses a protein e.g. a TST2.1 or TMT1 protein described herein. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* 42:205-225) and Christon (Agro-Food-Industry Hi-Tech March/April1994 17-27), which are incorporated herein by reference. Preferably, the transformation and regeneration of sugar beet is carried out by the method described by Lindsey (Lindsey K. (1991) "Regeneration and transformation of sugar beet by *Agrobacterium tumefaciens*" Plant Tissue Culture Manual B7: 1-13, Kluwer Academic Publishers which is incorporated herein by reference).

Typically, in *Agrobacterium*-mediated transformation a binary vector carrying a foreign DNA of interest, i.e. a construct according to the present invention, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998 Plant J. 1998 December; 16(6):735-43, which is incorporated herein by reference) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208 which is incorporated herein by reference.

Further suitable transformation methods include direct gene transfer into protoplasts using polyethylene glycol or electroporation techniques, particle bombardment, microinjection and the use of silicon carbide fibres for example. Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994) which is incorporated herein by reference. Production of fertile transgenic maize plants by silicon carbide whisker-mediated transformation is taught in *The Plant Journal* 6: 941-948, which is incorporated herein by reference) and viral transformation techniques is taught in for example Meyer P, Heidmann I & Niedenhof I (1992), which is incorporated herein by reference. The use of cassava mosaic virus as a vector system for plants is taught in Gene 110: 213-217, which is incorporated herein by reference. Further teachings on plant transformation may be found in EP-A-0449375, incorporated herein by reference.

In a further aspect, the present invention relates to a vector system which carries a construct and introducing it into the genome of an organism, such as a plant, suitably a *Beta vulgaris* plant. The vector system may comprise one vector, but it may comprise two vectors. In the case of two vectors, the vector system is normally referred to as a binary vector system. Binary vector systems are described in further detail in Gynheung Anetal, (1980), Binary Vectors, *Plant Molecular Biology Manual* A3, 1-19, which is incorporated herein by reference.

One extensively employed system for transformation of plant cells uses the Ti plasmid from *Agrobacterium tumefaciens* or a Ri plasmid from *Agrobacterium rhizogenes* described by An et al., (1986), *Plant Physiol.* 81, 301-305 and Butcher D. N. et al., (1980), *Tissue Culture Methods for Plant Pathologists*, eds.: D. S. Ingrams and J. P. Helgeson, 203-208 which are incorporated herein by reference. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema, in: The Binary Plant Vector System Offset-drukkerij Kanters B. B., Amsterdam, 1985, Chapter V; Fraley, et al., *Crit. Rev. Plant Sci.,* 4:1-46; and Anetal., *EMBO J* (1985) 4:277-284, incorporated herein by reference.

Plant cells transformed with construct(s) which modulate the activity or expression of a protein described herein may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises a construct which modulates the activity or expression of gene according to the invention. Accordingly a transgenic plant is a plant which has been transformed with a construct according to the invention. Preferably the transgenic plant exhibits deregulated phloem flux under cold conditions or post-vernalization. The term "transgenic plant" does not cover native nucleotide coding sequences in their natural environment when they are under the control of their native promoter which is also in its natural environment.

In one aspect, a nucleotide sequence, a gene, a construct, plant transformation vector or plant cell according to the present invention is in an isolated form. The term "isolated" means that the nucleotide sequence, gene, construct, plant transformation vector or plant cell is at least substantially free from at least one other component with which the sequence is naturally associated in nature and as found in nature.

In one aspect, a nucleotide sequence, a gene, a construct, plant transformation vector or plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence as described herein operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals. The term "promoter" is used in the normal sense of the art, e.g. an RNA polymerase binding site. The nucleotide sequence within a construct which encodes a gene may be operably linked to at least a promoter.

The term "construct"-which is synonymous with terms such as "cassette" or "vector"-includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment. The construct may even contain or express a marker, which allows for the selection of the genetic construct.

In some embodiments the promoter may be selected from the group consisting of: a constitutive promoter, a tissue-specific promoter, a developmentally-regulated promoter and an inducible promoter.

In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter. Nature. 313 810-2), the rice actin 1 gene (Zhang W, McElroy D, Wu R. (1991). Analysis of rice Act1 5' region activity in transgenic rice plants. Plant Cell 3 1155-65) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81). Constitutive promoters such as the Carnation Etched Ring Virus (CERV) promoter (Hull R, Sadler J, LongstaffM (1986) (CaMV/35S), figwort mosaic virus 35S promoter. The sequence of carnation etched ring virus DNA: comparison with cauliflower mosaic virus and retroviruses. EMBO Journal, 5(2):3083-3090).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene.

The promoter may be a tissue specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Tissue specific promoters include the phaseolin-promoter, legumin b4-promoter, usp-promoter, sbp-promoter, ST-LS1 promoter, B33 (patatin class I promoter). Other promoters which show increased specificity for the saccharose storage organ or parts thereof, i.e., which are active in particular in this saccharose storage organ or parts thereof can be used in the present invention. For sugar beet, the promoter may be, for example, a root-specific or taproot-specific promoter. The person skilled in the art knows them from the prior art: WO02/40687, Oltmanns, H. et al. (2006) Planta 224: 485-495, Noh, Seal Ah, et al. (2012) Transgenic research 21: 265-278. For sugarcane preferably culm-specific promoters may be used, such as those known from Goshu Abraha, Tsion. "Isolation and characterization of a culm-specific promoter element from sugarcane", diss. Stellenbosch: University of Stellen-bosch, 2005. Govender, C. "Stem specific promoters from sorghum and maize for use in sugarcane", diss. Stellenbosch: Stellenbosch University, 2008; and Mudge, S. R. et al. (2013) Plant Biotechnology Journal 1: 502-509).

In one embodiment, a preferred tissue specific promoter is a taproot specific promoter. Suitably, the taproot specific promoter may be the Feb. 1, 1948 promoter. In one embodiment, a tissue specific promoter for use in the present invention is set forth in SEQ ID No. 19, or a variant thereof having at least 80% sequence identity thereto, provided said variant is capable of directing expression to taproot tissue.

In another embodiment the promoter may be a developmentally-regulated promoter.

A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator (such as auxin and salicylic acid which activate the OCS promoter), or a toxic element, a physiological stress such as heat, light (such as the soybean SSU promoter), wounding (e.g. the nos, nopaline synthase promoter), or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. ((1993) Plant J. 3 191-201), temperature response as disclosed by Benfey & Chua (1989) (Benfey, P. N., and Chua, N-H. ((1989) Science 244 174-181), and chemically induced, as described by Gatz ((1995) Methods in Cell Biol. 50 411-424).

A nucleotide sequence encoding either a protein which has the specific properties for deregulating phloem flux as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

In a further alternative, the nucleotide sequence may be prepared synthetically by established standard methods, e.g. the phosphoroamidite method described by Beucage S. L. et al., (1981) *Tetrahedron Letters* 22, p 1859-1869 which is incorporated herein by reference, or the method described by Matthes et al., (1984) *EMBO J.* 3, p 801-805 which is incorporated herein by reference. In the phosphoroamidite method, oligonucleotides are synthesised, e.g. in an automatic DNA synthesiser, purified, annealed, ligated and cloned in appropriate vectors.

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the gene. For example, a homologue of a sucrose transporter will function as a sucrose transporter and a homologue of a sucrose/proton antiporter will function as a sucrose/proton antiporter. Typically, homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity. Homologous sequences typically retain functional domains or motifs.

In one embodiment, a homologous sequence is taken to include an amino acid sequence or nucleotide sequence which has one, two or several additions, deletions and/or substitutions compared with the subject sequence.

Sequence Identity

Sequence identity comparisons can be conducted by eye, or more usually, with the aid of readily available sequence comparison programs. These commercially available computer programs can calculate % homology between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology. However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. 1999 Short Protocols in Molecular Biology, 4th Ed-Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al. 1990 J. Mol. Biol. 403-410) and AlignX for example. At least BLAST, BLAST 2 and FASTA are available for offline and online searching (see Ausubel et al. 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should gap penalties be used when determining sequence identity, then preferably the following parameters are used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above. In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 50 contiguous nucleotides, preferably over at least 60 contiguous nucleotides, preferably over at least 70 contiguous nucleotides, preferably over at least 80 contiguous nucleotides, preferably over at least 90 contiguous nucleotides, preferably over at least 100 contiguous nucleotides, preferably over at least 150 contiguous nucleotides, preferably over at least 200 contiguous nucleotides, preferably over at least 250 contiguous nucleotides, preferably over at least 300 contiguous nucleotides, preferably over at least 350 contiguous nucleotides, preferably over at least 400 contiguous nucleotides, preferably over at least 450 contiguous nucleotides, preferably over at least 500 contiguous nucleotides, preferably over at least 550 contiguous nucleotides, preferably over at least 600 contiguous nucleotides, preferably over at least 650 contiguous nucleotides, or preferably over at least 700 contiguous nucleotides. Suitably, the degree of identity with regard to a nucleotide, cDNA, cds or amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur, i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, ß-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid#and L-Phe (4-benzyl)*. The notation * has been utilised for the purpose of the discussion above (relating to homologous or non-homologous substitution), to indicate the hydrophobic nature of the derivative whereas #has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or ß-alanine residues. A further form of variation, involves the presence of one or more amino acid residues in peptoid form, which will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses sequences that are complementary to the nucleic acid sequences of the present invention or sequences that are capable of hybridising either to the sequences of the present invention or to sequences that are complementary thereto. The term "hybridisation" as used herein shall include "the process by which a strand of nucleic acid joins with a complementary strand through base pairing" as well as the process of amplification as carried out in polymerase chain reaction (PCR) technologies.

The terms "hybridizing" and "hybridization" refer to a process in which a single-stranded nucleic acid molecule is added to a nucleic acid strand that is complementary to the greatest possible extent, i.e., enters into base pairing. Standard methods for hybridization are described in Sambrook et al. 2001, for example. Preferably at least 80%, more preferably at least 85%, even more preferably at least 90%, 91%, 92%, 93%, 94%, 95%, 96%, 97%, 98% or 99% of the bases of the nucleic acid molecule enter into a base pairing with the nucleic acid strand that is complementary to the greatest possible extent. The possibility of such an addition depends upon the stringency of the hybridization conditions. The term "stringency" relates to the hybridization conditions. High stringency is present when a base pairing is made more difficult; low stringency is present if a base pairing is made easier. For example, the stringency of the hybridization conditions depends upon the salt concentration, or ion strength, and the temperature. In general, the stringency may be increased by increasing the temperature and/or decreasing the salt content. With "stringent hybridization conditions" is meant herein those conditions under which a hybridization predominantly occurs only between homologous nucleic acid molecules. The term "hybridization conditions" thereby relates not only to the conditions prevailing in the actual addition of the nucleic acids, but also to the conditions prevailing in the following washing steps. Stringent hybridization conditions are, for example, conditions under which, predominantly, only those nucleic acid molecules are hybridized that have at least 80%, preferably at least 85%, at least 90% or at least 95% sequence identity. Stringent hybridization conditions are, for example, hybridization in 4×SSC at 65° C., and subsequent repeated washing in 0.1×SSC at 65° C. for approximately 1 hour in total. The term "stringent hybridization conditions" that is used here may also mean hybridization at 68° C. in 0.25 M sodium phosphate, pH 7.2, 7% SDS, 1 mM EDTA and 1% BSA for 16 hours, and subsequent washing twice with 2×SSC and 0.1% SDS at 68° C. A hybridization preferably occurs under stringent conditions.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a gene" or "an enzyme" includes a plurality of such candidate agents and equivalents thereof known to those skilled in the art, and so forth.

Advantages

The present inventors have surprisingly determined that phloem flux transition occurs after exposure to cold temperatures (such as post-vernalization) but pre-bolting i.e. before the formation of an inflorescence that would act as a new sink organ utilizing remobilised taproot sugars as building blocks.

It has been surprisingly found that by deregulating the phloem flux in a plant or part thereof, the cold tolerance of said plant or part thereof may be increased and/or bolting of said plant can be prevented or inhibited post-vernalization.

Plants suitable for growing in cold conditions which maintain yield and sucrose content in harvestable roots are provided by the present invention. *Beta vulgaris* according to the present invention can be sown earlier, leading to a longer growing season leading to higher biomass and higher sugar yield. Suitably, the plants may be grown as "winter" beets. This allows the farmer an additional crop rotation.

The present invention may provide the following advantages: production of non-shoot emergent, non-flowering *Beta vulgaris* plants; production of a *Beta vulgaris* plant as winter beet; production of a *Beta vulgaris* plant as spring beet; increasing the biomass of the *Beta vulgaris* plant; increasing the sugar yield; avoiding *Beta vulgaris* bolters; extension of the *Beta vulgaris* harvesting campaign; avoidance of losses in *Beta vulgaris* storage material; utilization of the higher humidity in the fall; covering of soil and use of the stored nitrogen; and/or protection for beneficial insects in the field.

The publications discussed herein are provided solely for their disclosure prior to the filing date of the present application. Nothing herein is to be construed as an admission that such publications constitute prior art to the claims appended hereto.

EXAMPLES

Materials and Methods

Materials and Methods

Plant Material and Growth Conditions

Three hybrid sugar beet genotypes (GT1, GT2, GT3; KWS SAAT SE, Germany) were used for this study. Plants were germinated and grown on standard soil substrate ED73 (Einheitserdwerke Patzer, Germany)/10% (v/v) sand mixture under a 10 h light/14 h dark regimen, 60% relative humidity, and 110 µmol m−2 s−1 light intensity. For growth- and sugar accumulation kinetics, plants were grown for 6 weeks at 20° C., transferred for 1 week at 12° C. and then 3 weeks at 4° C. For RNA-seq and proteome analysis, plants were grown for 10 weeks at 20° C., transferred for 1 week at 12° C. and then 2 weeks at 4° C. Control plants were kept at 20° C. For harvest, plants were dissected into shoot and taproot tissues. 4 pools out of three different plants were made for each tissue. Tissues were chopped with a kitchen knife, transferred to liquid nitrogen, and kept at −80° C. until further processing.

Chlorophyll Fluorescence Measurements

Photosynthetic activity was measured using an Imaging-PAM M-Series-System (Heinz Walz, Effeltrich, Germany). Plants were placed in the dark for 12 min to deplete the energy of PSII. Afterwards, capacity of PSII was measured by saturating it with a series of PAR 76 (µmol photons m−2 s−1) light-pulses, as listed in Table 1. Recorded fluorescence was used for calculation of the effective quantum yield of PSII [Y(II)=(Fm'−F)/Fm'], quantum yield of regulated energy dissipation [Y(NPQ)=1−Y(II)−1/(NPQ+1+qL(Fm/Fo−1))] and of non-regulated energy dissipation [Y(NO)=1/(NPQ+1+qL(Fm/Fo−1))]. Required factors were calculated by the formulas $$[NPQ=(Fm-Fm')/Fm'], [qN=(Fm-Fm')/(Fm-Fo')],$$
$$[Fo'=Fo/(Fv/Fm+Fo/Fm')], [qP=(Fm'-F)/(Fm'-Fo')] \text{ and } [qL=(Fm'-F)/(Fm'-Fo')\times Fo'/F=qP\times Fo'/F$$

TABLE 1

Program for measurements of photosynthetic activity

| Time[s] | Light Impulse | |
|---|---|---|
| 0 | PAR 76 | |
| +50 | PAR 76 | |
| +20 | PAR 76 | 14 cycles |

Gas Exchange Measurements

A GFS-3000-system (Heinz Walz, Effeltrich, Germany) was employed to analyze gas exchange-related parameters. A 2.5 cm$^2$ gas exchange cuvette was used to measure $CO_2$-assimilation rate, respiration, leaf $CO_2$ concentration, and transpiration of sugar beet source leaf. Leaf regions including large central mid ribs were omitted. The conditions inside of the cuvette were set to the same temperature, humidity and $CO_2$-concentration the plants had been grown at. Measurement sequence is listed in Table 2. The listed intervals were determined by a trial-experiment, in which the time necessary for stabilization of the flow of $CO_2$ after transfer of the leaf section into the cuvette and adoption to the changed light-intensities was measured. The measurement was started after stabilization of the $CO_2$-flow, which required about 5 minutes. Measurements were performed with 4 biological and 3 technical (repeated measurements of the same plant) replicates over a time of 1 min for each condition to account for variation caused by observed natural leaf-fluctuation and leaf area outside of the cuvette. The 30 second interval between the measurements was necessary for the leaf to return to the stabilized value.

TABLE 2

Program for gas-exchange measurements

| Time[s] | Light-intensity | Measurement |
|---|---|---|
| +0 | PAR 0 | |
| +220 | PAR 0 | photosynthetic activity |
| +30 | PAR 0 | photosynthetic activity |
| +30 | PAR 0 | photosynthetic activity |
| +460 | PAR 125 | respiration/transpiration (light) |
| +30 | PAR 125 | respiration/transpiration (light) |
| +30 | PAR 125 | respiration/transpiration (light) |
| +320 | PAR 0 | respiration/transpiration (dark) |
| +30 | PAR 0 | respiration/transpiration (dark) |
| +30 | PAR 0 | respiration/transpiration (dark) |

Respiration of Sugar Beet Taproot Tissue

Respiration of taproots was measured by cutting out 0.5 cm$^2$ tissue cubes from central taproot regions and measuring $CO_2$ production in a whole-plant cuvette with a volume of 60 cm$^3$. Values were normalized to tissue weight.

RNA Extraction and Sequencing

RNA was isolated from three biological replicates per genotype, tissue (leaf and root, respectively) and treatment, respectively. About 100 mg frozen plant material were pulverized in a tissue lyser (Qiagen, Hilden, Germany) at 30 Hz for 90 sec. After grinding, samples were again transferred to liquid N2, supplemented with 1.5 ml QIAzol Lysis reagent (Qiagen, Hilden, Germany), vortexed three times for 30 sec, and centrifuged at 4° C. for 10 min at 12,000 g. Supernatants were transferred to fresh tubes, incubated at room temperature (RT) for 5 min, extracted with 300 µl chloroform, vortexed for 15 sec, and centrifuged at 4° C. for 15 min at 12,000 g. Aqueous supernatants were transferred to fresh tubes and RNA precipitated with 750 µl isopropanol for 10 min at RT and spun down at 4° C. for 10 min at 12,000 g. Precipitates were washed with 75% EtOH and the RNA pellets dried at 37° C. for 5-10 min prior to resuspension in 100 µl DEPC-H2O by gentle shaking at 37° C. for 5-10 min. To remove residual contaminants, RNA was further purified using the RNeasy KIT (Qiagen, Hilden, Germany). Per 100 µL RNA suspension, 350 µl RLT buffer (provided with the kit) were added and vortexed briefly. Then, 250 µl ethanol were added and the mixture was vortexed again. The RNA was spin-column purified and finally eluted from the column for a final volume of 50 µl (in DEPC-H2O) per sample. The RNA was quantified (NanoDrop 2000/2000c, Thermo Fisher) for each sample prior to further processing or storage at −80° C. RNA quality was confirmed using an Agilent Technologies 2100 Bioanalyzer (Pal Alto, CA, USA). RNAs (2 µg per sample) were transcribed to cDNAs and sequenced using an Illumina, Inc. HiSeq 2000 system. Sequencing and assembly were provided as a custom service (GATC GmbH, Konstanz, Germany). The statistical analysis process included data normalization, graphical exploration of raw and normalized data, test for differential expression for each feature between the conditions and raw p-value adjustment. The analysis was performed using the R software, Bioconductor (Gentleman et al., 2004. Genome biology 5: R80, incorporated herein by reference) packages including DESeq2 (Anders and Huber, 2010 Genome biology 11: R106; Love et al., 2014 Genome biology 15: 550 both of which are incorporated herein by reference) and the SARTools package developed at PF2—Institute Pasteur.

Phylogenetic Analysis

Multiple sequence alignments of amino acid sequences were performed using Clustal Omega (Sievers et al., 2011 Mol Syst Biol 7: 539, incorporated herein by reference). Bayesian phylogenetic analysis was performed with MrBayes version 3.2 (Ronquist et al., 2012 Systematic Biology 61: 539-542, incorporated herein by reference). MrBayes always selected the best-fit models 'Jones' (Jones et al., 1992 Bioinformatics 8: 275-282, incorporated herein by reference) and 'WAG' (Whelan and Goldman, 2001 Molecular biology and evolution 18: 691-699, incorporated herein by reference) for amino acid substitution analysis of SPS proteins and SUS proteins, respectively. MrBayes conducted two parallel Metropolis coupled Monte Carlo Markov chain analysis with four chains for 300,000 generations. Trees were sampled every 1,000 generations. The analyses were run until the standard deviation of split frequencies were below 0.005. Consensus trees were computed after burn-in of the first 25% of trees and visualized using FigTree version 1.4.3.

PCA and Heatmap Analysis

For RNAseq data the mean cpm values were used for the analysis. Data were visualized using ClustVis (Metsalu and Vilo, 2015 Nucleic acids research 43: W566-W570, incorporated herein by reference).

Analysis of Soluble Sugars and Starch

Leaves and taproots were harvested separately, frozen in liquid nitrogen, freeze-dried and stored at −80° C. until use. Pulverized material was extracted twice with 1 ml 80% EtOH at 80° C. for 1 h. Combined extracts were evaporated in a vacufuge concentrator (Eppendorf, Hamburg, Germany) and pellets were resolved in ddH2O. For starch isolation pellets were washed with 80% EtOH and 1 ml ddH20. 200 µl water were added to the pellet and the sample was autoclaved for 40 min at 121° C. 200 µl enzyme-mix (5 U α-Amylase; 5 U Amyloglucosidase in 200 mM Sodium-Acetate pH 4.8) were added to the pellet and starch was hydrolytically cleaved into glucose-units at 37° C. for 4 h. The enzymatic digestion was stopped by heating the samples to 95° C. for 10 min. After centrifugation (20,000 g; 10 min; 21° C.) the supernatant could be used for starch quantification. Extracted sugars and hydrolytically cleaved starch were quantified using a NAD+-coupled enzymatic assay.

Analysis of Phosphorylated Metabolites

The contents of phosphorylated intermediates (Glucose-6-Phosphate, Fructose-6-Phosphate, Sucrose-6-Phosphate, UDP-Glucose, UDP) were determined according to (Horst et al., 2010 Plant Physiol. 152:293., incorporated herein by reference).

Radiolabeled Sucrose Translocation Assay

Ten- to 12-week old sugar beet plants grown at 20° C. under short day conditions (10 h light, 14 h darkness) were used for the analysis. Plants for cold-treatment were grown for 1 more week at 12° C. and then kept for 6 to 7 days at 4° C. Taproots from 4° C. and 20° C. plants were partially uncovered from surrounding soil substrate and a 1 mm hole punched with a biopsy stance into the upper half of the taproot (approximately 1 cm below the soil surface). The created pit was filled with 10 μl of 1 to 2 diluted radiolabeled sucrose (536 mCi/mmol) (Hartmann Analytic, Braunschweig, Germany) and coated with a drop of Vaseline. Plants were then kept for another 10 days at 4° C. or 20° C. (control). At the end of the treatment, all source leaves of injected plants were detached and individually pressed between blotting paper. For detection of radioactivity in taproots, taproots were dug out, washed and cut in thin slices (approximately 0.5 mm thick) with a truffle slicer and pressed between blotting paper. Radioactivity was recorded with Phosphor-Image plates (exposed for 4 to 5 h to adaxial surface of pressed and dried leaves or to dried taproot slices) and plates were analyzed with a Cyclone Storage Phosphor Screen (Packard Bioscience, Meriden, CT, USA). For quantification of radioactivity in petioles, source leaf petioles from the same leaves used for phosphoimaging were cut off, ground, and pulverized. 5 to 10 mg powder were mixed with 2 ml scintillation cocktail and counts per minute (cpm) recorded with a TRI-Carb 2810TR liquid scintillation analyzer (Perkin Elmer, Waltham, MA, USA).

In Planta Esculin Transport

Ten-week old sugar beet plants grown at 20° C. under short day conditions (10 h light, 14 h darkness) were used for the analysis. One source leaf per plant (usually from leaf stage 10 to 12) was abraded at the adaxial side with fine sandpaper (grade 800). About 500 μl of a 100 mM esculin sesquihydrate (Carl Roth, Karlsruhe, Germany) solution was distributed over the injured leaf surface with a plastic pipette. Treated leaves were coated with plastic foil, kept for 2 more days at 20° C. and then transferred to 4° C. or kept at 20° C. (control). After 5 to 7 days in the cold, not esculin-loaded source leaves were detached and sections of petioles were analyzed for esculin fluorescence with a Leica TCS SP5II confocal microscope (Leica, Mannheim, Germany) using a HCX PL APO lamda blue 20.0×0.70 IMM UV objective. Slices of taproots from the very same plants were analyzed for esculin fluorescence to ensure that esculin was successfully translocated into taproots in both cold-treated and control plants. The emission bandwidths were 440-465 nm for detection of esculin fluorescence and 594-631 nm for lignin fluorescence.

Soluble Protein Extraction

Plants were harvested, washed, and separated in the cold into taproots and source leaves. Frozen leaf-tissue was pulverized with N2(I) using a Retsch mill (Retsch GmbH, Germany). 800 μl buffer E1 (50 mM HEPES-KOH PH 7.5, 10 mM MgCl2, 1 mM EDTA PH 7.5, 2 mM DTT, 1 mM PMSF, 1 mM Pefabloc, 5 mM aminohexanoic acid, 0.1% (v/v) Triton X-100, 10% (v/v) glycerol) were transferred to 100 mg of pulverized tissue into 1.5 ml Eppendorf cups. Samples were vortexed and centrifuged for 3 min at 12.000g at 4° C. 500 μL of the supernatant were loaded onto a Sephadex NAP5 (G25) column (GE Health Care, United Kingdom), pre-equilibrated with buffer E1 w/o Triton X-100. Eluents were collected in precooled Eppendorf cups and stored at −20° C. Taproot tissues were treated as above with the following alterations: Taproots were blended with buffer E1 at 4° C. until a homogenous pulp was obtained. The pulp was roughly filtered through a kitchen sieve and centrifuged. 5 ml of the supernatant were dialyzed trough a membrane with 12 kDa pore size for 48 h against 2 L ddH2O. Water was exchanged seven to eight times. Samples were collected in precooled Eppendorf cups and used for enzymatic tests or stored at −20° C. Liquid chromatography and tandem mass spectrometry was performed.

Isolation of Taproot Vacuoles and Vacuolar Proteins

Vacuoles were isolated as described by (Jung et al., 2015 Nature Plants 1: 14001.) with the following modifications. *Beta vulgaris* taproot tissue was cut in thin slices (approximately 0.5 mm thickness) with the help of a truffle slicer. The slices were cut into small cubes with a razor blade. Taproot-cubes were then transferred to 130 ml Collection buffer (750 mM mannitol; 5 mM EDTA pH 8; 50 mM Tris HCl PH 7.6; 1 mM DTT) and incubated on ice for 15 minutes with slight agitation. The solution was filtered through a kitchen sieve and a stainless steel sieve (125 μm mesh size) afterwards. Vacuoles and other cellular compartments were sedimented by centrifugation (2,000 g; 10 min; 4° C.). The sediment was resuspended in 40 ml Centrifugation buffer (Collection buffer+30% (w/v) Nycodenz (AxisShield, Heidelberg, Germany)) and transferred to Sorval centrifugation tubes (36 ml). During centrifugation in the subsequent Sorval SS-34 fixed angle rotor (1,000 g; 15 min; 4° C.) intact vacuoles float to the upper phase of the self-forming Nycodenz-gradient. Intact vacuoles were aliquot in 1 ml fractions added with 1 μl Pefabloc proteinase inhibitor (Sigma Aldrich Merck, Darmstadt, Germany) was added in order to block protease activity. For precipitation of vacuolar proteins, isolated vacuoles were mixed with 20% Trichloroacetic-acid in a 1:1 (v/v) ratio and were incubated at −20° C. for one hour. After incubation samples were centrifuged (20,000 g; 10 min; 4° C.) and washed with 100% Ethanol and 100% acetone twice. The protein pellet was resuspended in 8 M Urea und used for MS analysis. Liquid chromatography and tandem mass spectrometry was performed as described in (Jung et al., 2015 supra).

Sucrose Phosphate Synthase Assay

80 μg of soluble protein were added to 200 μl freshly made Emax (50 mM HEPES-KOH PH 7.5, 20 mM KCl, 4 mM MgCl2, 12 mM UDP-Glc, 10 mM Frc-6-P:Glc-6-P (1:4)), Elim (50 mM HEPES-KOH PH 7.5, 20 mM KCl, 4 mM MgCl2, 4 mM UDP-Glc, 2 mM Frc-6-P:Glc-6-P (1:4), 5 mM KH2PO4) and Eblank (=Emax w/o UDP-glucose and sugar-phosphates), respectively. Samples were incubated for 20 min at 25° C., followed by 5 min at 95° C. to stop the reaction and centrifuged at 12.000 g at 4° C. for 5 min. 100 μL of the supernatant were pipetted to 100 μL 5 M KOH and incubated 10 min at 95° C. The solution was mixed with 800 μL anthrone (14.6 M H2SO4, 0.14% (w/v) anthrone) and absorbance immediately measured at 620 nm. A calibration-standard was made with 0-5 mmol sucrose.

Subcellular Localization of BvSUT4 in *Arabidopsis* and Sugar Beet Mesophyll Protoplasts The BvSUT4 CDS (Bv5_124860_zpft.t1=BVRB_5g124860) was amplified from *B. vulgaris* leaf RNA with the gene specific primers BvSUT4-CACC-f (5'-CAC CAT GAC AGG CCA GGA CCA AAA TA-3' (SEQ ID NO: 20)) and BvSUT4-rev (5'-TAC ATG CAT CAC ATG AAC TCT GG-3' (SEQ ID NO: 21)). The resulting open reading frame was cloned into pENTR/D-TOPO (Life Technologies, Darmstadt, Germany), sequenced and recombined into the Gateway-compatible destination vector pK7FWG,0 to obtain a p35S::BvSUT4-GFP fusion. Transient transformation of *A. thaliana* mesophyll protoplasts was performed as described (Abel and Theologis, 1994 The Plant Journal 5: 421-427, incorporated herein by reference). Isolation and transient transformation of *B. vulgaris* mesophyll protoplasts were performed as described (Nieberl et al., 2017 Plant Biology 19:315-326, incorporated herein by reference.).

Example 1—Cold Exposure Causes Rapid Loss of Shoot and Root Water, but not of Shoot Biomass Production To resolve cold-dependent growth dynamics of sugar beet source and sink organs, shoot and taproot weights of plants from three different hybrid genotypes (GT1, GT2, and GT3) were monitored, (plants were initially grown under control conditions [20° C.], then acclimated for one week at 12° C.) then for 19 days plants were transferred to cold (4° C.) conditions (FIG. 1). Shoot dry weight (DW), but not fresh weight (FW) continued to increase during the exposure of the plants to 4° C. Consequently, shoot water content gradually decreased by almost half at the end of the recorded time (FIG. 1A). Simultaneously, FW but also DW of taproots decreased together with the taproot water content during the cold exposure period (FIG. 1A, B). These results showed that growth of taproots was more affected than that of shoots in the cold and suggested differential physiological and metabolic responses of the shoot and root tissues to cold exposure.

Example 2—Sugar Levels Behave Differently in Shoots and Taproots in the Cold

In our cold-dependent growth analysis leaf material (obtained from the same sugar beet plants as were used for biomass and water content calculation (FIG. 1A)) exhibited a clear increase in the levels of glucose and fructose (and to a lesser extent of the disaccharide sucrose) after transfer to 4° C. (FIG. 1C). In contrast to soluble sugars, leaf starch contents in all three genotypes decreased rapidly after transfer to 4° C., reaching 20 to 33% of the value present prior to transfer (FIG. 1C, rightmost panel).

In taproot tissue, sugar accumulation dynamics differed markedly from those in shoots. Although glucose and fructose levels slightly increased in the cold, they reached only between 10 to 20 percent of the monosaccharide concentrations of leaves. Prior to transfer to 4° C., taproot sucrose levels exceeded those of monosaccharides 30- to 100-fold. Taproot starch levels of all genotypes were extremely low and hardly changed during cold treatment (FIG. 1D). The three genotypes analyzed, however, exhibited different sugar and starch accumulation dynamics in the cold. While GT2 and GT3 taproot sucrose levels clearly decreased in the cold, GT1 sucrose levels fluctuated only marginally. Interestingly, the steep drop in sucrose concentration in taproots of GT3 (by about 400 μmol/g DW) and to a lesser extent of GT2 (by about 200 μmol/g DW) was not accompanied by a proportionate increase of monosaccharides, as would be expected for an exclusive hydrolysis of sucrose. These massive losses of taproot sucrose rather suggested that this sugar was either (i) increasingly respired, (ii) converted into compounds other than the monosaccharides glucose and fructose, or (iii) exported from the taproot tissue into other organs.

Figure 2:
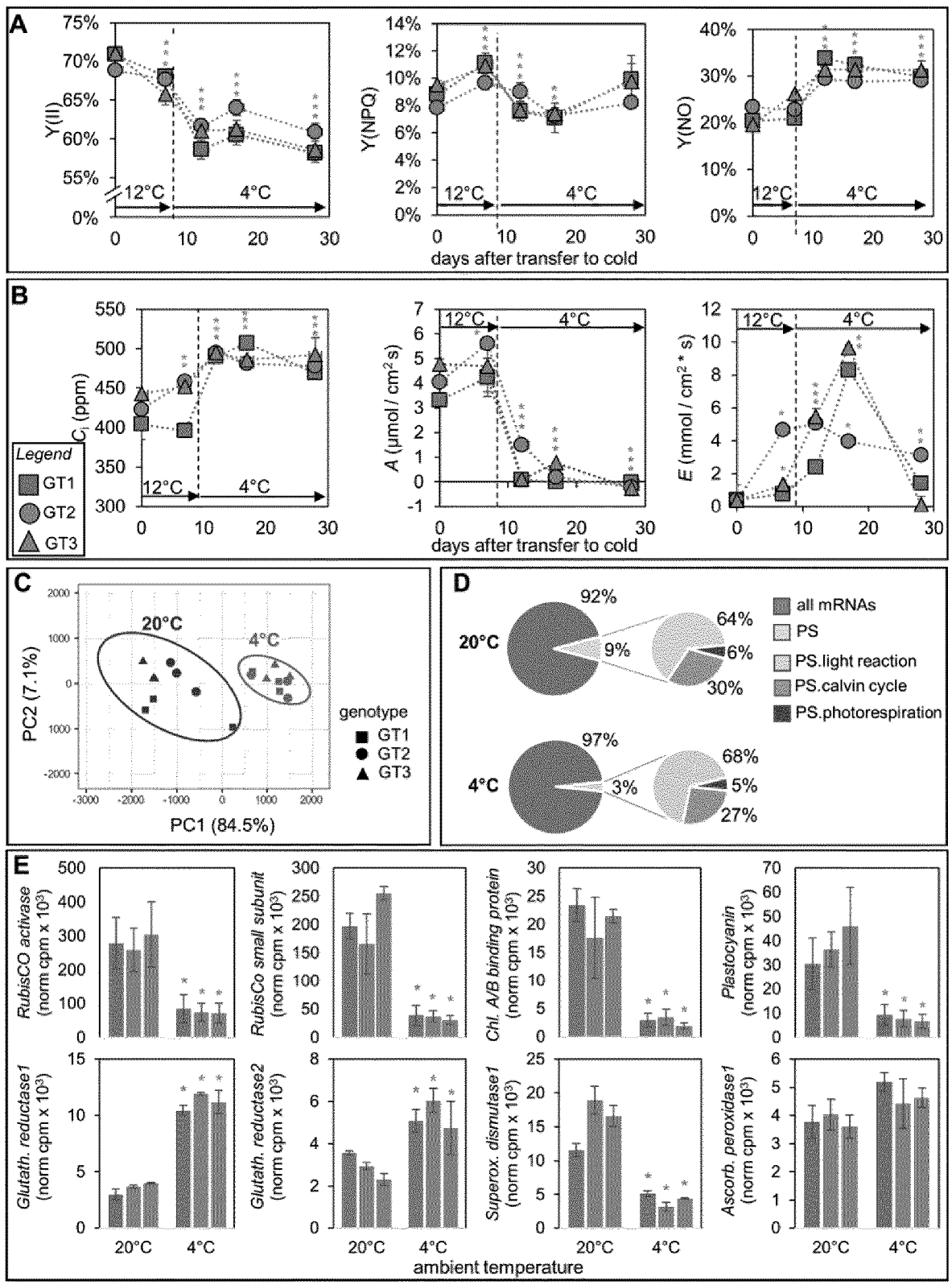
FIG. 2 shows photosynthetic parameters, $CO_2$ assimilation and expression data of sugar beet leaves after cold exposure. Sugar beet plants of three genotypes (GT1=square; GT2=circle; GT3=triangle) were grown for six weeks at 20° C. and then transferred to 12° C. for one week and then to 4° C. for three weeks. (A) PAM measurements of leaves of the three different genotypes. Quantum yield of photosynthesis [Y(II)], of non-photochemical quenching [Y(NPQ)], and of non-regulated quenching [Y(NO)]. At each time point four plants per genotype were analyzed. (B) Gas exchange measured for the same plants as used in (A). Intercellular leaf $CO_2$ concentration ($C_i$), $CO_2$ assimilation rate (A), and transpiration rate (E) are depicted. For each measurement, four independent plants were used. The same plants were used for the measurements at the different time points after transfer to cold conditions. Significant changes to the control condition (first data point) were calculated using Student's t-test (*=p<0.05). (C) Principal component analysis (PC1 versus PC2) for three genotypes based on expression values of 162 photosynthesis-related genes extracted from RNA-seq data of source leaves from plants grown at 20° C. after exposure to 4° C. or to control conditions (20° C.) for 14 days, respectively. (D) Percentage of RNA-Seq reads annotated as genes coding for photosynthesis (PS) related proteins. Pie charts represent the averaged means from three different genotypes at 20° C. (control) and after 14 days at 4° C. Left pie charts show all mRNAs and mRNA of PS related proteins, right pie charts specifies the mRNA of PS related proteins in the groups: PS.light reaction, PS.calvin cycle and PS. Photorespiration. (E) Expression of RubisCO Activase (Bv2_025300_tzou.t1), RubisCO small subunit (Bv2026840_jycs_t1), Chlorophyll A/B binding protein A (Bv_002570_dmif.t1, Plastocyanin (Bv_004160_hgjn.t1), Glutathione reductase 1 (Bv3_069540_erom.t1), Gluthathione reductase2 (Bv5_120360_jpwm.t1), Superoxide dismutase 1 (Bv5_102420_sxsu.t1), Ascorbate peroxidase1 (Bv1_007470_ymzt.t1). Data represent the mean normalized cpm values of three independent RNA-seq analyses per genotype and temperature condition±SD. Asterisks represent p-values <0.05 according to double sided t-test in comparison to the values at control condition (20° C.). The three tested genotypes are represented as three bars, wherein the first bar is GT1, the second bar is GT2 and the third bar is GT3.

Example 3—Cold Exposure Affects Photosynthesis Rate and Carbon Dioxide Assimilation To analyze the impact of cold on sugar beet photosynthesis, we measured the photosynthetic efficiencies of source leaves of the three different genotypes upon exposure to chilling temperatures with pulse amplitude modulated (PAM) fluorometry and $CO_2$ assimilation with gas exchange measurements (FIG. 2). These measurements revealed that Photosystem II quantum yield (Y(II)), leaf $CO_2$ concentrations ($C_i$), $CO_2$ assimilation rate (A), and leaf transpiration rate (E) were dependent on the ambient temperature and that plants exposed to cold responded with a decline in photosynthetic efficiency (FIG. 2). All three genotypes showed a slight but significant reduction of Y(II) already after one week transfer to 12° C. Simultaneously, non-photochemical quenching Y(NPQ), but not non-regulated quenching Y(NO) increased at this temperature in the leaves of all three genotypes (FIG. 2A). The higher Y(NPQ) quantum yield at 12° C. compared to 20° C. indicated an increased flow of electrons towards the Mehler-Ascorbate peroxidase pathway upon exposure to this temperature to undergo e.g. thermal energy dissipation at Photosystem II reaction centers. After transfer to 4° C., Y(II) decreased further and did not recover over the time period tested. However, the decrease of Y(NPQ) quantum yield and the significant increase in Y(NO) quantum yield indicated that electrons were not diverted towards the water cycle, but instead underwent unregulated energy dissipation possibly inducing the membrane damages and free radicals at this low temperature (FIG. 2A). Measurements of $CO_2$ gas exchange clearly showed that the reduced PSII activity, as determined by PAM fluorometry was accompanied by a drastic decline of the $CO_2$ assimilation rate at 4° C. but not at 12° C. (FIG. 2B). Transpiration rates (E) increased in all three genotypes already at 12° C. but more severely at 4° C. The elevated transpiration coincided with a chilling-dependent increase in the leaf $CO_2$ concentration, indicating that despite increased stomata opening, activities of Calvin cycle enzymes were greatly reduced (FIG. 2B). Particularly, GT2 plants (circles in FIG. 2B) responded with increased stomata opening and increased transpiration following transfer to 12° C. resulting in higher $CO_2$ assimilation at 12° C. in comparison to 20° C. in this genotype. To gain insight into global cold-dependent gene expression of sugar beet source and sink tissues, we performed RNA-seq analyses on leaf and taproot tissue of sugar beet plants from the above genotypes exposed to cold (4° C.) or control (20° C.) conditions. For these independent cold-dependent analyses, samples were collected 14 days after transfer from 12° C. to 4° C., i.e. when metabolic accumulation of sugars (FIG. 1) and photosynthetic rate were maximally contrasting. The obtained RNA-seq reads were mapped to the sugar beet reference genome (Dohm et al., 2013 Nature 505: 546, incorporated herein by reference). Exposure to cold induced global rearrangement of gene expression in both shoot and taproot tissues. Transcript information on genes involved in photosynthesis was extracted. In a PC analysis based on expression values in leaf tissue of all 162 genes annotated as 'photosynthesis', 'photosynthesis light reaction', 'photosynthesis calvin cycle', or 'photosynthesis photorespiration' by Mapman Ontology for sugar beet, the PC1 clearly separated the temperature treatments in the three genotypes. PC1 explained 84.5%, PC2 7.1% of the variance in expression between 4° C. and 20° C. within the genotypes (FIG. 2C). Independent genotypes were not clearly separated and accordingly, expression levels of photosynthesis-related genes behaved similarly in all three genotypes (FIG. 2C). At 20° C., about 9% of all transcript reads of each genotype could be assigned to 'photosynthesis' subgroups. After exposure to 4° C., this group was represented by only 3% of all reads, indicating a drastic downregulation of photosynthesis-related genes in the cold (FIG. 2D). Downregulation of expression was for example observed for transcripts with highest homology to genes encoding RubisCO activase (BvRCA), RubisCo small subunit (BvRBCS), a Chlorophyll A/B binding protein (BvCABA), and Plastocyanin (BvPC) (FIG. 2E, upper row). Genes related to ROS processing on the other had displayed differential regulation. Whereas genes encoding Glutathione reductases were upregulated in the cold, genes encoding Superoxide-dismutase or Ascorbate reductase were down- or not significantly regulated, respectively (FIG. 2E, bottom row). In summary, the data demonstrated that sugar beet photosynthesis was extremely sensitive to chilling temperatures below 12° C. and suggested that the (hardly occurring) assimilation of CO2 does not completely account for the increase in biomass and sugar determined for leaves of cold-treated sugar beet (FIG. 1).

Figure 3:
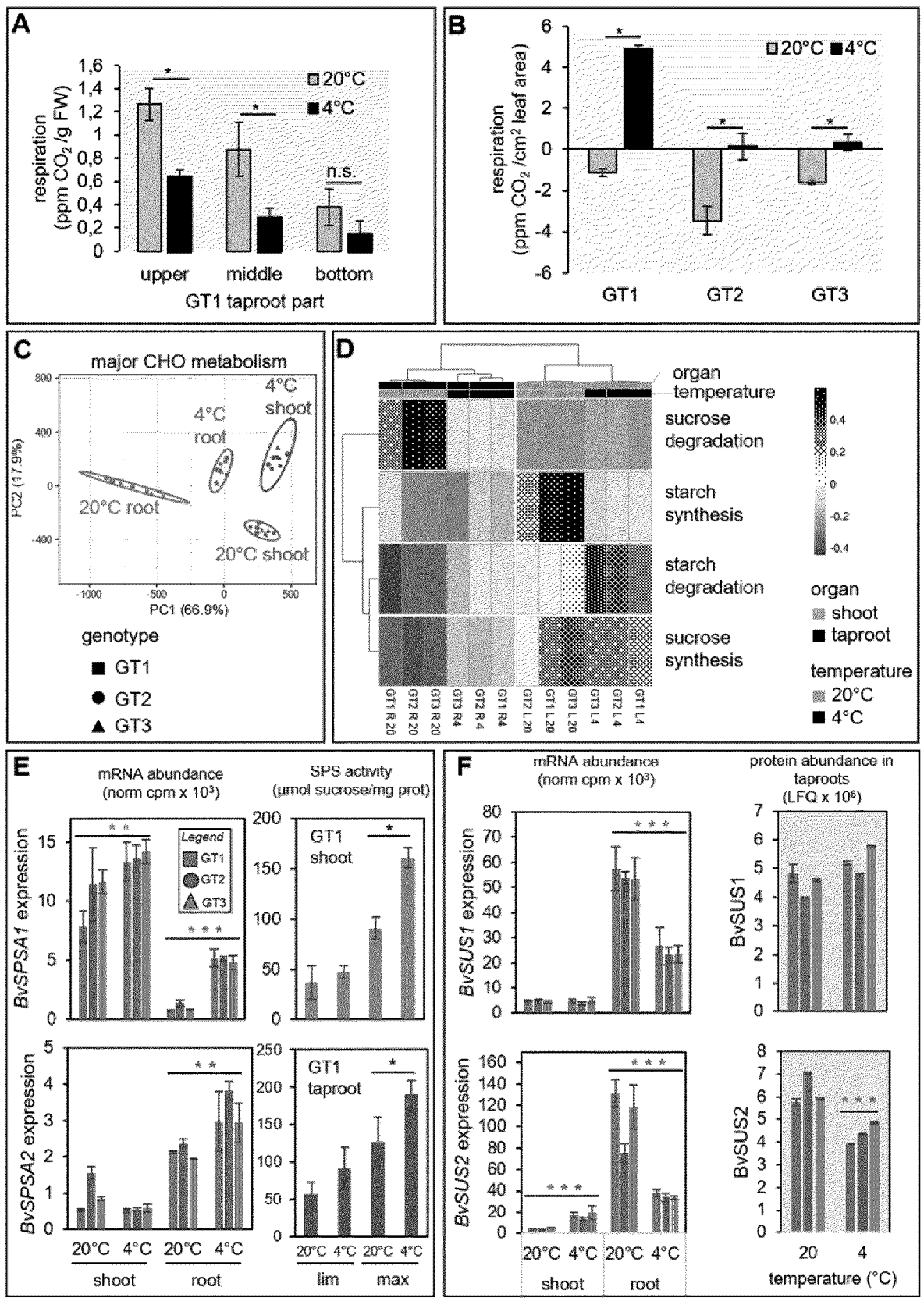
FIG. 3 shows changes in major carbohydrate metabolism in response to cold. (A) Respiration ($CO_2$ production) of different taproot regions from GT1 under control conditions (20° C., third bar on the right) or after one week transfer to 4° C. (middle of three bars). (B) Respiration ($CO_2$ production) from leaf tissue of three genotypes (GT1, GT2, GT3) under control conditions (20° C., third bar on right) or after 1-week transfer to 4° C. (middle of three bars). (C) Principal component (PC) analysis (PC1 versus PC2) for three genotypes based on expression values of 112 genes with GO annotation "major CHO metabolism" (loadings) extracted from RNA-seq data of source leaves from plants grown at 20° C. and transferred for 1 week at 12° C. followed by 14 days at 4° C. or control conditions (20° C.). (D) Heatmap analysis of grouped expression values extracted from RNA-seq data. Unit variance scaling was applied to rows. Rows are clustered using Manhattan distance and average linkage. (E) Expression values for two Sucrose Phosphate Synthase genes (BvSPSA1 and BvSPSA2) extracted from RNA-seq data of shoots and roots and SPS activity in leaves and roots under substrate (F-6-P) limiting (lim) and maximum (max) conditions. The three tested genotypes are represented in the left plots as three bars, wherein the first bar is GT1, the second bar is GT2 and the third bar is GT3. (F) Expression values for two Sucrose Synthase genes (BvSUS1 and BvSUS2) extracted from RNA-seq data of shoots and roots and protein abundance based on MS counts (label free intensities, LFQ units) from GT1, GT2, GT3. The three tested genotypes are represented as three bars, wherein the first bar is GT1, the second bar is GT2 and the third bar is GT3.

Example 4—Cold Temperatures Alter Major Carbohydrate Metabolism in Shoots and Taproots It was investigated whether the reduction of taproot sucrose concentration in the cold could be explained with increased respiration and whether cold conditions would result in differential expression of genes involved in major carbohydrate metabolism (FIG. 3). Respiration in taproot tissue was dependent on the examined part of the taproot, in that it decreased with increasing depths of the surrounding soil (FIG. 3A). This position-dependent decrease in respiration (proportionate to the depth of soil surrounding the respective part of the taproot) was also observed at 4° C., however, in each part of the taproot, respiration was—in comparison to the corresponding control—generally lower when sugar beets had been exposed to 4° C. (FIG. 3A). This data suggested that, in the cold, carbohydrates in the taproot were used for glycolytic and oxidative catabolismo a lesser extent than under the 20° C. control condition. In shoots, i.e. in source leaves of all genotypes, on the contrary, respiration increased in the cold (FIG. 3B), indicating that the mature leaves, which are hardly PS-active at this temperature (FIG. 2) had a high requirement for carbohydrate supply from other sources. One of these sources was probably starch, which decreased in leaves in the cold (FIG. 1). PC and heat map analysis, loaded with expression values of genes assigned as "major CHO metabolism", revealed organ and temperature-dependent differences (FIG. 3C, FIG. 3D). The first principal component PC1 explained 66.9% of the expression differences between roots and shoots and the PC2 accounted for 17.9% of the differences in expression between 20° C. and 4° C. Both organs showed clearer separation at 20° C. in comparison to 4° C. (FIG. 3C). The heat map representation visualizes that expression levels of genes contributing to starch degradation and synthesis in leaves were up-(starch degradation) or downregulated (starch synthesis) by cold exposure, respectively. Despite extremely low starch levels in taproots (FIG. 1), starch-related genes were also expressed and regulated in taproots (FIG. 3D).

Expression levels of sucrose synthesis genes were upregulated in roots in the cold but unchanged in shoots. Sucrose degradation genes, however, were clearly downregulated in roots but slightly upregulated in shoots (FIG. 3D). Sucrose Phosphate Synthase (SPS) and Sucrose Synthase (SUS) are key factors of sucrose degradation and synthesis and regulate carbohydrate partitioning between source and sink tissues (Voll et al., 2014; Sturm, 1996; Martin et al., 1993; Kovtun and Daie, 1995; all of which are incorporated herein by reference). A genome-wide search in the sugar beet genome ((Dohm et al., 2013 supra, incorporated herein by reference)) identified two SPS and four SUS isoforms. Bayesian analysis identified both SPS isoforms as homologues of the *Arabidopsis* SPS 'A' subgroup (Voll et al., 2014 incorporated herein by reference) (FIG. 8). The two SPS isoforms showed differential tissue specific and cold-dependent expression. In shoots of all genotypes, expression of SPSA1 was about 10-fold higher than in roots, when plants had been exposed to 20° C. Cold treatment upregulated its expression in roots up to sevenfold, but did not affect expression levels in the shoot. SPSA2 expression at 20° C. was low in shoots but high in roots of all three tested genotypes. The expression of this isoform was previously identified as taproot-specific, glucose-induced, and sucrose-repressed (Hesse et al., 1995, incorporated herein by reference). SPSA2 expression was also unaltered or even downregulated (in case of GT2) in shoots upon cold treatment, but, as opposed to SPSA1, SPSA2 expression was induced in taproots of all genotypes. On the protein level, revealed by MS-based analysis of the soluble proteome from the same taproot tissues as was used for the transcriptome analysis, BvSPSA1 but not BvSPSA2 was upregulated (FIG. 8). SPS activity, however, was higher under 4° C. in comparison to 20° C. in both protein extracts from leaves and taproots (FIG. 3E). Higher levels especially of UDP in taproots and Sucrose-6-Phosphate in both shoots and taproots in the cold in comparison to control temperatures along with the levels of the educts F-6-P and UDP-Glucose and the allosteric SPS activator G-6-P supported a scenario in which SPS activity was elevated in both roots and shoots (FIG. 8).

The expression of the four sucrose synthase isoforms showed tissue and temperature-dependent differences (FIG. 3F). While BvSUS1 and BvSUS2 isoforms were strongly expressed in roots and their corresponding proteins highly abundant, BvSUS3 and BvSUS4 were hardly expressed and their corresponding proteins were not detected by MS in a soluble proteome fraction (FIG. 3F). Both BvSUS1 and BvSUS2 were ten (BvSUS1) to hundredfold (BvSUS2) higher expressed in roots in comparison to shoots. After the cold exposure period, mRNA levels of both isoforms decreased about half in the roots. Interestingly, BvSUS2 transcript levels in shoots increased ten to twentyfold, however, without reaching the high levels in taproots (FIG. 3F). BvSUS2, but not BvSUS1 was also significantly reduced at the protein level indicating differential protein turnover dynamics of the two isoforms in the cold. Taken together, these data indicated that developing taproots shifted in the cold from a sucrose consuming/storing towards a sucrose synthesizing tissue and that leaves adopted characteristics of sink tissues.

Example 5—Cold Temperatures Reverse Phloem Translocation of Sucrose and Esculin

Figure 4:
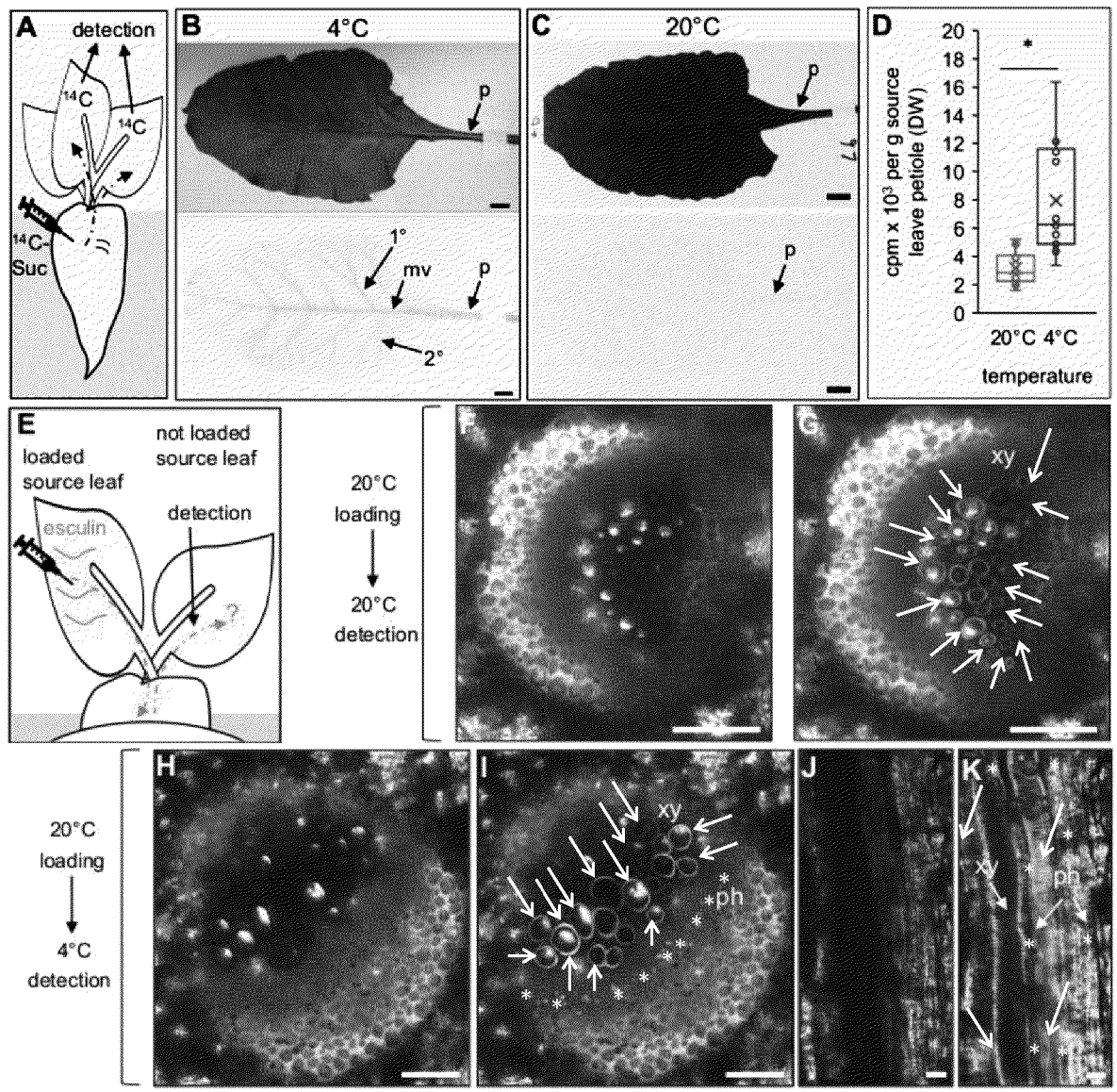
FIG. 4. Distribution of $^{14}C$-sucrose and esculin in leaves. (A-D) Autoradiography of $^{14}C$-sucrose in leaves. (A) Schematic depiction of experiment. Taproots were inoculated with $^{14}C$-sucrose solution and harvested and dried leaves were autoradiographed one week later. (B) Source leaf from a representative plant grown for one week under at 4° C. Blackening of veins indicates radioactivity incorporated and distributed into leaf tissue after injection of radiolabeled sucrose into taproots. Abbreviations: p=petiole; mv=middle vein; 1°=first order lateral vein; 2°=second order lateral vein. (C) Source leaf from representative control plant grown at 20° C. (D) radioactivity in cpm (counts per minute) measured in isolated petioles from plants grown under 4 or 20° C. Center lines show the medians; box limits indicate the 25th and 75th percentiles; whiskers extend 1.5 times the interquartile range from the 25th and 75th percentiles, outliers are represented by dots; crosses represent sample means; n=16 sample points. (E-K) Esculin loadings. Yellow fluorescence (seen as rings in (I) and marked by arrows) indicates lignified xylem vessels, blue fluorescence indicates esculin trafficking and is marked with asterisks. (E) Schematic depiction of experiment. Esculin was loaded onto the scratched surface of a source leaf of plants grown at 20° C. Loaded plants were transferred to 4° C. or kept at 20° C. Petioles of neighbored, not loaded source leaves were analyzed for esculin fluorescence in plants from 4° C. or 20° C. (F-I) Cross sections trough petiole of a source leaf not loaded with esculin from plants loaded at 20° C. (F,G) Petioles from 20° C. (F) Bright field image. (G) UV fluorescence image. (H,I): Petioles from 4° C. (H) Bright field image. (I) UV fluorescence image. (J,K) Longitudinal sections of a petiole from 4° C. J) Bright field image. K) UV fluorescence image. Abbreviations: xy: xylem, ph: phloem. Bars are 50 µm in G and H and 100 µm in E, F, I, and J.

The above examples indicated that cold-induced shoot sugar accumulation was not or only insufficiently fueled by carbon dioxide assimilation, or starch degradation, and suggested that carbon used as building block for shoot metabolites might be remobilized from taproot storage cells. To track the fate of taproot-based carbon after exposure to cold temperatures, taproot tissue was directly fed with radiolabeled $^{14}$C-sucrose by injecting the substance from the exterior into the fleshy parenchymatic taproot tissue of plants grown under 20° C. control conditions or cold-exposed plants (5 days at 12° C. and then 7 days 4° C.). The treated plants were then kept for one more week at control or cold temperatures and then dissected into individual leaves and taproots. The leaves or longitudinal thin sections of taproots were pressed and dried, and incorporated radioactivity was visualized using phosphor imaging plates and software (FIG. 4 and FIGS. 11 and 12).

This analysis surprisingly revealed that plants grown under the 4° C. condition showed distribution of radioactivity in source leaves. Radioactivity in leaves of cold-treated plants was detected in leaf veins and intensity gradually decreased towards the leaf tip indicating transport via the phloem vessels (FIG. 4B). In plants grown under control conditions, however, radioactivity could hardly be detected in source leaves (FIG. 4C). However, radioactivity was to some extent detectable in young sink leaves of control plants and extractable from combined shoot petioles (FIG. 4D). This radioactivity may represent xylem transported sucrose or derivatives due to injury of punctuated vessels as a result of the invasive inoculation procedure. The drastic water loss in shoots upon cold (FIG. 1) however indicated that at 4° C. radiolabeled sucrose was not efficiently transported to prior source leaves via the xylem but rather via the phloem.

Esculin, a phloem mobile coumarin glycoside recognized by several sucrose transporters, including the *Beta vulgaris* phloem loader BvSUT1 was loaded onto source leaves and esculin transport routes were assessed directly via detection of esculin-derived fluorescence in thin sections of leaf petioles of source leaves from the same plants, and plants which had not been loaded with esculin, after transfer to cold or under control conditions. It was observed that blue esculin fluorescence was solely detected in phloem of vascular bundles of source leaves from plants transferred to cold. However, the fluorescence was not only confined to the phloem region but also detected to some small extent in a bundle region interspersed with the yellow fluorescence of the lignified xylem vessels (FIG. 4). At 20° C., esculin fluorescence was never detected in the phloem (FIG. 4).

Figure 11:
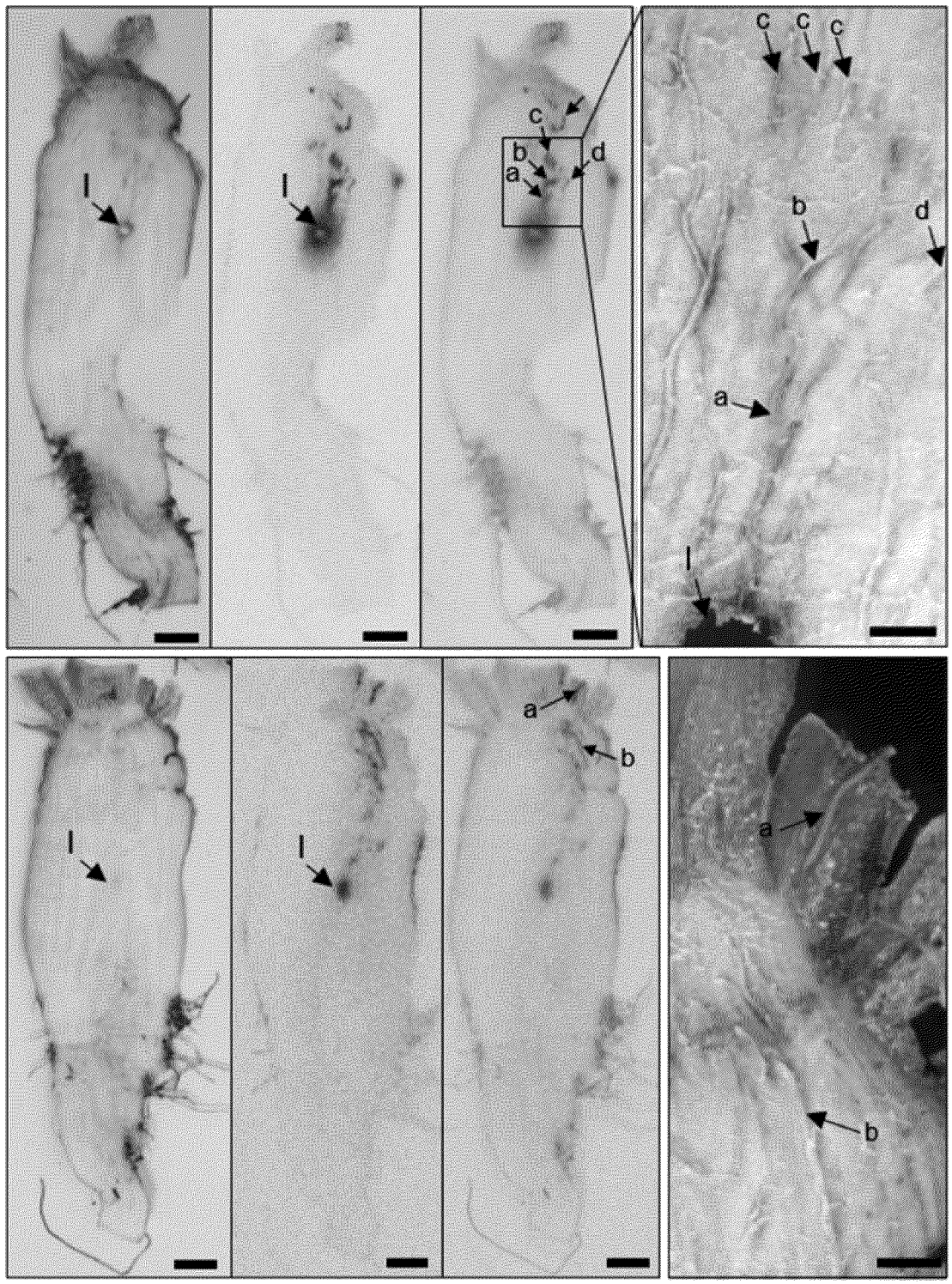
FIG. 11 shows exemplary pictures of radioactivity incorporated and distributed in taproot tissue in the cold. Plants were grown for 10 weeks at 20° C. and then transferred for 1 week to 12° C. and for 1 week to 4° C. Taproots were inoculated with $^{14}$C-sucrose and harvested 5 days later. Thin longitudinal taproot slices were prepared by hand, pressed and dried. From left to right: photographic image, phosphor-imaging recording, overlay of photography and phosphor-image recording, magnification of section region of interest. Arrowheads point towards sites of radioactivity. Bars are=5 mm for whole root pictures and 0.5 mm for magnifications (rightmost panels).
Figure 12:
FIG. 12 shows exemplary pictures of radioactivity incorporated and distributed in taproot tissue. Plants were grown for 10 weeks at 20° C. and then taproots inoculated with 14C-sucrose and harvested 5 days later. Thin longitudinal taproot slices were prepared by hand, pressed and dried. From left to right: photographic image, phosphor-maging recording, overlay of photography and phosphor-image recording, magnification of section region of interest. Arrowheads point towards sites of radioactivity. Bars are 5 mm.

To follow sucrose flow directly from the site of inoculation in the taproots, longitudinal thin sections of taproots were inoculated with the radiolabeled sucrose and exposed the tissue to phosphor imaging plates (FIGS. 11 and 12). These analyses revealed that radioactivity in taproots from plants exposed to 4° C. was detectable and concentrated in veiny or spotty structures that resided between the site of inoculation and the taproot top (crown) tissue. At higher magnification, these structures could be identified as vascular bundles (FIG. 11). In thin sections of taproots from plants grown under control conditions, no such distinct darkening of vascular structures could be observed, although some observed blackening of crown tissue indicated that radioactivity was also transported upwards into the direction of the shoot (FIG. 12). However, in most cases, radioactivity in 20° C. taproots was either merely confined to parenchymatic regions near the site of inoculation or concentrated in thick strands that reached from the site of inoculation towards the emergence of lateral roots. These results indicated that radiolabelled sucrose and esculin—the latter first being translocated to the base of the petiole of the loaded leaf and through (at least parts of) the taproot-were preferentially transported from taproots into shoots in the cold but not under control conditions and suggested that sucrose released from parenchymatic storage tissue was also transported in the same manner.

Figure 5:
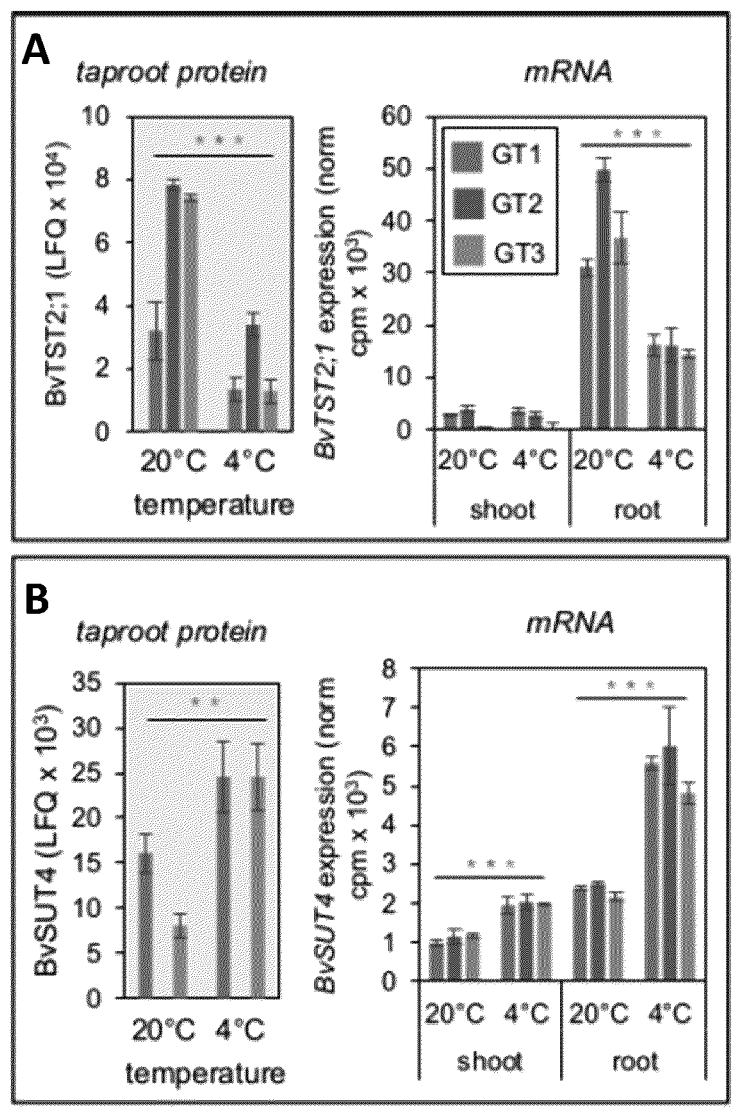
FIG. 5. Cold-dependent accumulation of BvTST2.1 and BvSUT4 in three different sugar beet genotypes. (A) Protein abundance based on MS counts given as LFQ (label free intensity) and transcript abundance of BvTST2.1 (Bv5_115690_zuju.t1) mRNA based on RNA-seq reads. Values represent means from n=6 (protein) or n=3 (mRNA) biological replicates per genotype±SE. (B) Protein abundance based on MS counts given as LFQ (label free intensity) and transcript abundance of BvSUT4 (Bv5_124860_zpft.t1) mRNA based on RNA-seq reads. Values represent means from n=6 (protein) or n=3 (mRNA) biological replicates±SE. Asterisks indicate significant differences between the 20° C. and 4° C. treatments according to t-test (*=p<0.05) For GT2, BvSUT4 LFQ values were not analysable. The three tested genotypes are represented as three bars, wherein the first bar is GT1, the second bar is GT2 and the third bar is GT3.

Example 6—Vacuolar Sucrose Importer and Exporter Genes and Proteins Show Opposite Cold-Dependent Expression We tested whether transport of sucrose from taproots to shoots in the cold could be mediated by differential activity of vacuolar sucrose importers and exporters. In sugar beet, the TST1 homologue BvTST2.1 is responsible for vacuolar sucrose accumulation. TST2.1 expression in the taproots of all tested genotypes greatly exceeds that in leaf tissue substantiating its role as the sucrose loader of taproot parenchyma vacuoles (FIG. 5). Interestingly both mRNA and protein abundance decreased significantly in all genotypes in taproots after cold treatment (FIG. 5).

Figure 14:
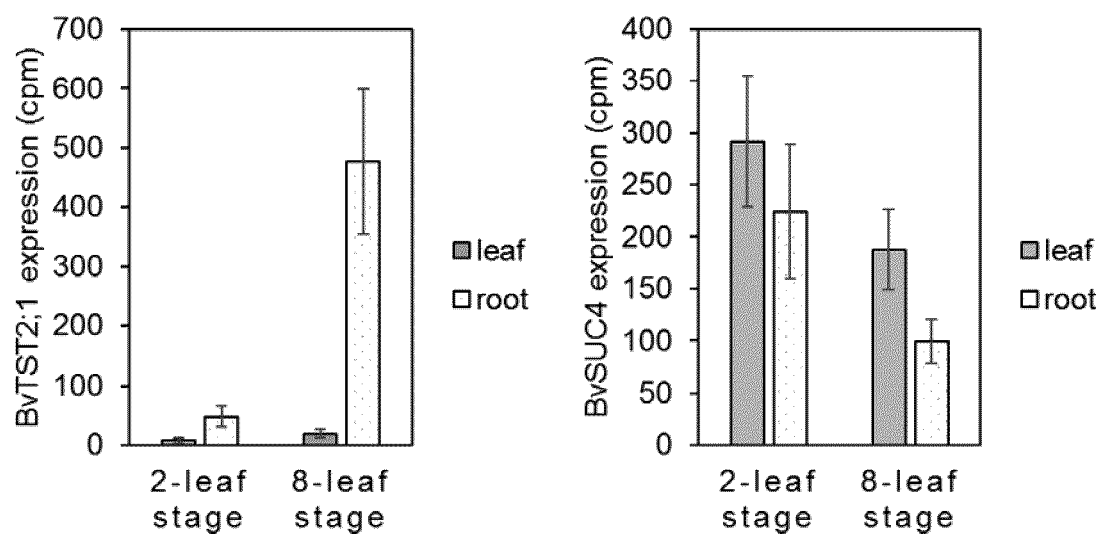
FIG. 14 shows expression of BvTST2;1 and BvSUT4 in leaves and roots of sugar beet plants from the two and eight-leaf stage.

We identified Bv5_124860_zpft.t1 as a vacuolar sucrose export transporter, and accordingly termed the corresponding transporter BvSUT4 (FIG. 13). N-terminal fusions of the BvSUT4 coding sequence with GFP transiently transformed into *Beta vulgaris* or *Arabidopsis* mesophyll protoplasts clearly indicated that BvSUT4 was a tonoplast located protein. BvSUT4 mRNA showed lower abundance in older plants in comparison to younger ones (FIG. 14). In contrast, TST2.1 mRNA increased with progression of leaf development confirming the suggested oppositional activities of the TST2;1 and SUT4 transport proteins (FIG. 14). In the RNA-seq data from the cold-treated genotypes examined in this study, SUT4 protein and mRNA levels increased significantly in taproots in the cold (FIG. 5B). These data indicated that vacuolar taproot sucrose import was decreased and vacuolar taproot sucrose release increased under cold conditions and suggested that the opposing regulation of BvTST2;1 and BvSUT4 in taproots was the underlying driving force for the delivery to and accumulation of sugars in shoots.

Example 7—Expression of Floral Regulator Genes is Adjusted in the Cold

Figure 6:
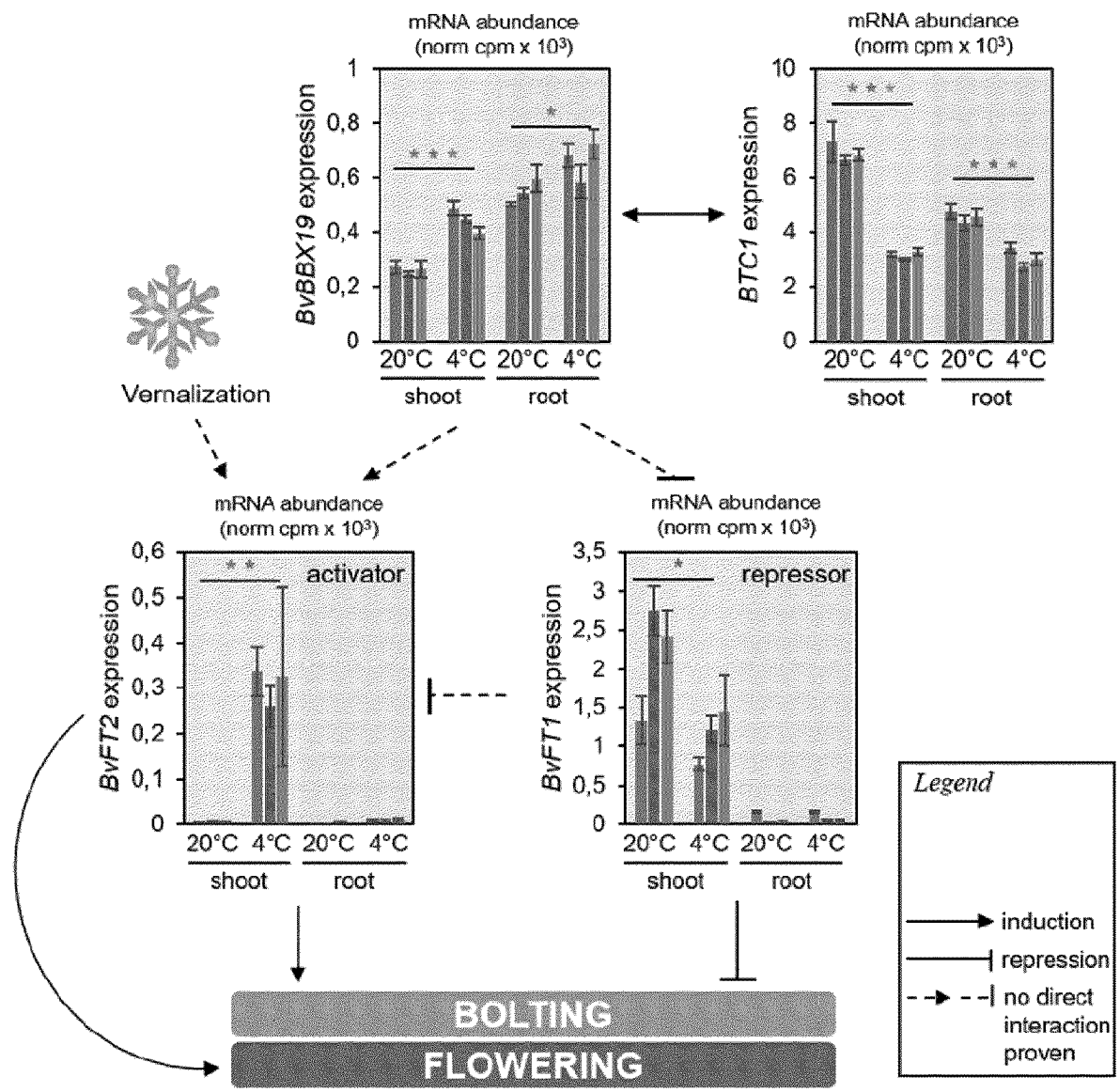
FIG. 6 shows expression of floral regulator genes. Transcript abundances of BvBBX19 (Bv9_216430_rwmw.t1), BvBTC1 (Bv2_045920_gycn.t1), BvFT1 (Bv9_214250_miuf.t1), and BvFT2 (Bv4_074700_eewx.t1) based on RNA-seq reads in shoots and taproots of three different genotypes. Values represent means from n=3 biological replicates±SE. Asterisks indicate p-values <0.05 according to double sided t-test. The three tested genotypes are represented as three bars, wherein the first bar is GT1, the second bar is GT2 and the third bar is GT3.
Figure 7:
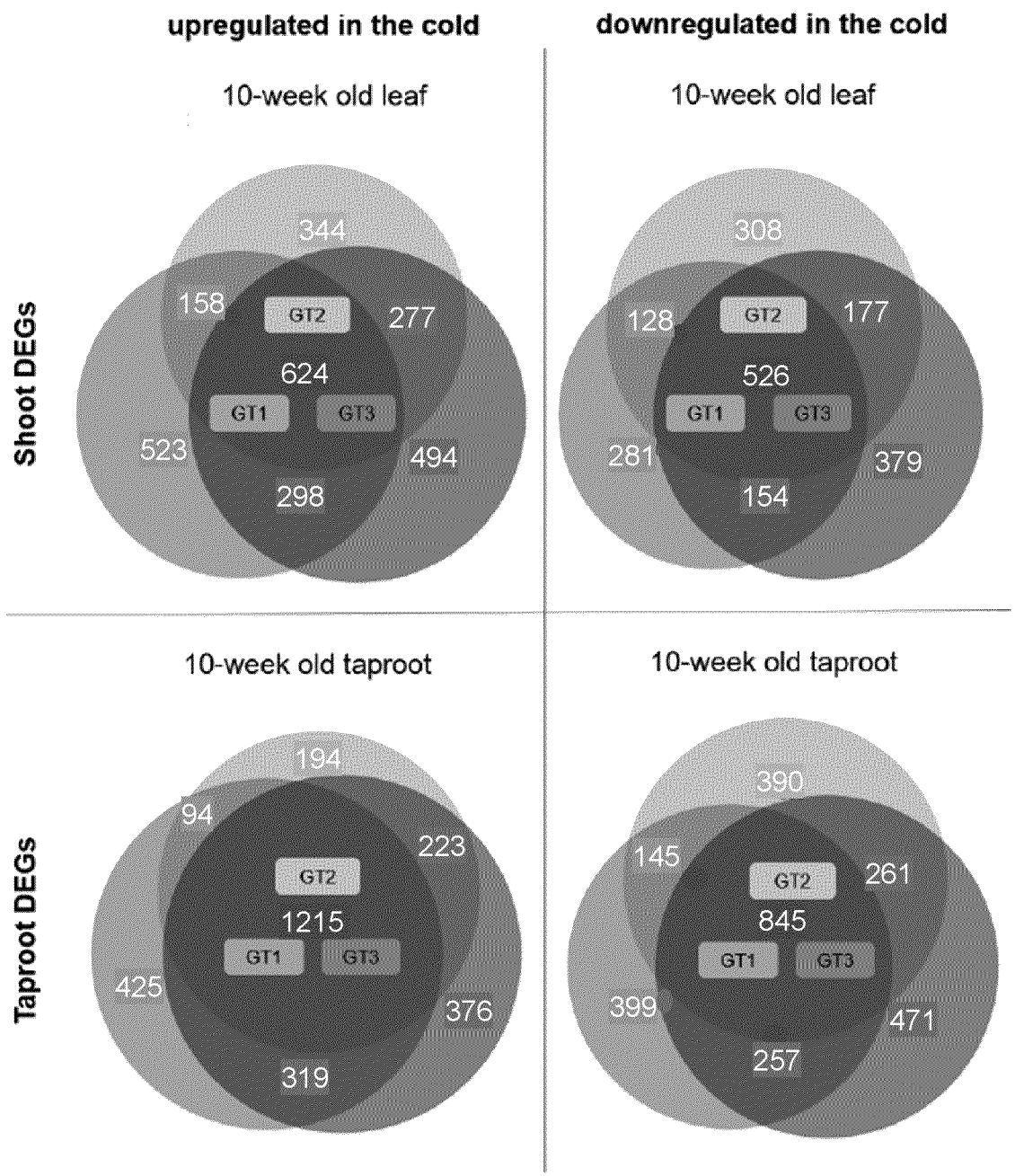
FIG. 7 shows Venn diagrams of differentially expressed genes (DEGs) in leaves and taproots. Numbers of up-(Log 2 fold change ≥1) or down-(Log 2 fold change≤−1) regulated genes (with a FDR≤0.01) are given inside circles of Venn diagrams. The total number of common DEGs (i.e. in intersections of all genotypes) was higher in taproots than in shoots (1215 up-and 845 downregulated DEGs in taproots versus 624 up-and 524 downregulated in shoots).
Figure 10:
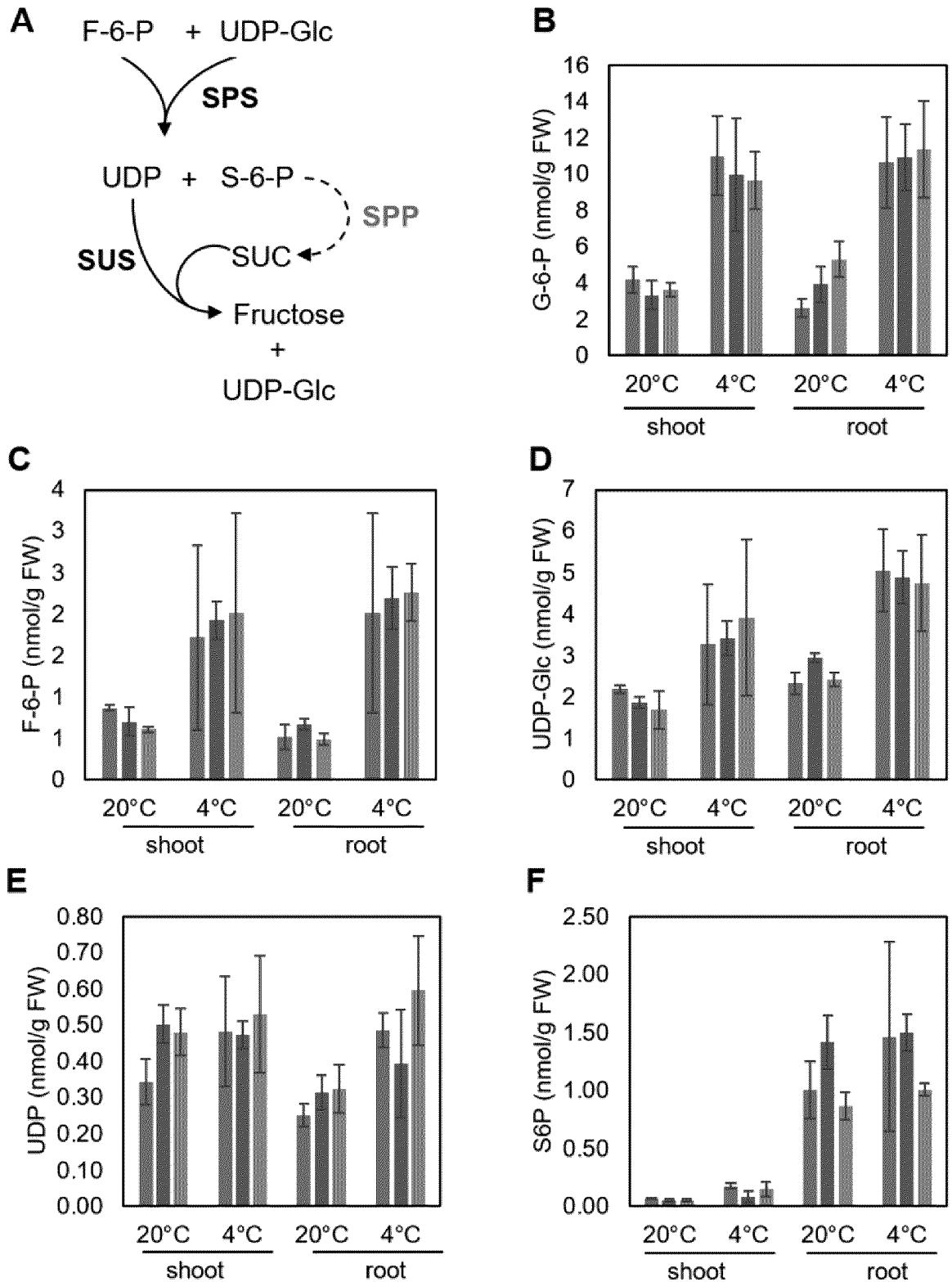
FIG. 10 shows phosphorylated metabolites in shoots and taproots of sugar beet plants. (A) schematic depiction of sucrose metabolizing processes. (B-F) concentrations of phosphorylated metabolites in shoots and roots of three different genotypes (left bar: GT1, middle bar: GT2, right bar: GT3) grown for 8 weeks under 20° C. and then either kept for 2 more weeks at 20° C. or transferred to 4° C. Abbreviations: SPS: Sucrose Phosphate Synthase, SPP: Sucrose Phosphate Phosphatase, SUS: Sucrose Synthase, G-6-P: Glucose-6-Phosphate, F-6-P: Fructose-6-Phosphate, UDP-Glc: UDP-Glucose, S-6-P: Sucrose-6-Phosphate.

It was hypothesized that the observed re-translocation of sucrose from taproots to shoots may represent a preparative metabolic and genetic rearrangement for initiation of flowering. Expression levels of flowering regulator genes were determined and a significant downregulation of the floral repressor BvFT1 and upregulation of the floral activator BvFT2 in the cold was observed in leaves (FIG. 6). The genotypes analyzed here have biennial growth behavior thus BTC1 and BBX19 may not influence FT1 expression. However, these two genes were reciprocally cold regulated. While BTC1 was downregulated in the cold, BBX19 was upregulated. In contrast to results from Pin et al. (2012 Current Biology 22: 1095-1101), where vernalized biennials had increased BTC1 mRNA levels in comparison to non-vernalized plants, BTC1 was downregulated in the cold. However, in the mentioned study, expression was analyzed after and not during early stages of vernalization. We found that BTC1 and BBX19 were expressed in both, shoots and taproots, and expression of BBX19 in taproots exceeded that in the shoot at 20° C. almost threefold. However, potential targets of theses encoded loss-of-function proteins, FT1 and FT2 were specifically and exclusively expressed in leaf tissue (FIG. 6).

In summary these data showed that the vernalization process was already transmitted to the expression level of floral regulator genes and that transcriptional changes of related genes did occur in both, shoots and taproots.

Example 8—Constitutive Overexpression of AtTMT1 Improves Cold Tolerance

AtTMT1 (genomic DNA: SEQ ID No. 7; cDNA SEQ ID No. 8: amino acid sequence SEQ ID No. 9) was expressed in sugar beet plants under the control of the CaMV 35S promoter.

The null-segregant controls demonstrated 6.7% and 20% damage after recovery from cold treatment whereas one of the two hybrids showed no damage symptoms at all and the other only weak symptoms in 3.3% of plants.

Without wishing to be bound by theory, a higher sugar concentration or a higher ratio of hexoses to sucrose may protect the plants better against cold and frost than control plants.

Figure 15:
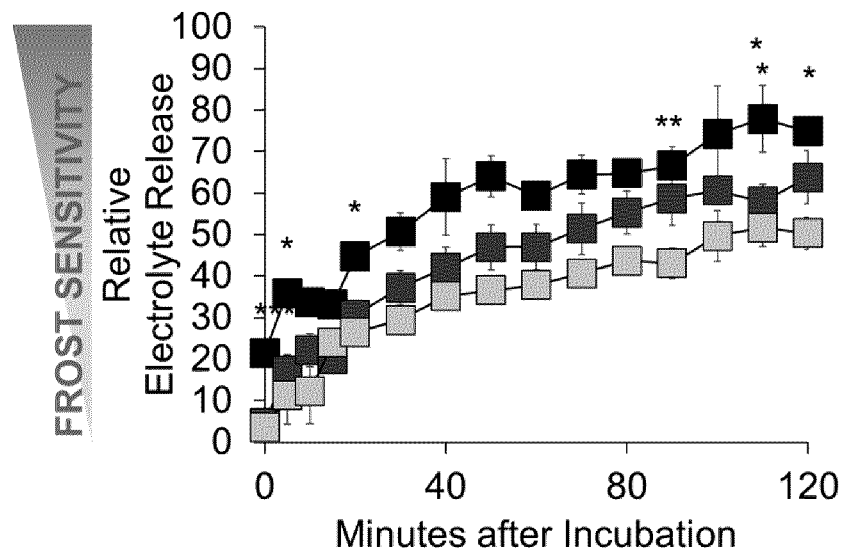
FIG. 15 shows electrolyte leakage from plants which have been engineered to over-express AtTMT1 (green squares) and control plants (black squares) following cold treatment. The extent of electrolyte release from tissue is indicative for tissue damage caused by cold treatment.

Taproot tissue was analyzed for electrolyte leakage after cold treatment. AtTMT1 over-expressors release fewer electrolytes than control plants (FIG. 15). The extent of electrolyte release from tissue in such a test is indicative for tissue damage evoked by cold treatment.

Without wishing to be bound by theory, a higher sugar concentration or a higher ratio of hexoses to sucrose may protect the plants overexpressing AtTMT better against cold and frost than control plants.

Figure 16:
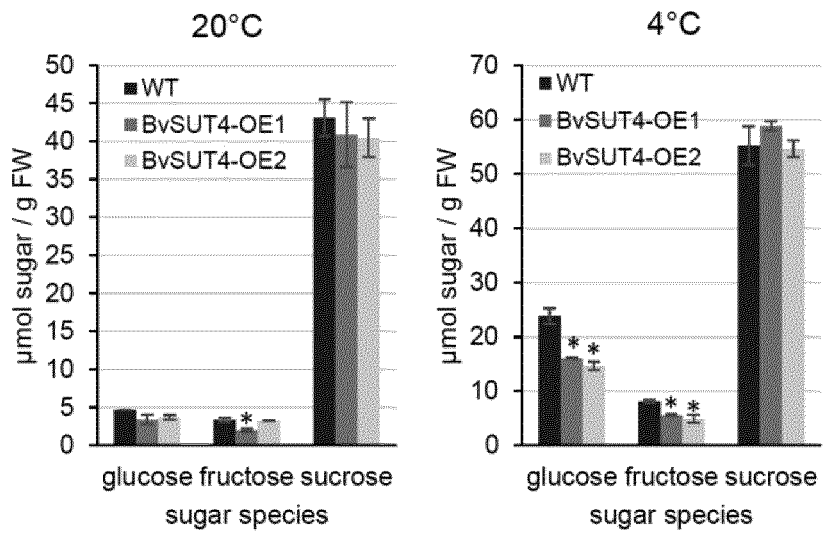
FIG. 16 shows the sugar content of plants which have been engineered to over-express BvSUT4 and control plants.
Figure 17:
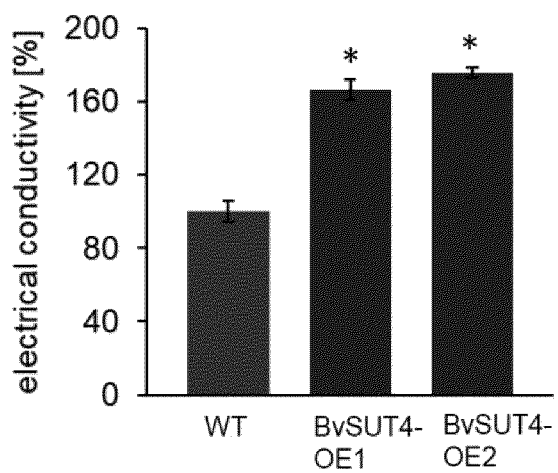
FIG. 17 shows the relative electrolyte conductivity of plants which have been engineered to over-express BvSUT4 and control plants.

Example 9—Constitutive Overexpression of BvSUT4/SUC4 Increases Sensitivity to Cold BvSUT4/SUC4 was overexpressed in *Arabidopsis* plants. Plants which over-expressed BvSUT4/SUC4 showed an increase in electrolyte leakage and hence an increased frost sensitivity (FIGS. 16, 17) relative to controls after exposure to cold temperatures.

Without wishing to be bound by theory, fewer sugars in the vacuole due to enhanced sucrose export from the vacuole mediated by BvSUT4/SUC4 may lead to increased cold sensitivity. Conversely, a down-regulation/knock-out of BvSUT4/SUC4 in sugar beet may increase cold- and frost tolerance as to less exported vacuolar sucrose, i.e. higher sucrose concentration.

Example 10—Constitutive Overexpression of BvTST2.1

Taproot-specific over-expression of BvTST2.1 is expressed in sugar beet plants under the control of a taproot-specific promoter such as the Feb. 1, 1948 promoter. The Feb. 1, 1948 promoter is described in U.S. Pat. No. 7,767,801 B2 which is incorporated herein by reference.

Tolerance of plants to cold- and frost treatment are measured relative to respective controls.

Over-expression of TST2.1 under control of a cold-insensitive promoter used here leads to high TST2.1 activity throughout cold- and frost treatment.

Without wishing to be bound by theory, taproot TST2.1 activity may compete with phloem loading for the SUT4/SUC4-mediated sucrose released from the vacuole. Consequently, a higher protective sucrose content may be kept up in the taproot.

Example 11—Increase in Frost Tolerance

To further demonstrate that sugar concentration in tap roots, particularly in storage vacuoles, increases frost tolerance, we over-expressed BvTST2.1 in tap roots and conducted a frost tolerance experiment as outlined before.

When comparing BvTST2.1 over-expressing hybrids with controls, survival rate after frost treatment was increased in transgenics (29%) compared to controls (17%).

Moreover, two weeks after recovery of plants in 20° C., transgenic hybrids had more weight than control hybrids. Total weight of transgenics was increased by 48%, leaf weight by 40% and tap root weight by 62%, compared to controls.

---

The invention claimed is:

1. A method of increasing the cold tolerance of a *Beta vulgaris* plant or part thereof and/or preventing or inhibiting bolting of a *Beta vulgaris* plant, comprising deregulating the phloem flux in said *Beta vulgaris* plant or part thereof,
wherein the method further comprises modifying said *Beta vulgaris* plant or part thereof to:
i) decrease the expression of a gene comprising:
a. the nucleotide sequence as set forth in SEQ ID NO: 4; or
b. the nucleotide sequence having the coding sequence as set forth in SEQ ID NO: 5; or
ii) decrease the activity or expression of a polypeptide:
a. encoded by the nucleotide sequence as set forth in SEQ ID NO: 4 or 5; or
b. comprising the amino acid sequence as set forth in SEQ ID NO: 6;
wherein the cold tolerance of the modified *Beta vulgaris* plant or plant part is increased relative to the cold tolerance of an unmodified *Beta vulgaris* plant or plant part,
wherein the bolting of the modified *Beta vulgaris* plant is inhibited or prevented relative to the bolting of an unmodified *Beta vulgaris* plant,
wherein the expression of the gene in the modified *Beta vulgaris* plant is decreased relative to the expression of the gene in an unmodified *Beta vulgaris* plant, and
wherein the activity or expression of the polypeptide in the modified *Beta vulgaris* plant is decreased relative to the activity or expression of the polypeptide in an unmodified *Beta vulgaris* plant.

2. The method according to claim 1, wherein the phloem flux from sink tissues to source tissues of the modified *Beta vulgaris* plant is reduced, inhibited or reversed when said *Beta vulgaris* plant or part thereof is grown in temperatures between 2° C. to 12° C. relative to the phloem flux from sink tissues to source tissues of an unmodified *Beta vulgaris* plant when said unmodified *Beta vulgaris* plant is grown in temperatures between about 2° C. to 12° C.

3. A method of deregulating phloem flux in a *Beta vulgaris* plant or part thereof; and/or increasing cold tolerance of a *Beta vulgaris* plant or part thereof; and/or preventing or inhibiting bolting in a *Beta vulgaris* plant, the method comprising:
introducing a gene into the *Beta vulgaris* plant or plant part, the gene:
a) comprising the nucleotide sequence as set forth in SEQ ID NO: or 5;
b) comprising the nucleotide sequence having the coding sequence as set forth in SEQ ID NO: 5;
c) comprising a nucleotide sequence which encodes a polypeptide comprising the amino acid sequence as set forth in SEQ ID NO: 6; or
d) encoding the amino acid sequence as set forth in SEQ ID NO: 6;
wherein the cold tolerance of the *Beta vulgaris* plant or plant part comprising the gene is increased relative to the cold tolerance of a *Beta vulgaris* plant or plant part that does not comprise the gene, and
wherein the bolting of the *Beta vulgaris* plant comprising the gene is inhibited or prevented relative to the bolting of a *Beta vulgaris* plant that does not comprise the gene.

4. A method of selecting a *Beta vulgaris* plant with deregulated phloem flux and/or increased cold tolerance and/or delayed or inhibited bolting by selection of an allele, wherein the allele is associated with deregulated phloem flux, wherein said allele is:
a) the nucleotide sequence as set forth in SEQ ID NO: or 5,
b) the nucleotide sequence having the coding sequence as set forth in SEQ ID NO: 5;
c) a nucleotide sequence encoding a polypeptide comprising the amino acid sequence as set forth in SEQ ID NO: 6; or
d) an allele of any of a), b), or c); and said method comprises determining the presence or absence of said allele, preferably wherein said allele is identified by detecting the presence of a single nucleotide polymorphisms, length polymorphisms, indel polymorphisms,
wherein the cold tolerance of the selected *Beta vulgaris* plant or plant part is increased relative to the cold tolerance of an unselected *Beta vulgaris* plant or plant part, and
wherein the bolting of the selected *Beta vulgaris* plant is inhibited or prevented relative to the bolting of an unselected *Beta vulgaris* plant.

5. A method of producing a cold tolerant *Beta vulgaris* plant and/or a *Beta vulgaris* plant with delayed or inhibited bolting, comprising crossing a donor *Beta vulgaris* plant comprising an allele associated with deregulated phloem flux wherein said allele comprises a polynucleotide sequence comprising:
a) the nucleotide sequence as set forth in SEQ ID NO: or 5;
b) the nucleotide sequence having the coding sequence as set forth in SEQ ID NO: 5;
c) a nucleotide sequence encoding a polypeptide comprising the amino acid sequence as set forth in SEQ ID NO: 6;
d) an allele of any of a), b), or c);
with a recipient *Beta vulgaris* plant that possesses commercially desirable traits,
wherein the cold tolerance of the donor *Beta vulgaris* plant or plant part comprising the allele associated with deregulated phloem flux is increased relative to the cold tolerance of a *Beta vulgaris* plant or plant part that does not comprise the allele associated with deregulated phloem flux, and wherein the bolting of the donor *Beta vulgaris* plant comprising the allele associated with deregulated phloem flux is inhibited or prevented relative to the bolting of a *Beta vulgaris* plant that does not comprise the allele associated with deregulated phloem flux.

6. A *Beta vulgaris* plant or part thereof obtained from the method according to claim 1.

7. A plant propagation material obtainable from the *Beta vulgaris* plant according to claim 6.

8. A *Beta vulgaris* plant cell wherein the *Beta vulgaris* plant cell has been modified to:
   i) decrease the expression of a gene comprising:
      a) the nucleotide sequence as set forth in SEQ ID NO: 4 or 5;
      b) the nucleotide sequence having the coding sequence as set forth in SEQ ID NO: 5; or
      c) a nucleotide sequence which encodes a polypeptide comprising the amino acid sequence as set forth in SEQ ID NO: 6;
   ii) decrease the activity or expression of a polypeptide:
      a) encoded by the nucleotide sequence as set forth in SEQ ID NO: 4 or 5;
      b) comprising the amino acid sequence as set forth in SEQ ID NO: 6,
   wherein the expression of the gene in the modified *Beta vulgaris* plant cell is decreased relative to the expression of the gene in an unmodified *Beta vulgaris* plant cell, and
   wherein the activity or expression of the polypeptide in the modified *Beta vulgaris* plant cell is decreased relative to the activity or expression of the polypeptide in an unmodified *Beta vulgaris* plant cell.

9. A modified *Beta vulgaris* plant or part thereof, comprising the modified *Beta vulgaris* plant cell according to claim 8.

10. A plant propagation material obtainable or obtained from the modified *Beta vulgaris* plant according to claim 9.

11. A method of increasing the sucrose concentration of a sucrose storage organ of a *Beta vulgaris* plant, which method comprises modifying said *Beta vulgaris* plant or part thereof to:
    i) decrease the expression of a gene comprising:
       a) the nucleotide sequence as set forth in SEQ ID NO: 4 or 5;
       b) the nucleotide sequence having the coding sequence as set forth in SEQ ID NO: 5; or
       c) a nucleotide sequence which encodes a polypeptide comprising the amino acid sequence as set forth in SEQ ID NO: 6;
    ii) decrease the activity or expression of a polypeptide:
       a) encoded by the nucleotide sequence as set forth in SEQ ID NO: 4 or 5; or
       b) comprising the amino acid sequence as set forth in SEQ ID NO: 6;
    wherein the sucrose concentration of the sucrose storage organ of the modified *Beta vulgaris* plant is increased relative to the sucrose concentration of a sucrose storage organ of an unmodified *Beta vulgaris* plant,
    wherein the expression of the gene in the modified *Beta vulgaris* plant cell is decreased relative to the expression of the gene in an unmodified *Beta vulgaris* plant cell, and
    wherein the activity or expression of the polypeptide in the modified *Beta vulgaris* plant cell is decreased relative to the activity or expression of the polypeptide in an unmodified *Beta vulgaris* plant cell.

12. A method of selecting *Beta vulgaris* plants, parts thereof or plant cells having deregulated phloem flux and/or increased cold tolerance and/or delayed or inhibited bolting after vernalization by screening said *Beta vulgaris* plant or part thereof or plant cell for:
    i) increased expression of a gene comprising:
       a) the nucleotide sequence as set forth in SEQ ID NO: 4 or 5;
       b) the nucleotide sequence having the coding sequence as set forth in SEQ ID NO: 5; or
       c) a nucleotide sequence which encodes a polypeptide comprising the amino acid sequence as set forth in SEQ ID NO: 6;
    ii) increased activity or expression of a polypeptide:
       a) encoded by the nucleotide sequence as set forth in SEQ ID NO: 4 or 5; or
       b) comprising the amino acid sequence as set forth in SEQ ID NO: 6,
    wherein the cold tolerance of the modified *Beta vulgaris* plant or plant part or plant cell is increased relative to the cold tolerance of an unmodified *Beta vulgaris* plant or plant part, and
    wherein the bolting of the modified *Beta vulgaris* plant after vernalization is delayed or prevented relative to the bolting after vernalization of an unmodified *Beta vulgaris* plant,
    wherein the expression of the gene in the modified *Beta vulgaris* plant cell is increased relative to the expression of the gene in an unmodified *Beta vulgaris* plant cell, and
    wherein the activity or expression of the polypeptide in the modified *Beta vulgaris* plant cell is increased relative to the activity or expression of the polypeptide in an unmodified *Beta vulgaris* plant cell.

13. The method according to claim 2, wherein the sink tissues are taproots.

14. The method according to claim 2, wherein the source tissues are shoots.

15. The plant propagation material according to claim 7, wherein the plant propagation material is a seed obtained from the *Beta vulgaris* plant.

* * * * *